(12) United States Patent
Adamo et al.

(10) Patent No.: US 12,365,651 B2
(45) Date of Patent: Jul. 22, 2025

(54) USE OF PIRFENIDONE AND DERIVATIVES FOR MODULATION OF B LYMPHOCYTE ACTIVITY AND ORGAN PROTECTION FROM ACUTE TISSUE DAMAGE

(71) Applicant: Washington University, St. Louis, MO (US)

(72) Inventors: Luigi Adamo, St. Louis, MO (US); Douglas L. Mann, St. Louis, MO (US); Roland Dolle, St. Louis, MO (US)

(73) Assignee: Washington University, St. Louis, MO (US)

( * ) Notice: Subject to any disclaimer, the term of this patent is extended or adjusted under 35 U.S.C. 154(b) by 689 days.

(21) Appl. No.: 16/638,424

(22) PCT Filed: Jul. 31, 2018

(86) PCT No.: PCT/US2018/044669
§ 371 (c)(1),
(2) Date: Feb. 11, 2020

(87) PCT Pub. No.: WO2019/028062
PCT Pub. Date: Feb. 7, 2019

(65) Prior Publication Data
US 2020/0165203 A1 May 28, 2020

Related U.S. Application Data

(60) Provisional application No. 62/681,418, filed on Jun. 6, 2018, provisional application No. 62/539,309, filed on Jul. 31, 2017.

(51) Int. Cl.
*C07D 213/643* (2006.01)
*A61K 47/60* (2017.01)
*A61P 9/00* (2006.01)

(52) U.S. Cl.
CPC .......... *C07D 213/643* (2013.01); *A61K 47/60* (2017.08); *A61P 9/00* (2018.01)

(58) Field of Classification Search
CPC ........ C07D 213/643; A61K 47/60; A61P 9/00
See application file for complete search history.

(56) References Cited

U.S. PATENT DOCUMENTS

| | | |
|---|---|---|
| 4,241,046 A | 12/1980 | Papahadjopoulos et al. |
| 4,394,448 A | 7/1983 | Szoka, Jr. et al. |
| 4,529,561 A | 7/1985 | Hunt et al. |
| 4,755,388 A | 7/1988 | Heath et al. |
| 4,828,837 A | 5/1989 | Uster et al. |
| 4,925,661 A | 5/1990 | Huang |
| 4,954,345 A | 9/1990 | Muller |
| 4,957,735 A | 9/1990 | Huang |
| 5,043,164 A | 8/1991 | Huang et al. |
| 5,064,655 A | 11/1991 | Uster et al. |
| 5,077,211 A | 12/1991 | Yarosh |
| 5,264,618 A | 11/1993 | Felgner et al. |
| 7,696,236 B2 | 4/2010 | Bradford |
| 8,304,413 B2 | 11/2012 | Kossen et al. |
| 8,420,674 B2 | 4/2013 | Bradford |
| 8,519,140 B2 | 8/2013 | Radhakrishnan et al. |
| 8,969,347 B2 | 3/2015 | Kossen et al. |
| 9,290,450 B2 | 3/2016 | Kossen et al. |
| 9,359,379 B2 | 6/2016 | Buckman et al. |
| 2004/0048902 A1 | 3/2004 | Kiyonaka |
| 2006/0110358 A1 | 5/2006 | Hsu |
| 2007/0053877 A1 | 3/2007 | Crager et al. |
| 2008/0194644 A1 | 8/2008 | Bradford |
| 2008/0319026 A1 | 12/2008 | Gant et al. |
| 2009/0318455 A1 | 12/2009 | Kossen et al. |
| 2011/0218515 A1 | 9/2011 | Olgin |
| 2013/0102597 A1 | 4/2013 | Kossen et al. |
| 2014/0094456 A1 | 4/2014 | Buckman et al. |
| 2014/0140932 A1 | 5/2014 | Akhtari |
| 2016/0193187 A1 | 7/2016 | Bozik et al. |
| 2016/0263090 A1 | 9/2016 | Buckman et al. |

FOREIGN PATENT DOCUMENTS

| | | |
|---|---|---|
| CN | 102241625 B | 10/2014 |
| CN | 105884680 A | 8/2016 |
| CN | 106083702 A | 11/2016 |
| DE | 2362958 A1 | 6/1974 |
| EP | 1300396 A1 | 4/2003 |
| EP | 3444247 A1 | 2/2019 |
| JP | S4987677 A | 8/1974 |
| JP | 2008508358 A | 3/2008 |
| JP | 2008544743 A | 12/2008 |
| JP | 2010530897 A | 9/2010 |
| JP | 2011522056 A | 7/2011 |

(Continued)

OTHER PUBLICATIONS

STN Registry entry for CAS RN 1590402-63-3, Accessed Feb. 25, 2023, Entry Date Apr. 25, 2014.*
STN Registry entry for CAS RN 1590402-65-5, Accessed Nov. 1, 2023, Entry Date Apr. 25, 2014.*
Van Erp, C. et al., "Long-Term Administration of Pirfenidone Improves Cardiac Function in MDX Mice," Muscle Nerve, Sep. 2006, pp. 327-334, vol. 34, No. 3.
Wang, Y. et al., "Pirfenidone attenuates cardiac fibrosis in a mouse model of TAC-induced left ventricular remodeling by suppressing NLRP3 inflammasome formation," Cardiology, 2013, pp. 1-11, vol. 126, No. 1 (Abstract).
Walker, J. et al., "A double-blind, randomized, controlled study of oral pirfenidone for treatment of secondary progressive multiple sclerosis," Mult. Scler., 2005, pp. 149-158, vol. 11.

(Continued)

*Primary Examiner* — Alicia L Otton
(74) *Attorney, Agent, or Firm* — Polsinelli PC

(57) ABSTRACT

The present disclosure relates to compositions and methods of modulating B lymphocyte activity, and organ protection after acute injury. In particular, PEG-Pirfenidone has increased half-life, improved bioavailability and is equipotent in modulating B cell activity and is particularly useful as protective agents from acute organ damage and disease caused by dysregulation of B cell activity.

18 Claims, 60 Drawing Sheets

(56) References Cited

FOREIGN PATENT DOCUMENTS

| | | |
|---|---|---|
| JP | 2014503599 A | 2/2014 |
| JP | 2016500661 A | 1/2016 |
| WO | 1997010212 A1 | 3/1997 |
| WO | 0196308 A1 | 12/2001 |
| WO | 2006017443 A2 | 2/2006 |
| WO | 2006122154 A2 | 11/2006 |
| WO | 2009035598 A1 | 3/2009 |
| WO | 2009149188 A1 | 12/2009 |
| WO | 2010065755 A1 | 6/2010 |
| WO | 2012020725 A1 | 2/2012 |
| WO | 2012102580 A1 | 8/2012 |
| WO | 2014055548 A1 | 4/2014 |
| WO | 2017177974 A1 | 10/2017 |
| WO | 2019028062 A1 | 2/2019 |

OTHER PUBLICATIONS

Xu, H. et al., "The modulatory effects of lipopolysaccharide-stimulated B cells on differential T-cell polarization," Immunology, 2008, pp. 218-228, vol. 125.

Yamagami, K. et al., "Pirfenidone exhibits cardioprotective effects by regulating myocardial fibrosis and vascular permeability in pressure-overloaded hearts," Am. J. Physiol. Heart Circ. Physiol., Jun. 2015, pp. H512-H22, vol. 309.

Yamamoto, M. et al., "Essential role for TIRAP in activation of the signalling cascade shared by TLR2 and TLR4," Nature, Nov. 21, 2002, pp. 324-329, vol. 420.

Yamazaki, T. et al., "The antifibrotic agent pirfenidone inhibits angiotensin II-induced cardiac hypertrophy in mice," Hypertens. Res., 2012, pp. 34-40, vol. 35.

Yan, X. et al., "Temporal dynamics of cardiac immune cell accumulation following acute myocardial infarction, " J. Mol. Cell Cardiol., 2013, pp. 24-35, vol. 62.

Zhang, M. et al., "The role of natural IgM in myocardial ischemia-reperfusion injury," J. Mol. Cell Cardiol., 2006, pp. 62-67, vol. 41.

Zhang, W. et al., "Necrotic Myocardial Cells Release Damage-Associated Molecular Patterns That Provoke Fibroblast Activation In Vitro and Trigger Myocardial Inflammation and Fibrosis In Vivo," J. Am. Heart Assoc., 2015, pp. 1-19, vol. 4, e001993.

Zhou, X. et al., "Robustly detecting differential expression in RNA sequencing data using observation weights," Nucleic Acids Res., 2014, pp. 1-10, vol. 42, No. 11, e91.

Zouggari, Y. et al., "B lymphocytes trigger monocyte mobilization and impair heart function after acute myocardial Infarction," Nat. Med., Oct. 2013, pp. 1273-1280, vol. 19, No. 10.

Anders, S. et al., "HTSeq—a Python framework to work with high-throughput sequencing data, " Bioinformatics, 2015, pp. 166-169, vol. 31, No. 2.

Arumugam, T. et al., "Pirfenidone attenuates ischaemia-reperfusion injury in the rat small intestine," Clin. Exp. Pharmacol. Physiol., Oct. 2002, pp. 996-1000, vol. 29, No. 11 (Abstract).

Bizargity, P. et al., "Inhibitory Effects of Pirfenidone on Dendritic Cells and Lung Allograft Rejection," Transplantation, Jul. 27, 2012, pp. 114-122, vol. 94, No. 2.

Bonner, F. et al., "Resident Cardiac Immune Cells and Expression of the Ectonucleotidase Enzymes CD39 and CD73 after Ischemic Injury," PLoS One, Apr. 2012, pp. 1-9, vol. 7, No. 4, e34730.

Boros, P. et al., "New Cellular and Molecular Immune Pathwaysin Ischemia/Reperfusion Injury," Am. J. Transplant., 2006, pp. 652-658, vol. 6.

Boussiotis, V. et al., "Tumor necrosis factor alpha is an autocrine growth factor for normal human B cells," PNAS, Jul. 1994, pp. 7007-7011, vol. 91.

Burchfield, J. et al., "The Cytoprotective Effects of Tumor Necrosis Factor Are Conveyed Through Tumor Necrosis Factor Receptor-Associated Factor 2 in the Heart," Circ. Heart Fail., 2010, pp. 157-164, vol. 3.

Carter, N., "Pirfenidone: In Idiopathic Pulmonary Fibrosis," Drugs, Sep. 10, 2011, pp. 1721-1732, vol. 71, No. 13.

Cordero-Reyes, A. et al., "Full Expression of Cardiomyopathy Is Partly Dependent on B-Cells: A Pathway That Involves Cytokine Activation, Immunoglobulin Deposition, and Activation of Apoptosis," J. Am. Heart Assoc., Jan. 14, 2016, pp. 1-12, vol. 5, No. 1, e002484.

Epelman, S. et al., "Embryonic and Adult-Derived Resident Cardiac Macrophages Are Maintained through Distinct Mechanisms at Steady State and During Inflammation," Immunity, Jan. 16, 2014, pp. 91-104, vol. 40.

Falb, E. et al., "A highly efficient Suzuki-Miyaura methylation of pyridines leading to the drug pirfenidone and its CD3 version (SD-560)," Green Chem., 2017, pp. 5046-5053, vol. 19.

GEO Accession No. GPL21493, "Illumina HiSeq 3000 (Mus musculus)," Feb. 22, 2016; 1 pg.

GEO Accession No. GSE112984, "Characterization of myocardial B cells in naive hearts, acutely injured hearts and acutely injured hearts of mice treated with Pirfenidone," Apr. 11, 2018; 2 pgs.

Horckmans, M. et al., "Pericardial Adipose Tissue Regulates Granulopoiesis, Fibrosis and Cardiac Function After Myocardial Infarction," Circulation, Feb. 27, 2018, pp. 948-960, vol. 137.

Hua, Z. et al., "TLR signaling in B-cell development and activation," Cell Mol. Immunol., 2013, pp. 103-106, vol. 10.

Huang, D. et al., "Systematic and integrative analysis of large gene lists using DAVID bioinformatics resources," Nat. Protoc., 2009, pp. 44-57, vol. 4.

International Search Report and Written Opinion dated Oct. 1, 2018 from related Patent Application No. PCT/US2018/044669; 10 pgs.

Ismail, M. et al., "Novel Pirfenidone Analogs as Antifibrotic Agents: Synthesis and Antifibrotic Evaluation of 2-Pyridones and Fused Pyridones," Med. Chem. Res., Oct. 2005, pp. 382-403, vol. 14, No. 7.

Kaibori, M. et al., "Pirfenidone protects endotoxin-induced liver injury after hepatic ischemia in rats," Transplant Proc., Sep. 2004, pp. 1973-1974, vol. 36, No. 7 (Abstract).

Kanno, S. et al., "Echocardiographic Evaluation of Ventricular Remodeling in a Mouse Model of Myocardial Infarction," J. Am. Soc. Echocardiogr., Jun. 2002, pp. 601-609, vol. 15, No. 6.

Kantor, A. et al., "Differential development of progenitor activity for three B-cell lineages," PNAS, Apr. 1992, pp. 3320-3324, vol. 89.

Avine, K. et al., "Coronary Collaterals Predict Improved Survival and Allograft Function in Patients With Coronary Allograft Vasculopathy," Circ. Heart Fail., 2013, pp. 773-784, vol. 6.

Lavine, K. et al., "Repetitive Myocardial Ischemia Promotes Coronary Growth in the Adult Mammalian Heart," J. Am. Heart Assoc., 2013, pp. 1-17, vol. 2, e000343.

Lavine, K. et al., "Distinct macrophage lineages contribute to disparate patterns of cardiac recovery and remodeling in the neonatal and adult heart," PNAS, Nov. 11, 2014, p. 16029-16034, vol. 111, No. 45, with Correction, PNAS, Mar. 8, 2016, p. E1414, vol. 113, No. 10.

Lee, K. et al., "Pirfenidone Prevents the Development of a Vulnerable Substrate for Atrial Fibrillation in a Canine Model of Heart Failure," Circulation, 2006, pp. 1703-1712, vol. 114.

Li, C. et al., "Pirfenidone controls the feedback loop of the AT1R/p38 MAPK/renin-angiotensin system axis by regulating liver X receptor-alpha in myocardial infarction-induced cardiac fibrosis," Sci. Rep., 2017, pp. 1-11, vol. 7, No. 40523.

Lou, Q. et al., "Design, Synthesis and Antifibrotic Activities of Carbohydrate-Modified 1-(Substituted aryl)-5-rifluoromethyl-2(1H) Pyridones," Molecules, 2012, pp. 884-896, vol. 17.

Ma, Z. et al., "Synthesis and biological evaluation of the pirfenidone derivatives as antifibrotic agents," Bioorg. Med. Chem. Lett., 2014, pp. 220-223, vol. 24.

Mallick, I. et al., "Ischemia-Reperfusion Injury of the Intestine and Protective Strategies Against Injury," Dig. Dis. Sci., Sep. 2004, pp. 1359-1377, vol. 49, No. 9.

Mann, D., "The Emerging Role of Innate Immunity in the Heart and Vascular System: For Whom the Cell Tolls," Circ. Res., 2011, pp. 1133-1145, vol. 108.

Mann, D., "Innate Immunity and the Failing Heart: The Cytokine Hypothesis Revisited," Circ. Res., 2015, pp. 1254-1268, vol. 116.

(56) References Cited

OTHER PUBLICATIONS

Mei, S. et al., "Protection of Pirfenidone against an Early Phase of Oleic Acid-Induced Acute Lung Injury in Rats," J. Pharmacol. Exp. Therapeutics, 2005, pp. 379-388, vol. 313.

Miric, G. et al., "Reversal of cardiac and renal fibrosis by pirfenidone and spironolactone in streptozotocin-diabetic rats," Br. J. Pharmacol., 2001, pp. 687-694, vol. 133.

Mirkovic, S. et al., "Attenuation of cardiac fibrosis by pirfenidone and amiloride in DOCA-salt hypertensive rats," Br. J. Pharmacol., 2002, pp. 961-968, vol. 135.

Misharin, A. et al., "Eosinophil contamination of thioglycollate-elicited peritoneal macrophage cultures skews the functional readouts of in vitro assays," J. Leukoc. Biol., 2012, pp. 325-331, vol. 92.

Nguyen, D. et al., "Pirfenidone mitigates left ventricular fibrosis and dysfunction after myocardial infarction and reduces arrhythmias," Heart Rhythm, 2010, pp. 1438-1445, vol. 7.

Nossuli, T. et al., "A chronic mouse model of myocardial ischemia-reperfusion: essential in cytokine studies," Am. J. Physiol. Heart Circ. Physiol., 2000, pp. H1049-H1055, vol. 278.

Nour, M. et al., "Ischemia-Reperfusion Injury in Stroke," Intervent. Neurol., 2012, pp. 185-199, vol. 1, S. Karger AG, Basel.

Pubchem, "2-(2-Methyoxyethoxy)-1-pentylpiperidine," CID 19610724, Dec. 5, 2007, pp. 1-10.

Pubchem, "Pirfenidone," CID 40632, Jun. 24, 2005, pp. 1-53.

Rahman, Z., "Impaired clearance of apoptotic cells in germinal centers: implications for loss of B cell tolerance and Induction of autoimmunity," Immunol. Res., 2011, pp. 125-133, vol. 51.

Ramos, G. et al., "Myocardial aging as a T-cell-mediated phenomenon," PNAS, Mar. 21, 2017, pp. E2420-E2429, vol. 114, No. 12.

Rubtsova, K. et al., "Age-Associated B Cells: A T-bet-Dependent Effector with Roles in Protective and Pathogenic Immunity," J. Immunol., 2015, pp. 1933-1937, vol. 195.

Rymer, J. et al., "Failure to Launch: Targeting Inflammation in Acute Coronary Syndromes," JACC: Basic to Translational Sci., Aug. 2017, pp. 484-497, vol. 2, No. 4.

Schaefer, C. et al., "Antifibrotic activities of pirfenidone in animal models," Eur. Respir. Rev., 2011, pp. 85-97, vol. 20, No. 120.

Shen, P. et al., "Antibody-independent functions of B cells: a focus on cytokines," Nat. Rev. Immunol., Jul. 2015, pp. 441-451, vol. 15.

Silverman, G. et al., "B cell modulation in rheumatology," Curr. Opin. Pharmacol., 2007, pp. 426-433, vol. 7.

Tamura, Y. et al., "Design, synthesis and identification of novel benzimidazole derivatives as highly potent NPY Y5 receptor antagonists with attractive in vitro ADME profiles," Bioorg. Med. Chem. Lett., 2012, pp. 5498-5502, vol. 22.

Trapnell, C. et al., "TopHat: discovering splice junctions with RNA-Seq," Bioinformatics, 2009, pp. 1105-1111, vol. 25, No. 9.

Tzeng, H-P. et al., "Dysferlin Mediates the Cytoprotective Effects of TRAF2 Following Myocardial Ischemia Reperfusion Injury," J. Am. Heart Assoc., 2014, pp. 1-26, vol. 3, e000662.

Grattendick, Ken J., Research Communications in Molecular Pathology and Pharmacology, (2010), vol. 122-123 (44567), ISSN 0004818458, pp. 27-50—abstract only.

Pasut, G. et al., Expert Opinion on Therapeutics Patents, (2004), vol. 14(6), ISSN 0004818460, pp. 859-894.

Sorrell T.N., "Organic Chemistry," University Science Books, Sausalito, 1999.

Wang Y., et al., "Pirfenidone Attenuates Cardiac Fibrosis in a Mouse Model of TAC-Induced Left Ventricular Remodeling by Suppressing NLRP3 Inflammasome Formation," Cardiology, 2013, vol. 126, No. 1, pp. 1-11.

Japanese Office Action for Japanese application No. 2020-506221, mailed Jul. 5, 2022, 7 pages.

Japanese Office Action for Japanese application No. 2020-506221, mailed Mar. 14, 2023, 7 pages.

Extended European Search Report for European Application No. 18841771.1, mailed Mar. 19, 2021, 15 Pages.

International Preliminary Report on Patentability for International Application No. PCT/US2018/044669, mailed Feb. 13, 2020, 08 Pages.

European Exam Report for EP application No. 18841771.1, mailed on Apr. 4, 2022, 4 pages.

European Exam Report for EP application No. 18841771.1, mailed on Feb. 16, 2023, 3 pages.

\* cited by examiner

CD19⁺ CD11b⁺

| Pathway | Differentially regulated | |
|---|---|---|
| | DTR vs naive | DTR-PFD vs naive |
| Hematopoietic cell lineage | ✓ | |
| Cytokine-cytokine receptor interaction | ✓ | |
| B cell receptor signaling pathway | ✓ | |
| Cell adhesion molecules (CAMs) | ✓ | |
| Antigen processing and presentation | ✓ | |
| MAPK signaling pathway | ✓ | |

| Pathway | Differentially regulated | |
|---|---|---|
| | DTR vs naive | DTR-PFD vs naive |
| Cytokine-cytokine receptor interaction | ✓ | |
| Hematopoietic cell lineage | ✓ | ✓ |
| Toll-like receptor signaling pathway | ✓ | |
| Chemokine signaling pathway | ✓ | |
| TNF signaling pathway | ✓ | |

FIG. 10D

|  | $T_{1/2}$ (h) | CL(/F) (mL/h/kg) |
|---|---|---|
| Pirfenidone IV 40 mg/KG | 0.471 | 2398 |
| Pegydone 6 IV 40 mg/Kg | 0.850 | 2448 |

FIG. 12C

|  | F% (bioavailability) |
|---|---|
| Pirfenidone PO 40 mg/kg | 49.0% |
| Pegydone 6 PO 40 mg/Kg | 30.6% |

FIG. 12D

USE OF PIRFENIDONE AND DERIVATIVES FOR MODULATION OF B LYMPHOCYTE ACTIVITY AND ORGAN PROTECTION FROM ACUTE TISSUE DAMAGE

CROSS REFERENCE TO RELATED APPLICATIONS

This application claims the benefit of International Patent Application number PCT/US2018/044669, filed Jul. 31, 2018, which claims the benefit of U.S. Provisional Application 62/539,309, filed Jul. 31, 2017 and U.S. Provisional Application No. 62/681,418, filed Jun. 6, 2018, the disclosures of which are hereby incorporated by reference in their entirety.

GOVERNMENTAL RIGHTS

This invention was made with government support under grant number HL007081 awarded by National Institutes of Health. The government has certain rights in the invention.

FIELD OF THE INVENTION

The present invention encompasses methods of modulating B lymphocyte activity and. This application generally relates to compositions and methods to protect organs from acute injury. In particular, the disclosure relates to compositions and methods of modulating B lymphocyte activity using Pirfenidone or a Pirfenidone derivative.

BACKGROUND OF THE INVENTION

The epidemic of heart failure is currently one of the greatest challenges in healthcare. Heart failure is a serious disease with severe prognosis and extremely high costs of care, and it is a major driver of the skyrocketing medical spending. Today, there are 5.8 million adults living in the US with heart failure and >550,000 new cases diagnosed each year. 1 in 5 Americans is expected to develop heart failure, which contributes to about 300,000 deaths/year. With $30.7 billion spent every year caring for heart failure patients, heart failure is single handedly responsible for approximately 2% of total US healthcare cost. According to the American Heart Association, the medical costs of heart failure are rising rapidly, and they are projected to reach $53 billion/year by 2030. There is a need for innovative therapies to stop this trend.

When the heart is damaged the immune system is activated, and part of the immune response amplifies heart damage and impairs healing. This can create significant problems for patients. In fact, if the extent of heart damage becomes sufficiently large, it triggers a series of compensatory events that eventually lead to heart failure, a condition characterized by poor exercise tolerance, fluid retention and markedly increased rates of disability and mortality. We currently have drugs to modulate the compensatory mechanisms that amplify heart dysfunction. However medications are needed to reduce the amplification of heart damage or to promote immediate heart healing.

Pirfenidone is a drug approved by the FDA for the treatment of Interstitial Pulmonary Fibrosis. Initially described as an anti-pyretic, Pirfenidone was found to have anti fibrotic activities in vitro and in vivo. Pirfenidone was tested in humans for the treatment of Interstitial Pulmonary Fibrosis, an orphan disease with severe prognosis, and it was approved for clinical use first in Japan (2008), then in Europe (2011) and eventually in the US (2014). Pirfenidone is a safe drug and has been given to tens of thousands of patients with basically no reported serious side effects.

SUMMARY OF THE INVENTION

One aspect of the present disclosure is directed to compounds of Formula (I):

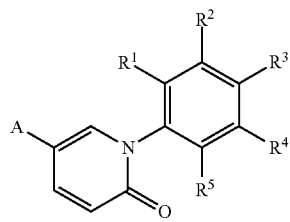

wherein:

$R^1$, $R^2$, $R^3$, $R^4$, and $R^5$ are each independently selected from the group consisting of hydrogen, deuterium or L-X—B;

wherein L is a linker which comprises a $C_{1-12}$ alkyl; X is O-PEG NH$(CH_2)_m$O-PEG, or S$(CH_2)_m$O-PEG; m is an integer from 1-10; wherein PEG is selected the group of mPEG (methoxy polyethylene glycol), linear PEG, branched PEG, multi-arm PEG, and PEG-lipid; B is selected from the group consisting of hydrogen, deuterium a substituted or unsubstituted $C_1$ to $C_6$ alkyl, a substituted or unsubstituted $C_1$ to $C_6$ alkenyl, a substituted or unsubstituted $C_1$ to $C_6$ alkynyl, a substituted or unsubstituted aryl, and a substituted or unsubstituted heteroaryl, or deuterated versions thereof; and A is selected from the group consisting of hydrogen, deuterium, halogen, $CF_3$, $CD_3$, CN, OH, $OCH_3$, OR", SR", NR"R", NR"COR", NR"CONR"R", NR"$CO_2$R", COR", $CO_2$R", NOR", $NO_2$, CONR"R", OC(O)NR"R", $SO_2$R", $SO_2$NR"R", NR"$SO_2$R", NR"$SO_2$NR"R", C(O)C(O)R", and C(O)CH$_2$C(O)R", a substituted or unsubstituted $C_1$ to $C_6$ alkyl, a substituted or unsubstituted $C_1$ to $C_6$ alkenyl, a substituted or unsubstituted $C_1$ to $C_6$ alkynyl, a substituted or unsubstituted aryl, and a substituted or unsubstituted heteroaryl;

R" may be independently selected from the group consisting of hydrogen, substituted $C_1$-$C_4$ aliphatic moiety, aliphatic moiety containing nitrogen, oxygen, or sulfur, or alternately, two R" moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur.

Another aspect of the present disclosure is directed to compounds of Formula (II):

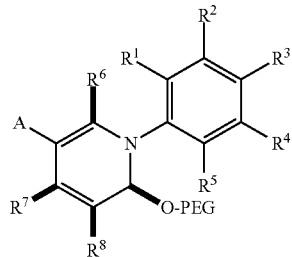

wherein:

$R^1$, $R^2$, $R^3$, $R^4$, $R^5$, $R^6$, $R^7$, and Fe are each independently selected from the group consisting of hydrogen, deuterium or L—X—B;
  wherein L is a linker which comprises a $C_{1-12}$ alkyl; X is O-PEG NH$(CH_2)_m$O-PEG, or S$(CH_2)_m$O-PEG; m is an integer from 1-10; wherein PEG is selected the group of mPEG (methoxy polyethylene glycol), linear PEG, branched PEG, multi-arm PEG, and PEG-lipid; B is selected from the group consisting of hydrogen, deuterium a substituted or unsubstituted $C_1$ to $C_6$ alkyl, a substituted or unsubstituted $C_1$ to $C_6$ alkenyl, a substituted or unsubstituted $C_1$ to $C_6$ alkynyl, a substituted or unsubstituted aryl, and a substituted or unsubstituted heteroaryl, or deuterated versions thereof;

O-PEG is selected the group of mPEG (methoxy polyethylene glycol), linear PEG, branched PEG, multi-arm PEG, and PEG-lipid, wherein the PEG is end-cap is selected from the group consisting of hydrogen, deuterium a substituted or unsubstituted $C_1$ to $C_6$ alkyl, a substituted or unsubstituted $C_1$ to $C_6$ alkenyl, a substituted or unsubstituted $C_1$ to $C_6$ alkynyl, a substituted or unsubstituted aryl, and a substituted or unsubstituted heteroaryl, or deuterated versions thereof;

A is selected from the group consisting of hydrogen, deuterium, halogen, $CF_3$, $CD_3$, CN, OH, $OCH_3$, OR", SR", NR"R", NR"COR", NR"CONR"R", NR"$CO_2$R", COR", $CO_2$R", NOR", $NO_2$, CONR"R", OC(O)NR"R", $SO_2$R", $SO_2$NR"R", NR"$SO_2$R", NR"$SO_2$NR"R", C(O)C(O)R", and C(O)$CH_2$C(O)R", a substituted or unsubstituted $C_1$ to $C_6$ alkyl, a substituted or unsubstituted $C_1$ to $C_6$alkenyl, a substituted or unsubstituted $C_1$ to $C_6$ alkynyl, a substituted or unsubstituted aryl, and a substituted or unsubstituted heteroaryl;

R" may be independently selected from the group consisting of hydrogen, substituted $C_1$-$C_4$ aliphatic moiety, aliphatic moiety containing nitrogen, oxygen, or sulfur, or alternately, two R" moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur.

Another aspect of the present disclosure is directed to a method of modulating B cell activity in a subject in need thereof. The method comprises administering to the subject a composition comprising a therapeutically effective amount of Pirfenidone, a Pirfenidone derivative, a compound of Formula (I), a compound of Formula (II) or combinations thereof, as described herein.

An additional aspect of the present disclosure is directed to a method for reducing organ damage in a subject, the method comprising administering a composition comprising a therapeutically effective amount of Pirfenidone, a Pirfenidone derivative, a compound of Formula (I), a compound of Formula (II) or combinations thereof, as described herein.

A further aspect of the present disclosure is directed to a method of treating an age-related organ dysfunction, the method comprising administering a composition comprising a therapeutically effective amount of Pirfenidone, a Pirfenidone derivative, a compound of Formula (I), a compound of Formula (II) or combinations thereof, as described herein.

The present invention provides a method of using Pirfenidone, a Pirfenidone derivative, a compound of Formula (I), a compound of Formula (II) or combinations thereof to modulate the activity of B lymphocytes in vivo and in vitro. Through the modulation of B lymphocyte function, Pirfenidone, a Pirfenidone derivative, a compound of Formula (I), a compound of Formula (II) or combinations thereof can exert powerful cardio protective effects in the context of acute cardiac injury.

Every year, just in the United States, about 1 million people develop new heart damage because of heart attacks, myocarditis or drug related toxicities. Roughly 20% of them end up developing heart failure. These patients have significantly increased rates of mortality and disability. They need close medical follow up and usually are treated with a lifelong regimen of 5 to 7 drugs. If their heart function gets low enough, they need implantable cardioverter defibrillators to prevent sudden death. A fraction of them progresses to end stage disease needs invasive testing to optimize therapy and might receive placement of implantable pumps to support the heart (LVADs) or cardiac transplants. This invention may be used in all patients who have recently experienced heart damage, significantly reducing the risk of progressing to heart failure with all its associated costs and issues. This invention may be used as a preventive measure in subjects when cardiac injury anticipated, preventing or slowing the progression of cardiac injury.

Pirfenidone, a Pirfenidone derivative, a compound of Formula (I), a compound of Formula (II) or combinations thereof may be used as a protective agent to protect other organs from acute injury (e.g. brain, kidney, liver, gut, etc.) or may be used as a protective agent in other disease processes characterized by a dysregulation of B cell activity (e.g. multiple sclerosis, scleroderma, etc.).

BRIEF DESCRIPTION OF THE FIGURES

FIG. 1A shows Kaplan-Meier survival curves of DTR control and DTR-PFD mice (n=20 per group). FIG. 1B shows serum troponin levels measured at day 4 post diphtheria toxin (DT) treatment in DTR-PFD and DTR-Control animals (n=23/group). FIG. 1C shows cardiac myocyte apoptosis measured at day 4 post treatment with diphtheria toxin (DT); upper panels are representative histological sections of myocardium from DTR-Control and DTR-PFD mice at 40× magnification, lower panel summarizes group data (n=6 mice/group, 4 sections per animal analyzed). FIG. 1D shows evans blue dye uptake at day 4 post diphtheria toxin treatment in DTR control and DTR-PFD animals; upper panels are representative fluorescence microscopy images at 10× magnification; lower panel summarizes group data (n=5 control; n=6 mice Pirfenidone; 4 sections per animal analyzed). Bars represent mean. Error bars represent standard deviation. P values were calculated with the Gehan-Breslow-Wilcoxon method for panel A and with Student's T test for panels B-D.

Figure 2A:
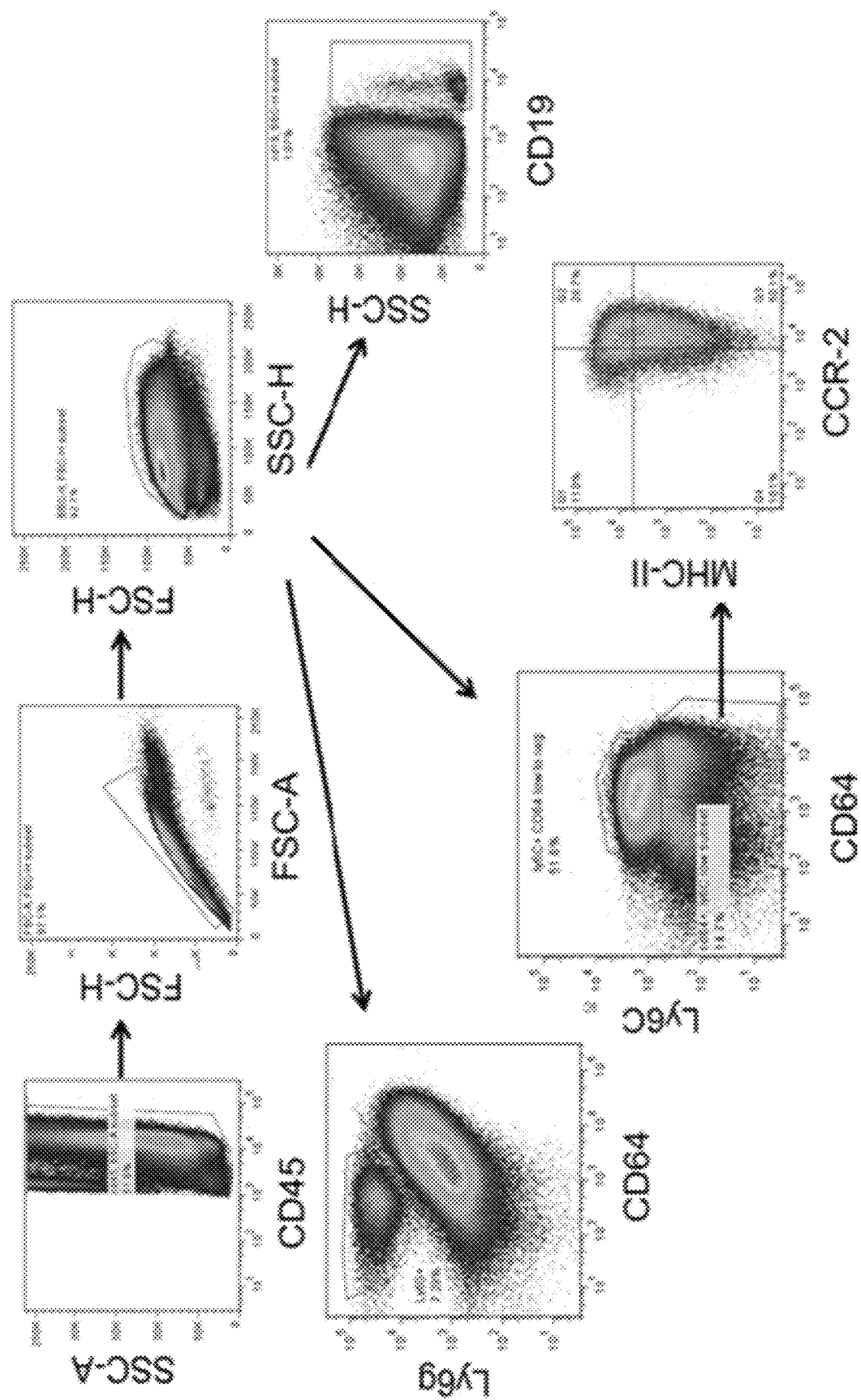
Figure 2B:
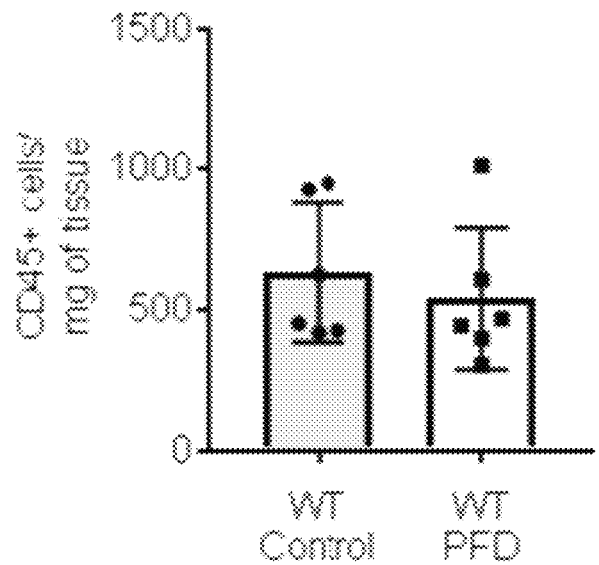
Figure 2C:
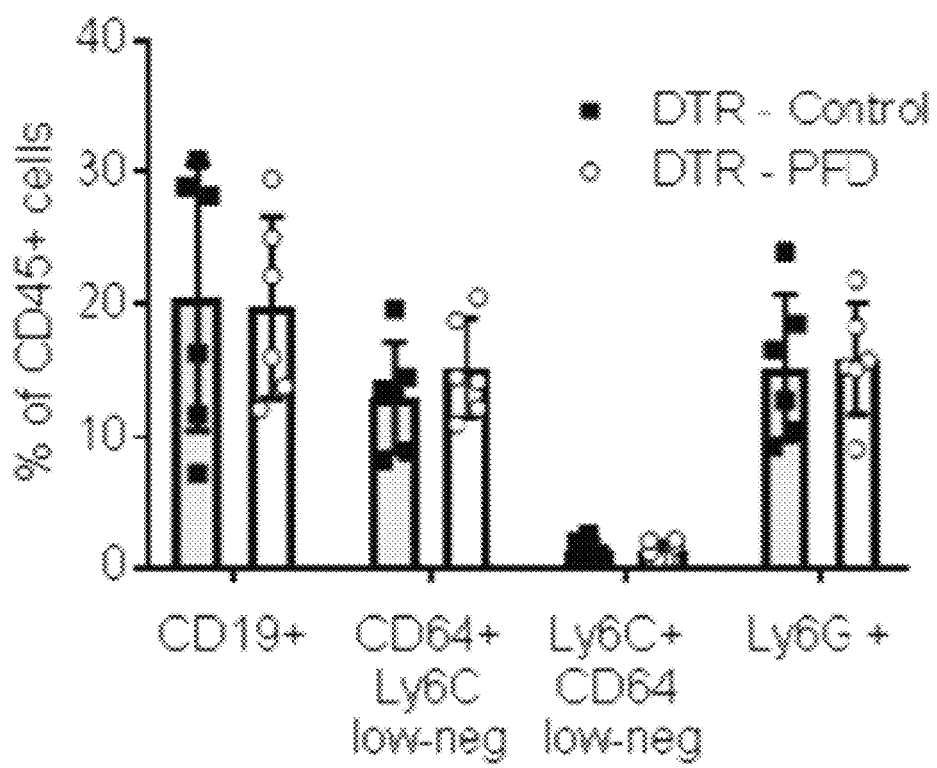
Figure 2D:
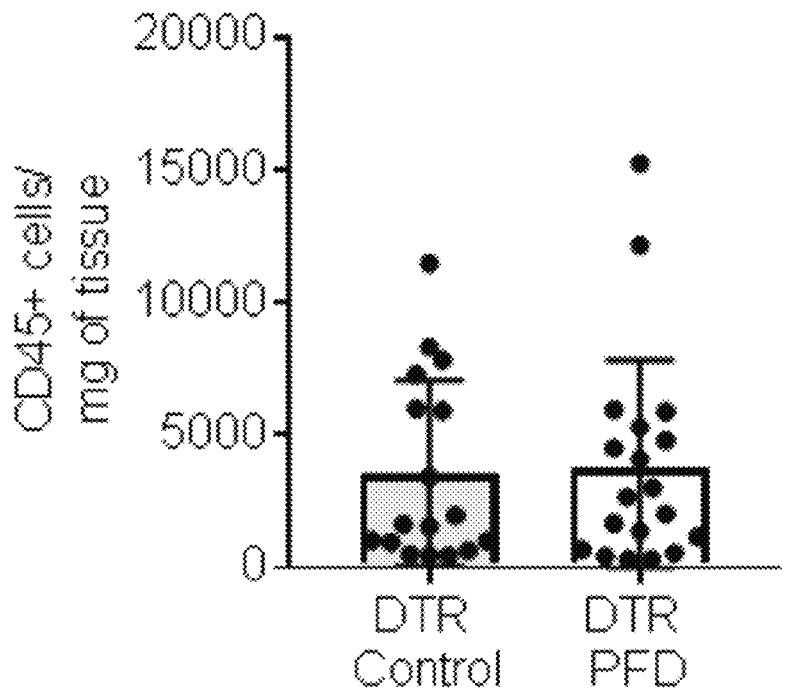
Figure 2E:
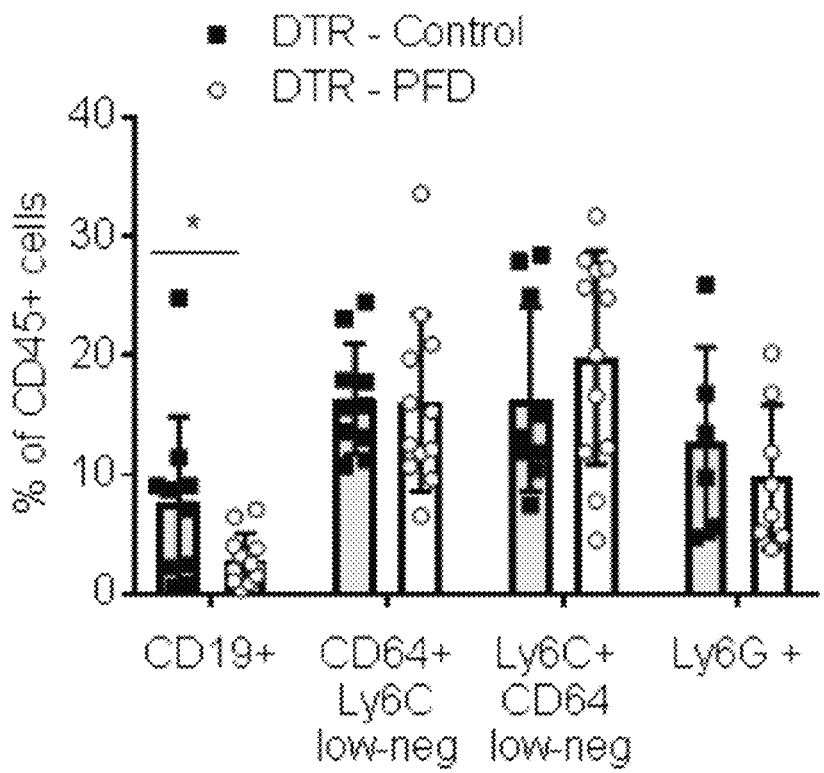
Figure 2F:
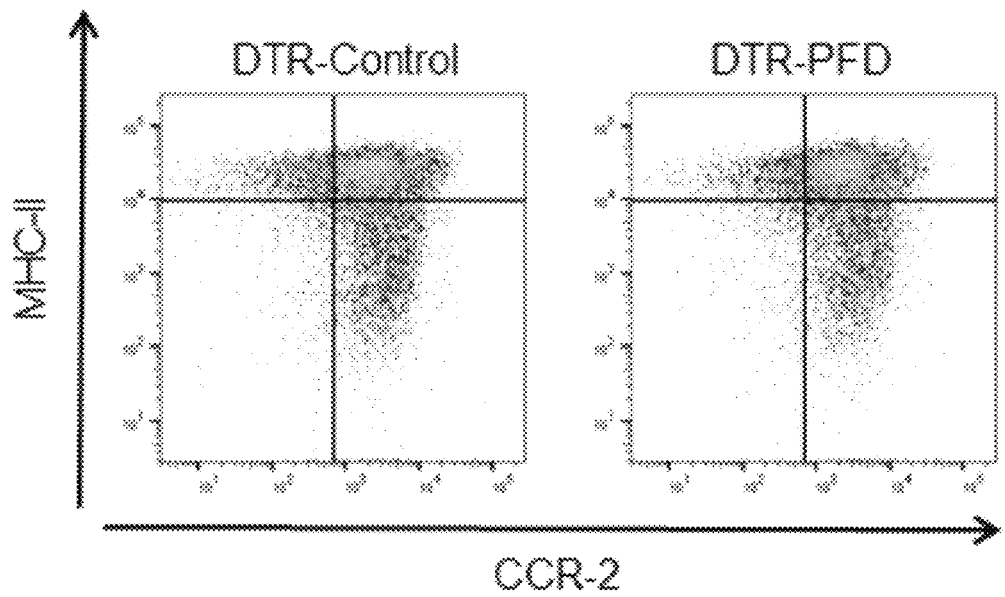
Figure 2G:
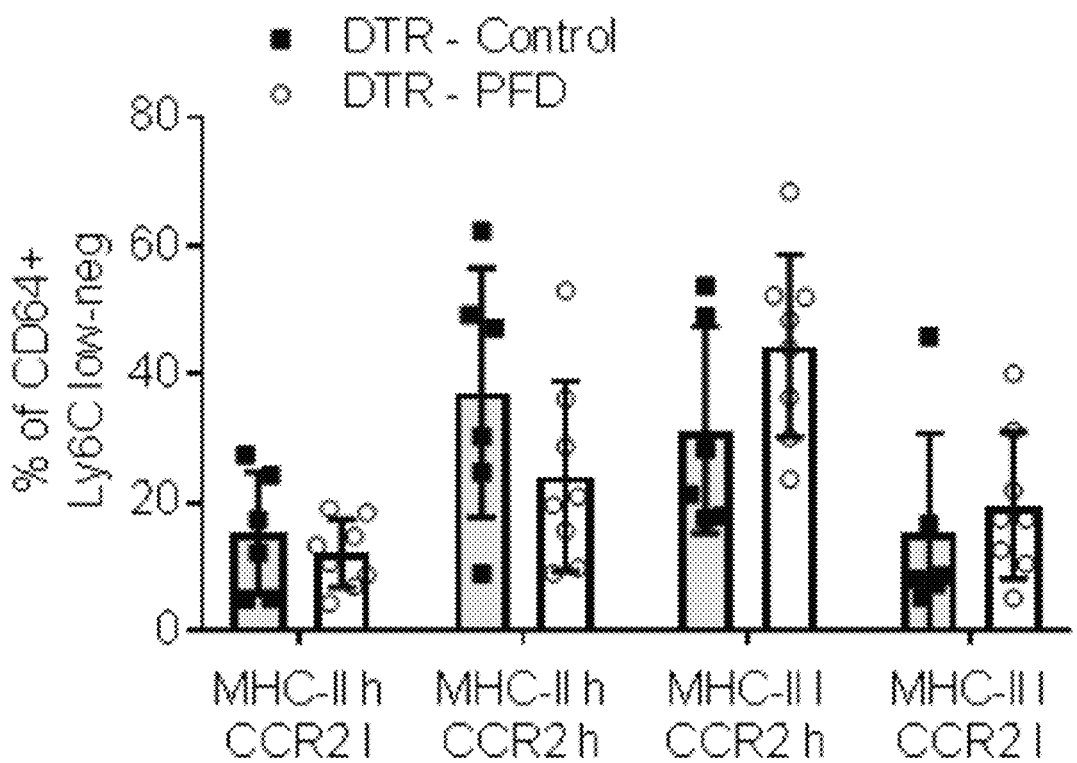

FIG. 2A, FIG. 2B, FIG. 2C, FIG. 2D, FIG. 2E, FIG. 2F and FIG. 2G depict the effect of Pirfenidone on myocardial inflammation (day 4) after DT treatment. Mice expressing the diphtheria toxin receptor (DTR) in the myocardium were exposed to diphtheria toxin and fed either chow enriched with Pirfenidone (DTR-PFD) or regular chow (DTR-control). Mice were sacrificed at day 4 post diphtheria toxin (DT) injection and the heart was collected for analysis via flow cytometry. FIG. 2A shows the gating strategy for the flow cytometric analysis used to identify the different subpopulations of myocardial CD45+ cells. FIG. 2B and FIG. 2C show wild type mice were fed either chow enriched with Pirfenidone (WT PFD) or regular chow (WT control). After 7 days, hearts were collected and analyzed via flow cytometry. n=6/group. FIG. 2D shows the total number of CD45+ cells/mg heart tissue (n=17 control, n=19 Pirfenidone). FIG. 2E shows leukocyte subsets in the myocardium (% of total: CD19+, n=14 control, n=16 Pirfenidone; Ly6g+, n=6/group, Ly6C+CD64 low/−, n=10 control, n=12 Pirfenidone; CD64+Ly6Clow/−, n=10 control, n=12 Pirfenidone). FIG. 2F shows representative FACS analysis of MHC-II and CCR-2 macrophages and monocytes. FIG. 2G shows macrophage/monocyte subsets in the myocardium as defined by expression of CCR 2, low "l" or high "h" and MHC-II expression, low "l" or high "h". % of total, n=10 control, n=12 Pirfenidone.*=p<0.05. Bars represent mean. Error bars represent standard deviation. P values were calculated with Student's T test.

Figure 3A:
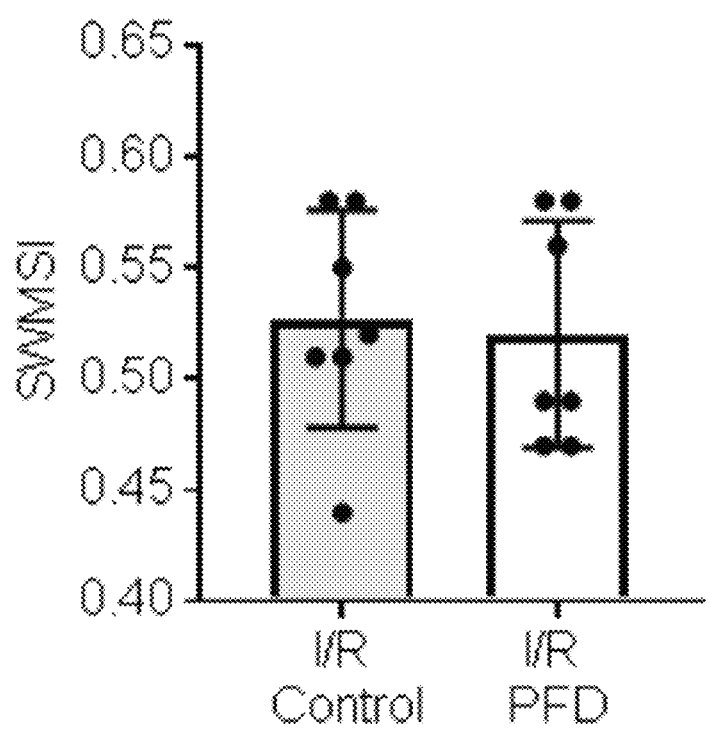
Figure 3B:
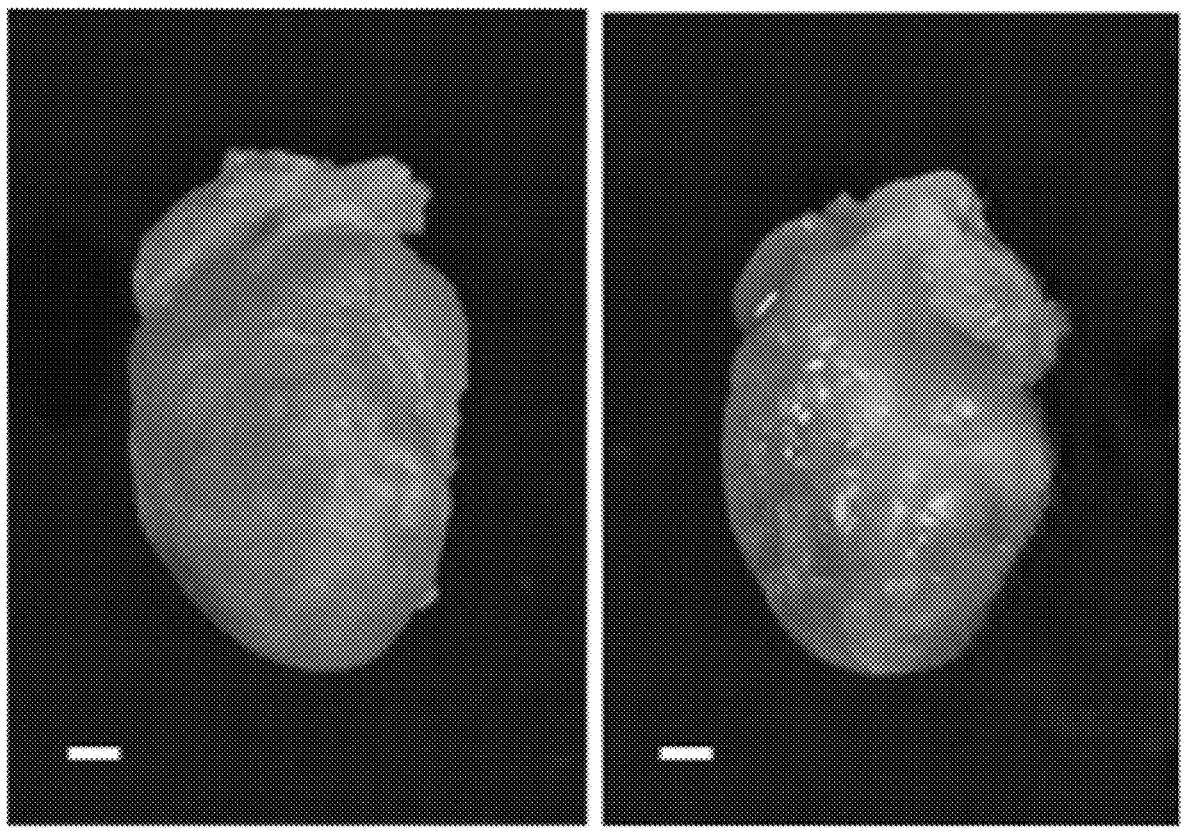
Figure 3C:
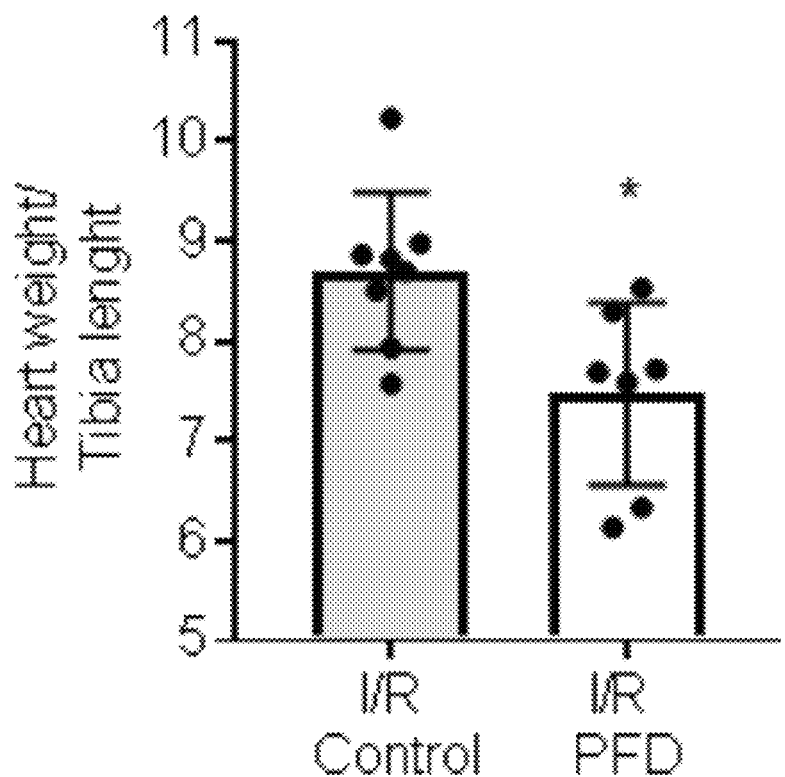
Figure 3D:
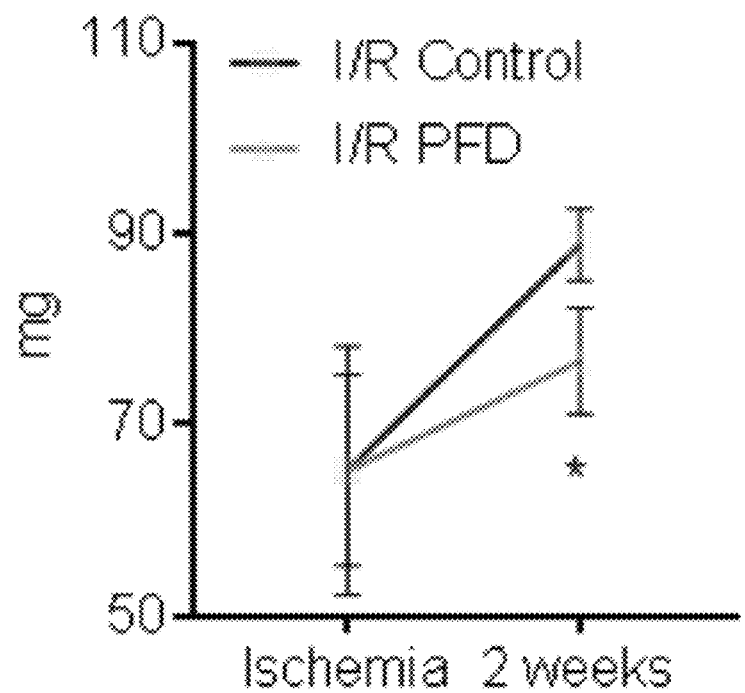
Figure 3E:
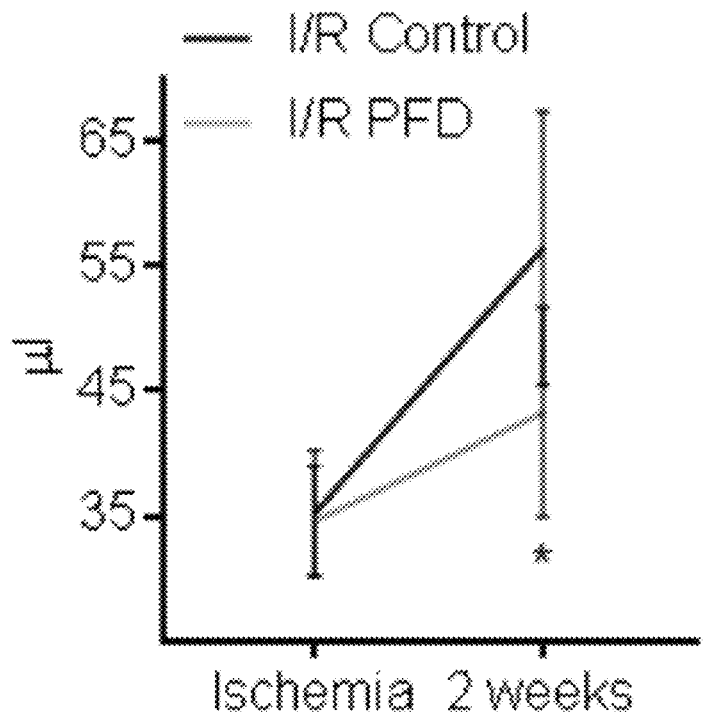
Figure 3F:
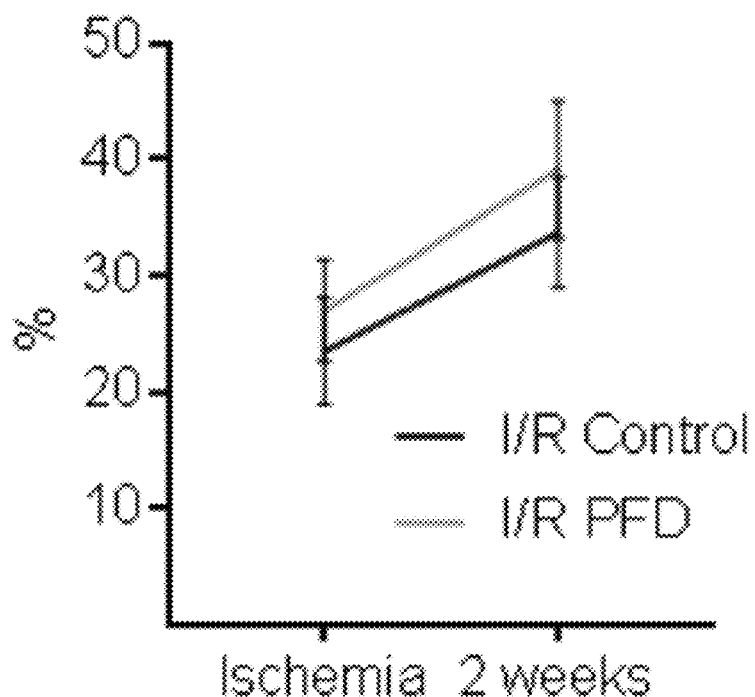
Figure 3G:
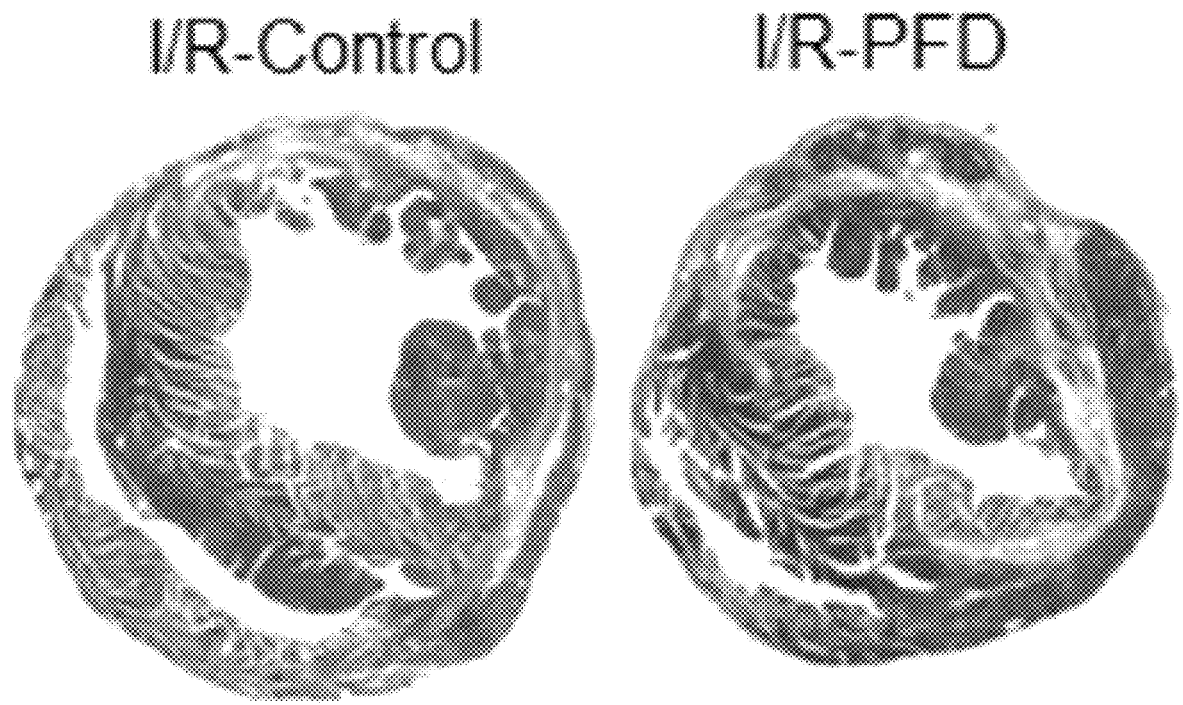

FIG. 3A, FIG. 3B, FIG. 3C, FIG. 3D, FIG. 3E, FIG. 3F, FIG. 3G and FIG. 3H show the effect of Pirfenidone on LV structure and function after closed chest I/R injury. Wild type mice were subjected to 90 minutes closed-chest ischemia reperfusion (I/R) injury. Mice were fed either chow enriched with Pirfenidone or regular chow. FIG. 3A Area at risk during closed chest-ischemia as determined by the simplified segmental wall motion score index (SWMSI) at time of ischemia. FIG. 3B Representative pictures of hearts harvested from control mice (left) and Pirfenidone treated animals (right) 2 weeks post I/R injury. Scale bar=1 mm. FIG. 3C Gravimetric analysis of hearts harvested from control mice (I/R control) and Pirfenidone treated animals (I/R-PFD). n=8 control, n=7 Pirfenidone. FIG. 3D-3F) echocardiographic assessment of myocardial function at the time of ischemia and 2 weeks after I/R injury, n=8 I/R control, n=7 I/R-PFD. FIG. 3D LV mass (LVM) by 2-D echocardiography. FIG. 3E LV end-diastolic volume (LVEDV). FIG. 3F LV ejection fraction (LVEF) FIG. 3G Representative trichrome staining of histological sections of hearts from control animals (left panel) and Pirfenidone treated animals (right panel). 1.25× magnification FIG. 3H Quantitative assessment of the % of trichrome positive staining, 2 sections analyzed per each heart. n=16 sections I/R-Control, n=14 sections I/R-PFD. *=p<0.0. Bars represent mean, error bars represent standard deviation. P values were calculated with Student's T test.

Figure 3H:
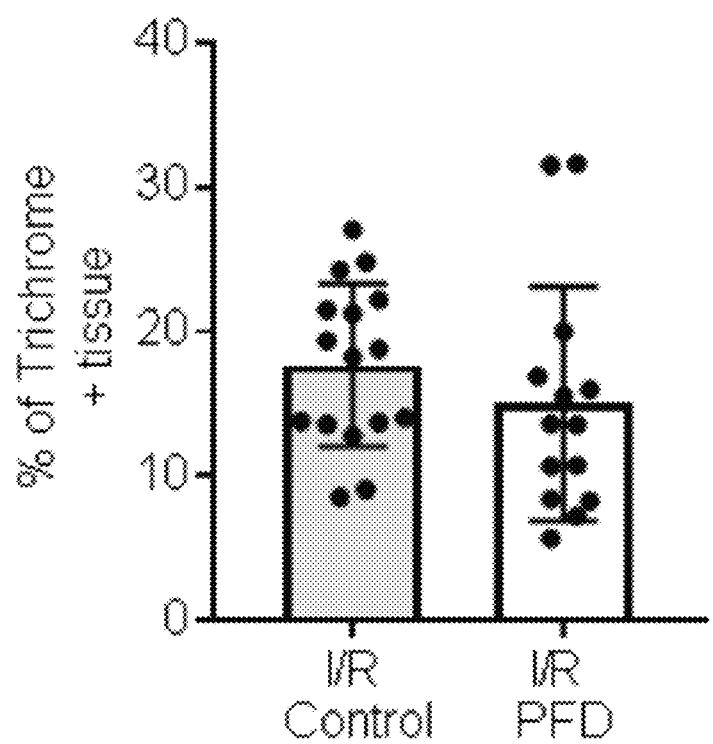
Figure 4A:
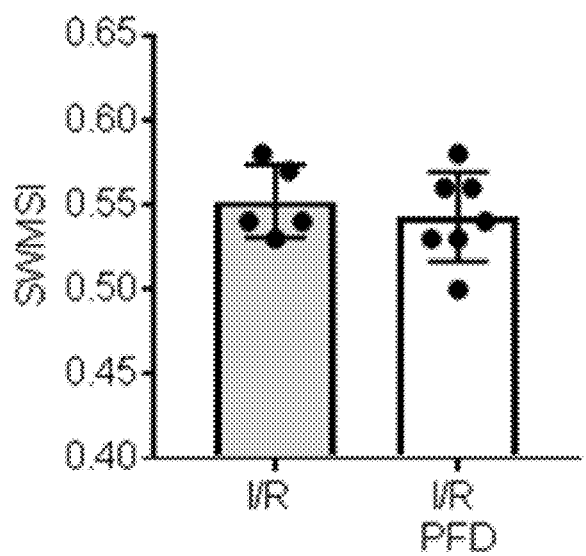
Figure 4B:
Figure 4B:
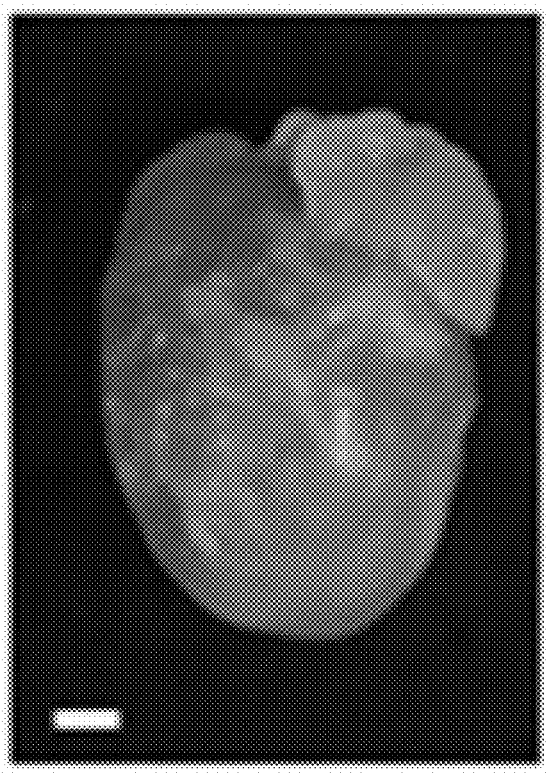
Figure 4C:
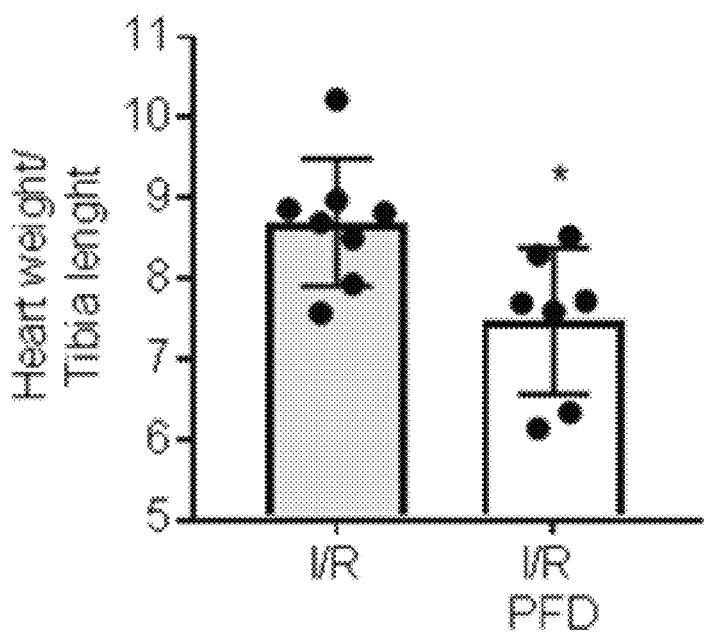
Figure 4D:
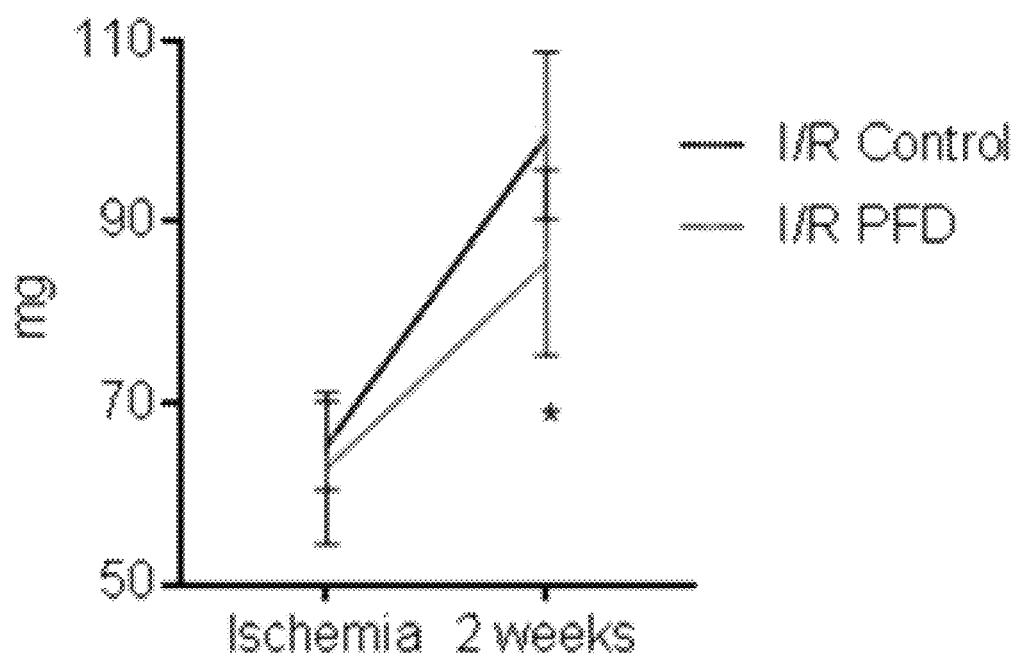
Figure 4E:
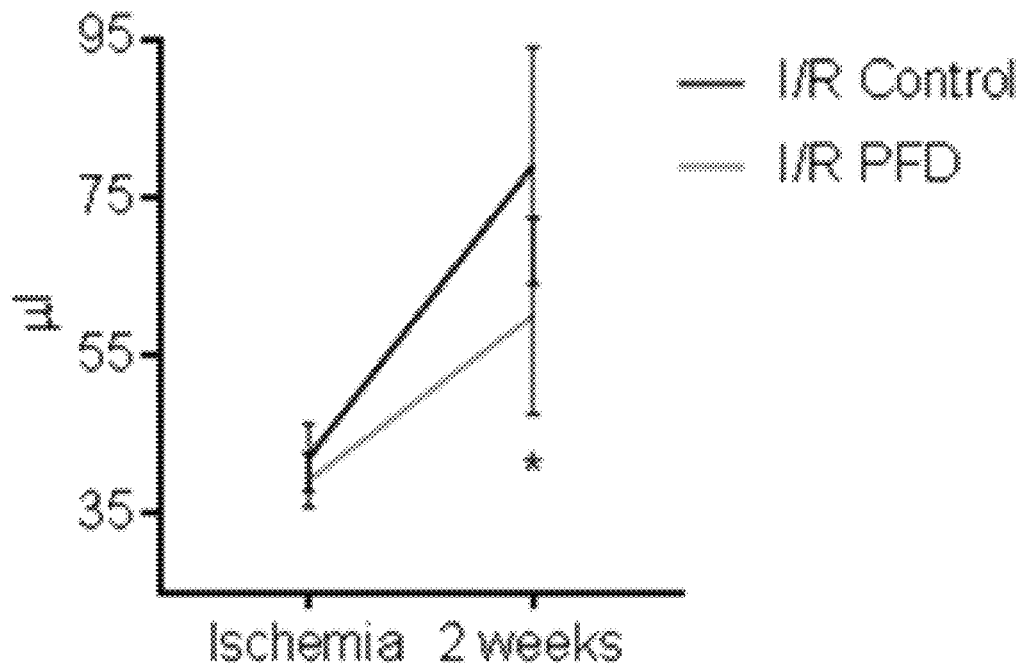
Figure 4F:
Figure 4G:
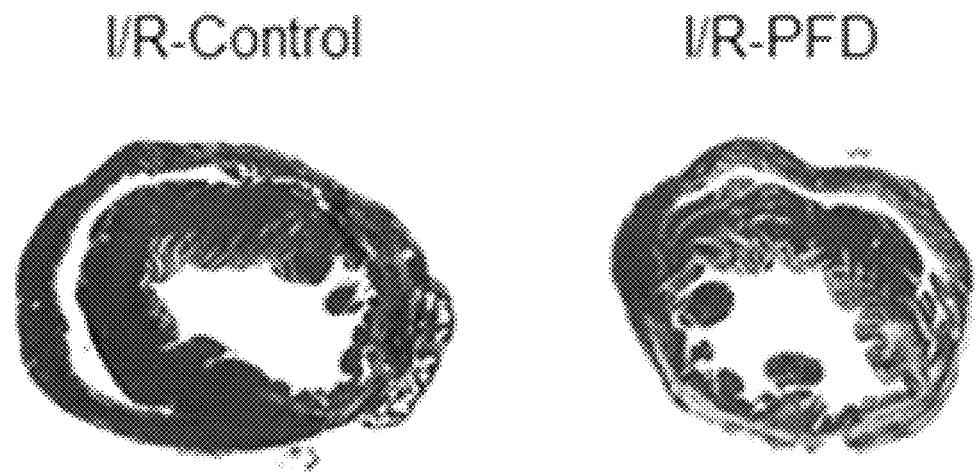
Figure 4H:
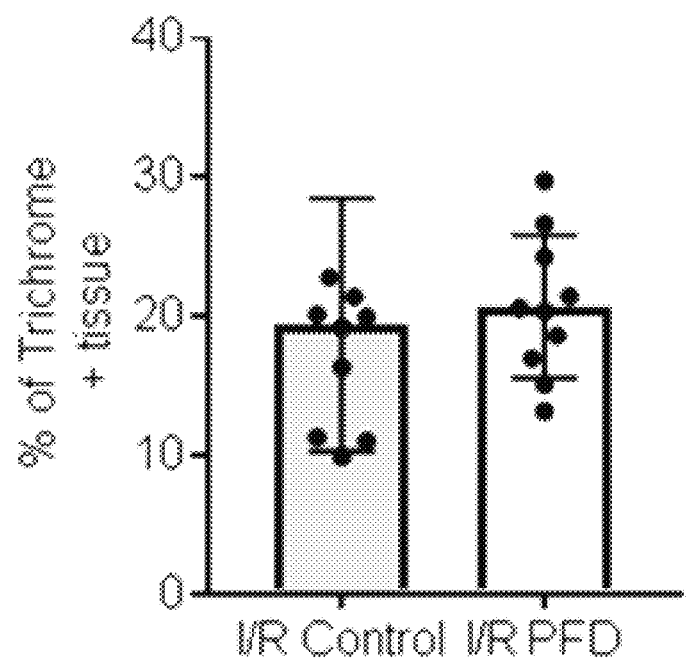

FIG. 4A, FIG. 4B, FIG. 4C, FIG. 4D, FIG. 4E, FIG. 4F, FIG. 4G, and FIG. 4H show the effects of Pirfenidone administered immediately after I/R injury and the effect of Pirfenidone on myocardial inflammation (day 4) after I/R injury. Wild type mice were subjected to 90 minutes closed-chest ischemia reperfusion (I/R) injury. Mice were fed either chow enriched with Pirfenidone or regular chow. While in the experiment reported in FIG. 3 the animals were randomized to Pirfenidone enriched diet or control diet 3 days prior to I/R injury, in this experiment mice were given Pirfenidone or vehicle intraperitoneally after I/R injury and were randomized to Pirfenidone enriched or control diet only after I/R injury. FIG. 4A Area at risk during closed chest-ischemia as determined by the simplified segmental wall motion score index (SWMSI) at time of ischemia. FIG. 4B Representative pictures of hearts harvested from control mice (left) and Pirfenidone treated animals (right) 2 weeks post I/R injury. Scale bar=1 mm. FIG. 4C Gravimetric analysis of hearts harvested from control mice (1/R control) and Pirfenidone treated animals (I/R-PFD). n=8 control, n=7 Pirfenidone. FIG. 4D-FIG. 4F) echocardiographic assessment of myocardial function at the time of ischemia and 2 weeks after I/R injury, n=5 I/R control, n=7 I/R-PFD. FIG. 4D LV mass (LVM) by 2-D echocardiography, FIG. 4E LV end-diastolic volume (LVEDV). FIG. 4F LV ejection fraction (LVEF). *=p<0.05. Bars represent average. Error bars represent standard deviation. FIG. 4G Representative trichrome staining of histological sections of hearts from control animals (left panel) and Pirfenidone treated animals (right panel). 1.25× magnification FIG. 4H Quantitative assessment of the % of trichrome positive staining, 2 sections analyzed per each heart, n=10 sections/group. *=p<0.05. Bars represent mean, error bars represent standard deviation. P values were calculated with Student's T test. Wild type mice were subjected to 90 minutes closed-chest ischemia reperfusion (I/R) injury. Mice were fed either chow enriched with Pirfenidone or regular chow. Mice were sacrificed at day 4 post I/R injury and the heart was collected for analysis via flow cytometry. n=8 I/R-Control, n=4 I/R-PFD.

Figure 5A:
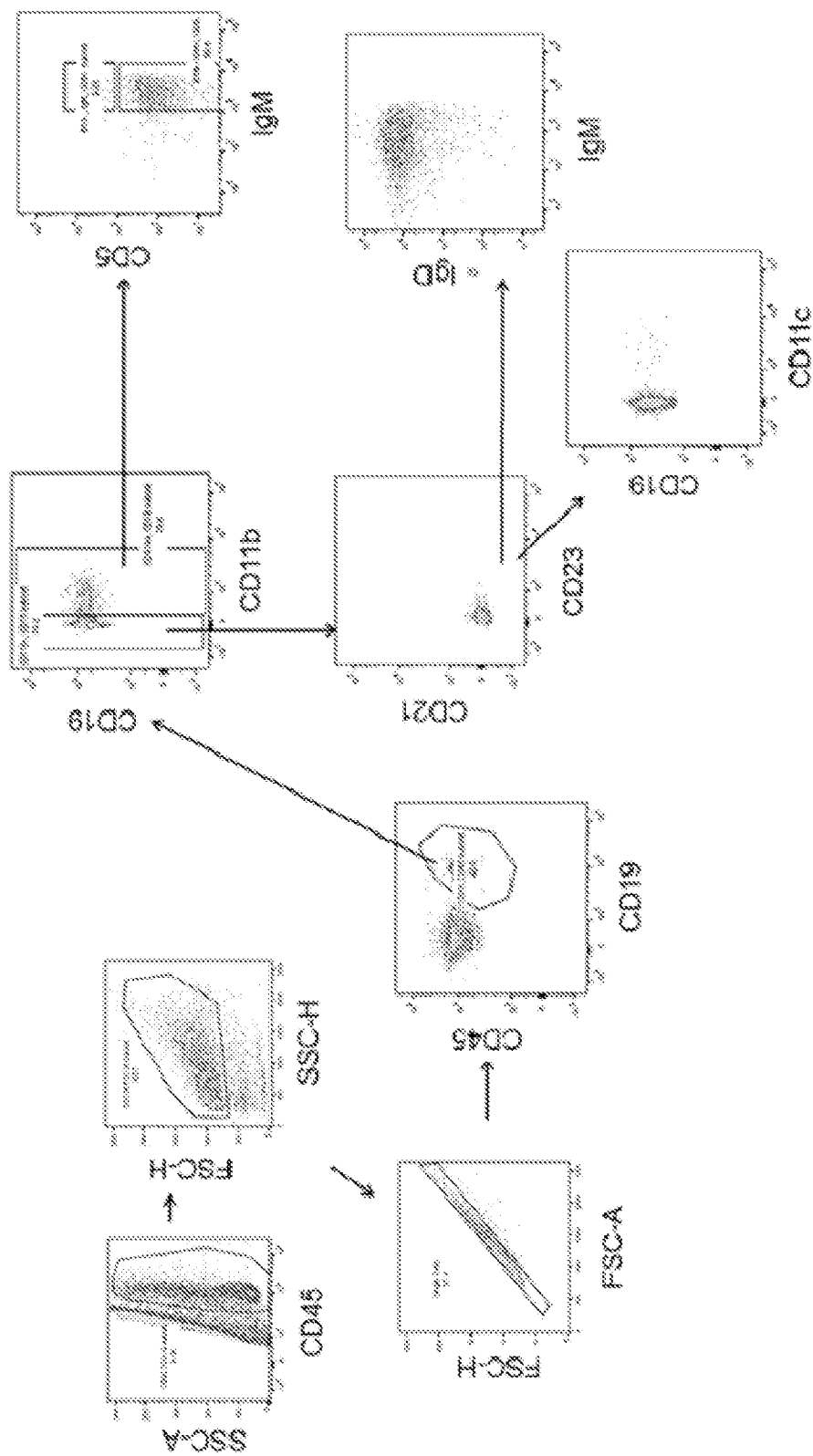
Figure 5B:
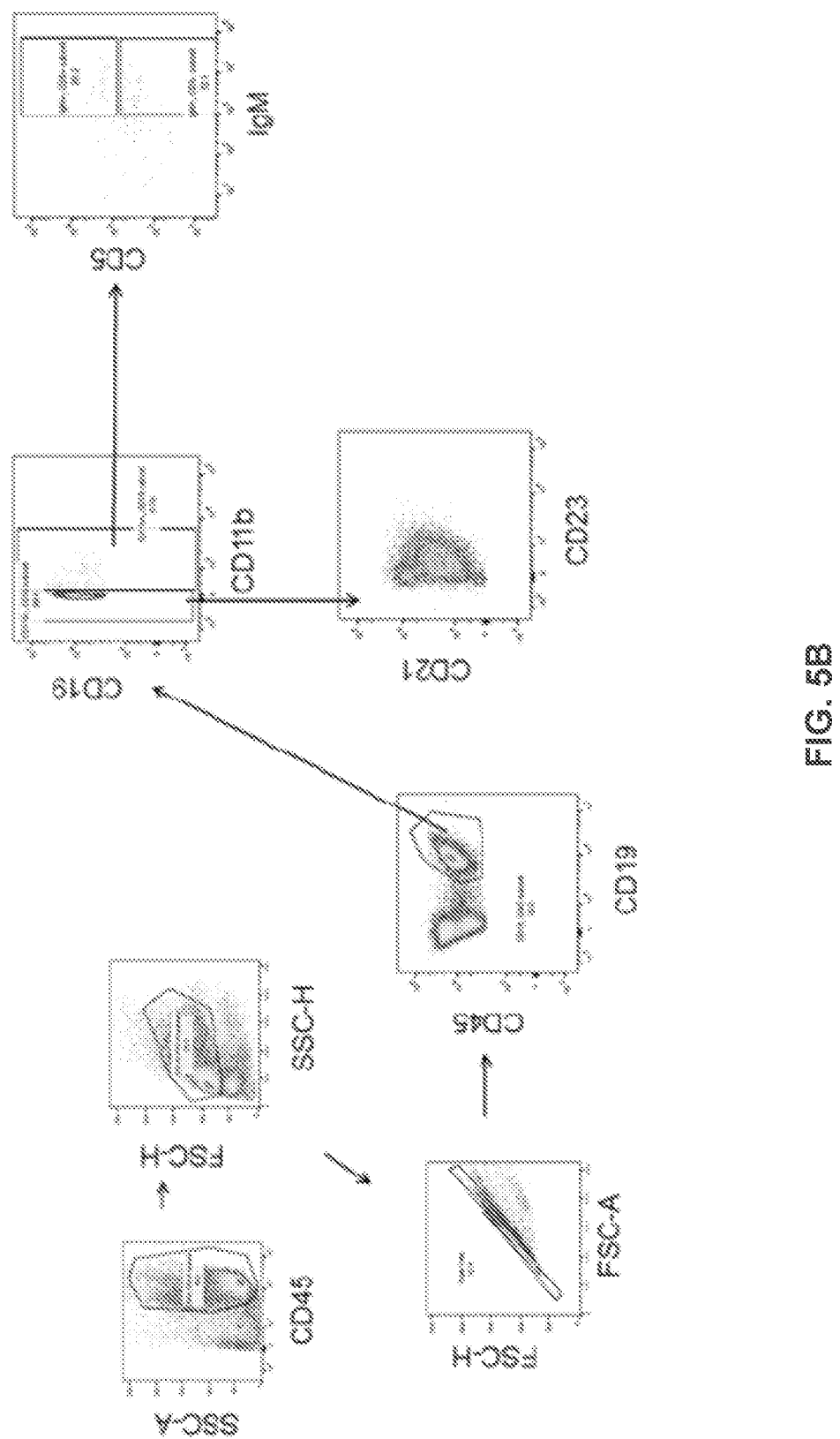
Figure 5C:
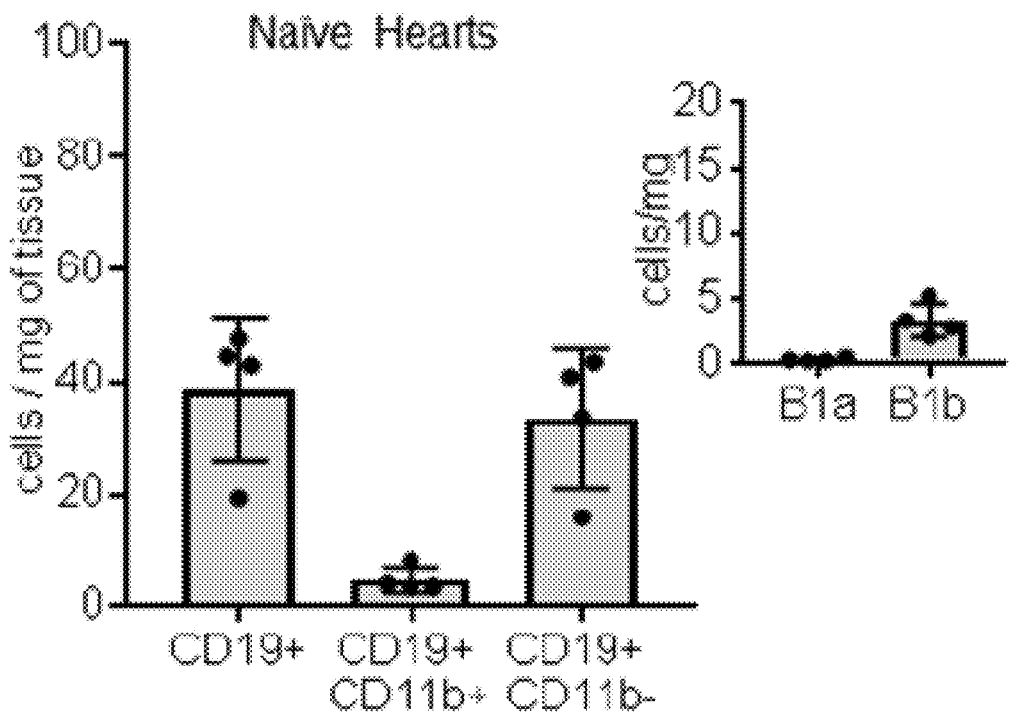
Figure 5D:
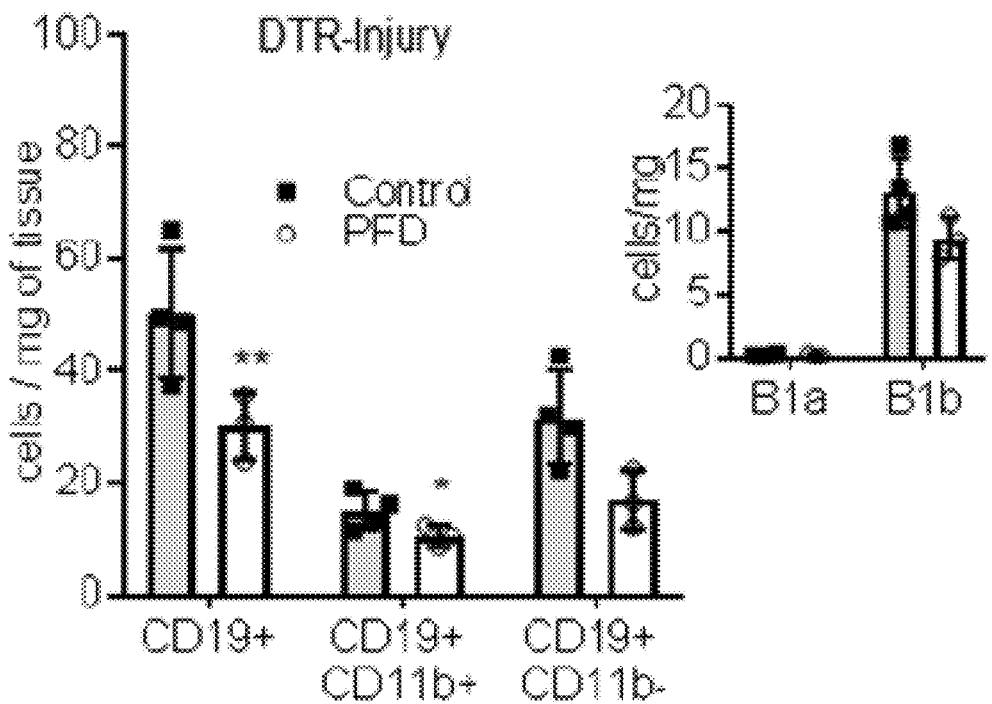
Figure 5E:
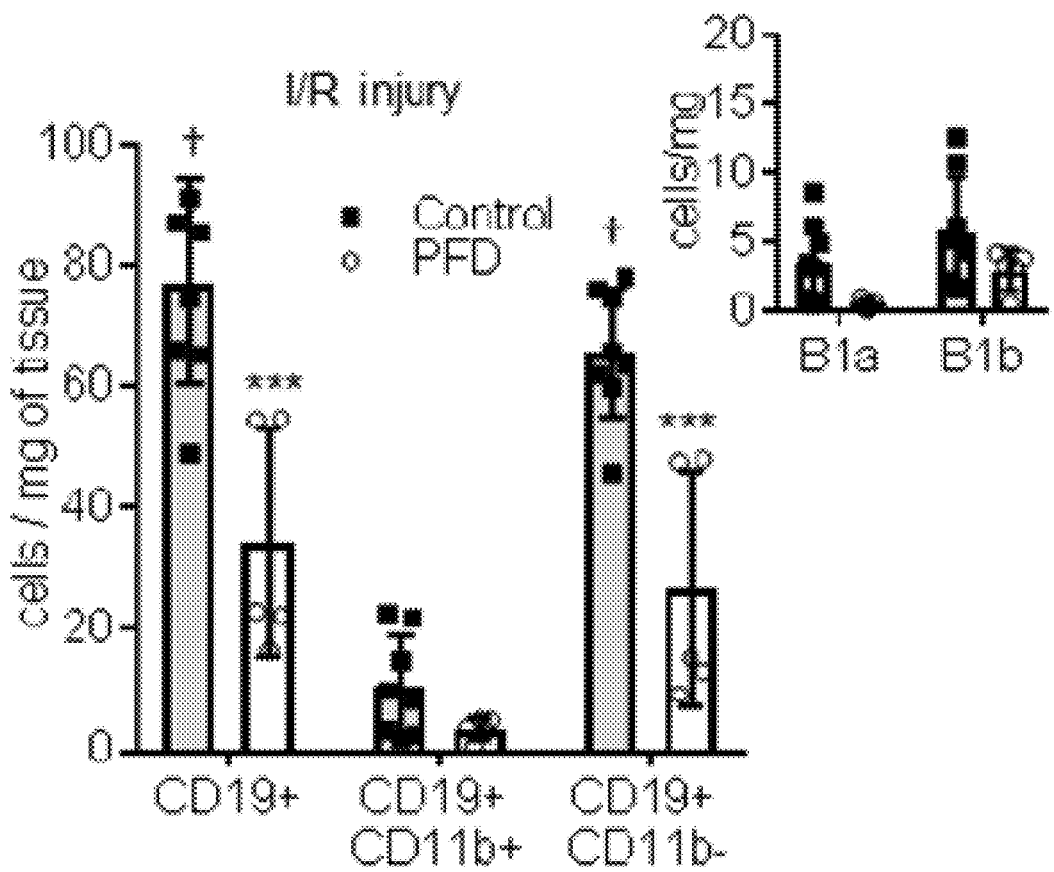

FIG. 5A, FIG. 5B, FIG. 5C, FIG. 5D, and FIG. 5E illustrates the gating strategy used to study the different subpopulations of myocardial CD19+ cells, Staining of splenic CD19+ cells and characterization of subsets of myocardial B lymphocytes at baseline and after DT-injury and I/R injury. FIG. 5A is a picture of the gating strategy used to study the different subpopulations of myocardial CD19+ cells, FIG. 5B is a picture of the Staining of splenic CD19+ cells. FIG. 5C Analysis of subsets of myocardial CD19+ B lymphocytes in naïve hearts (n=4). FIG. 5D Mice expressing the diphtheria toxin receptor (DTR) in the myocardium were exposed to diphtheria toxin and fed either regular chow (Control, grey bars) or chow enriched with Pirfenidone (PFD, white bars). Mice were sacrificed at day 4 post diphtheria toxin (DT) injection and the heart was collected for analysis of myocardial CD19+ B lymphocytes via flow cytometry. n=4 control, n=3 Pirfenidone). FIG. 5E Wild type mice were subjected to 90 minutes closed-chest ischemia reperfusion (I/R) injury. Mice were fed either regular chow (Control, grey bars) or chow enriched with Pirfenidone (PFD, white bars). Mice were sacrificed at day 4 post I/R injury and the heart was collected for analysis of myocardial CD19+ B lymphocytes via flow cytometry. (n=8 controls, n=5 Pirfenidone). *=p<0.05, =p<0.01, *=p<0.001, t p<0.001 vs naïve hearts; Bars represent mean. Error bars represent standard deviation. P values were calculated with two-way ANOVA followed by Tukey's test for multiple comparisons.

Figure 6A:
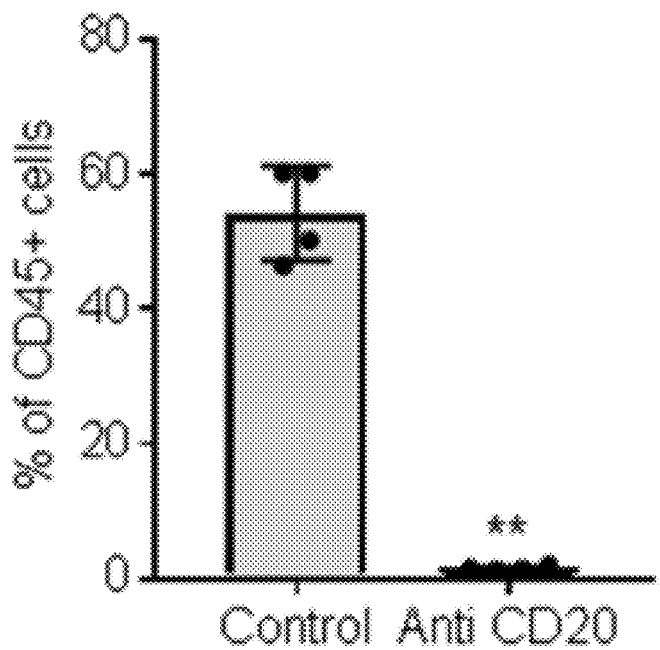
Figure 6B:
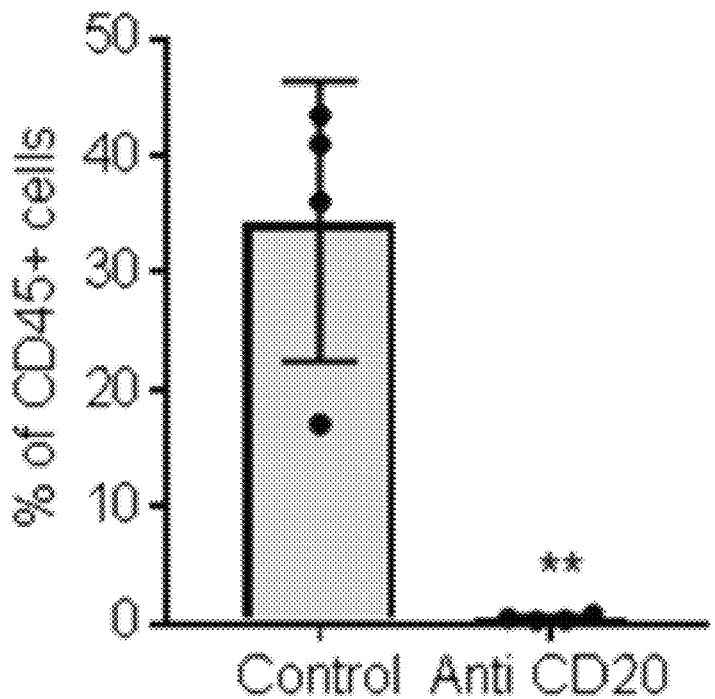
Figure 6C:
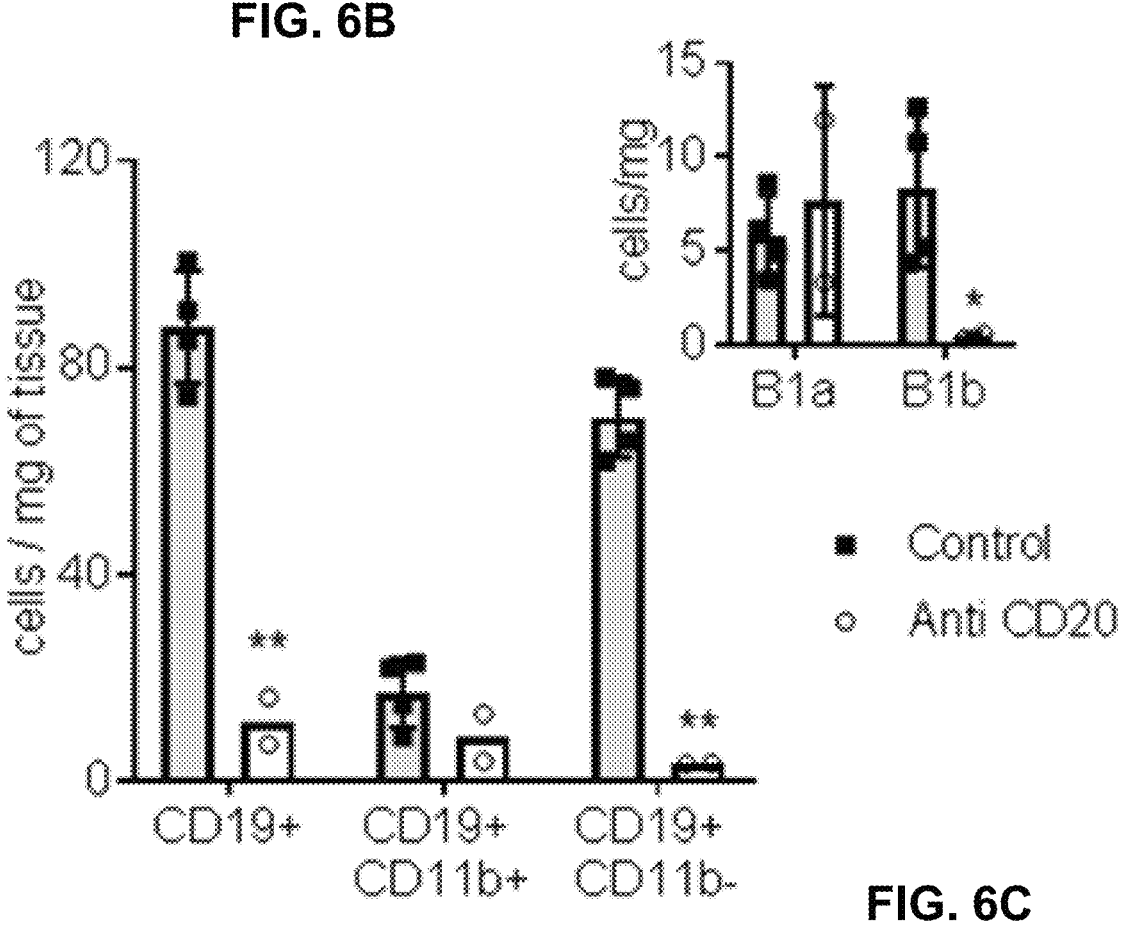
Figure 6D:
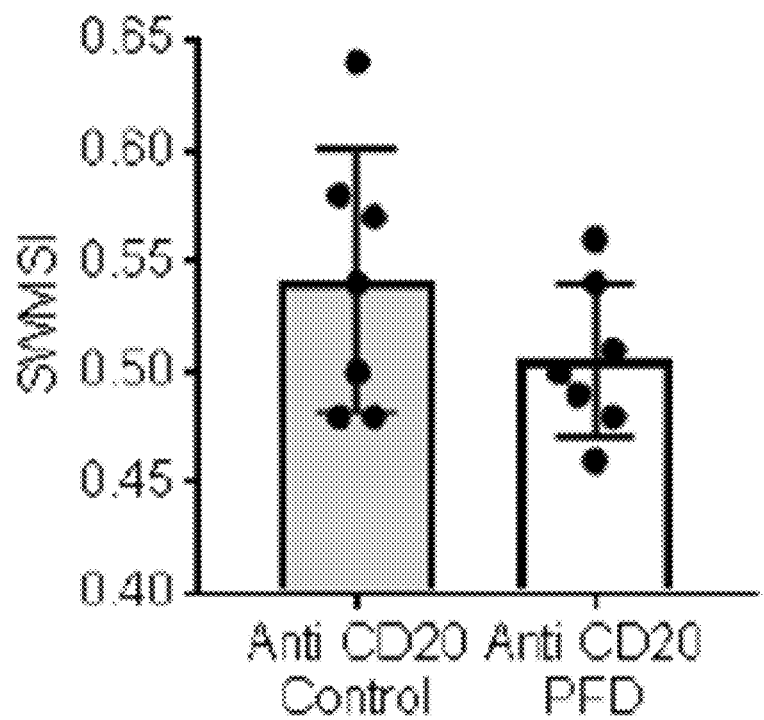
Figure 6E:
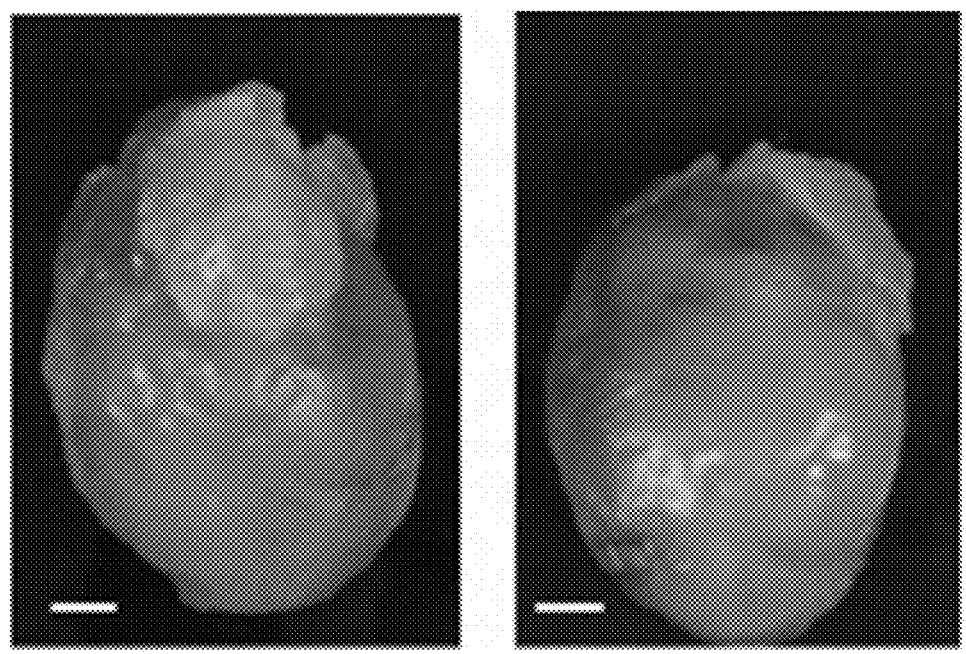
Figure 6F:
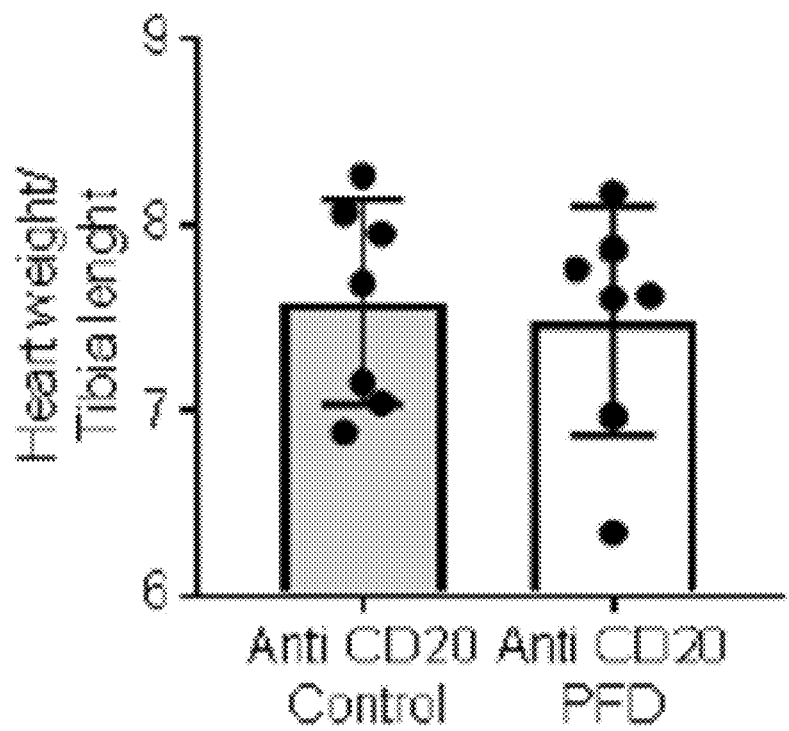
Figure 6G:
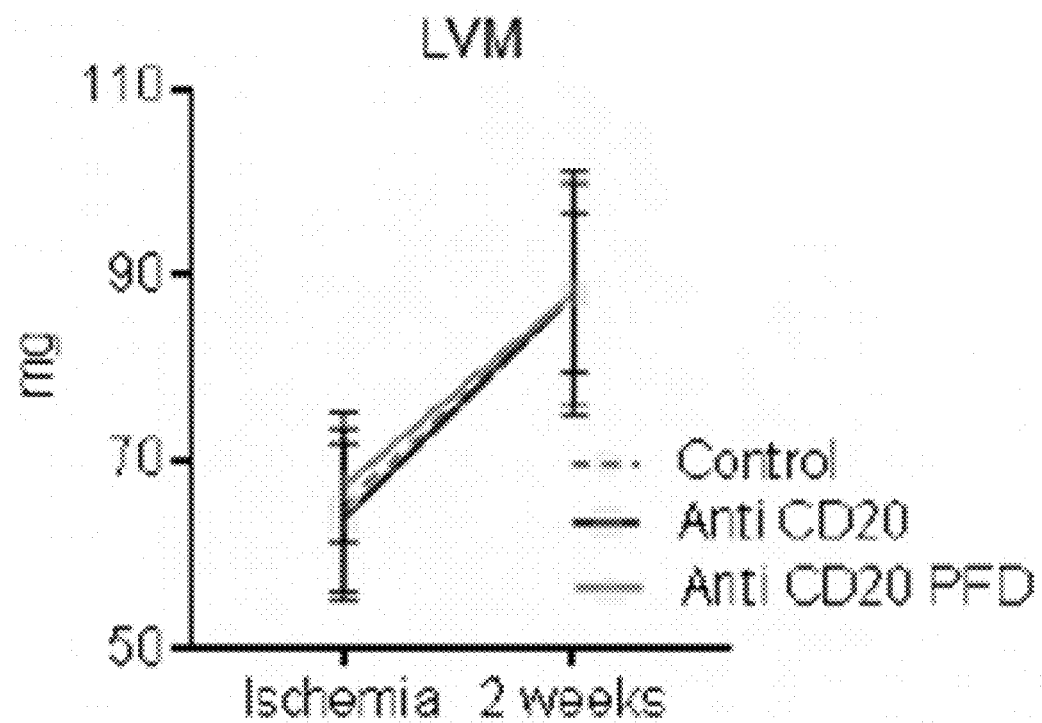
Figure 6H:
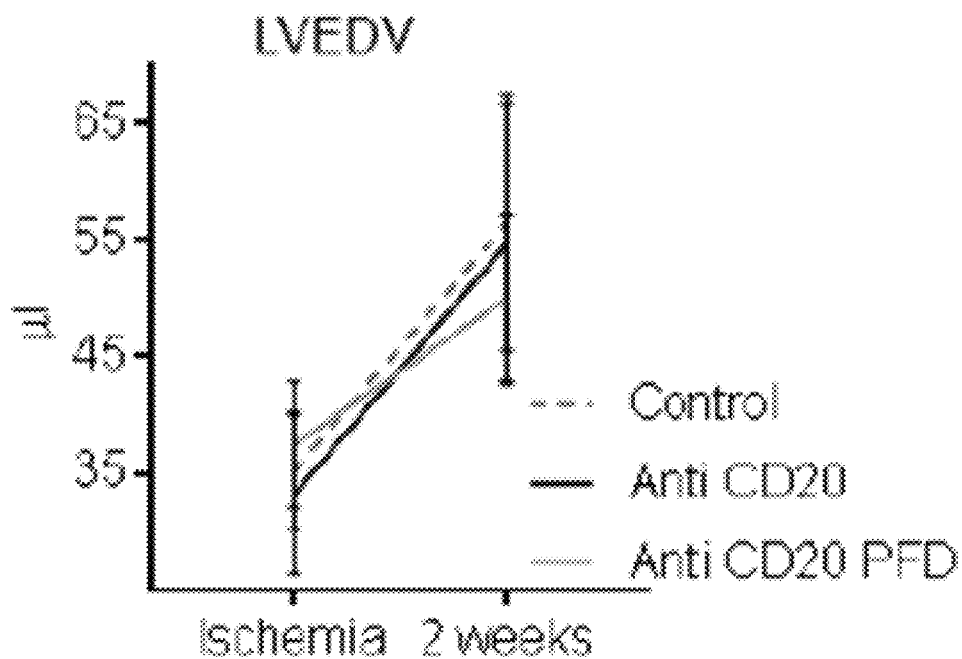
Figure 6I:
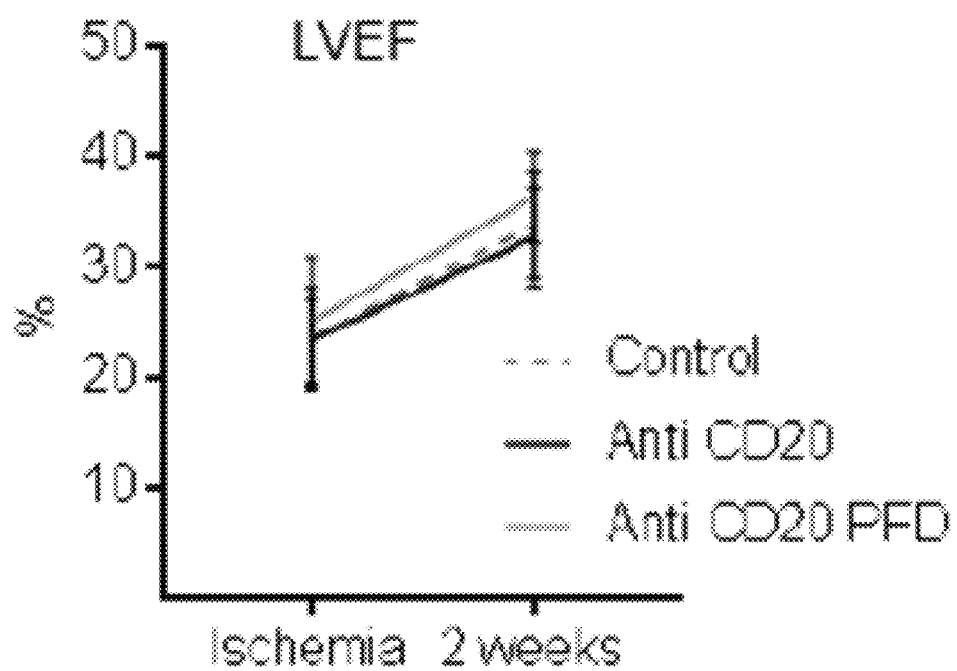
Figure 6J:
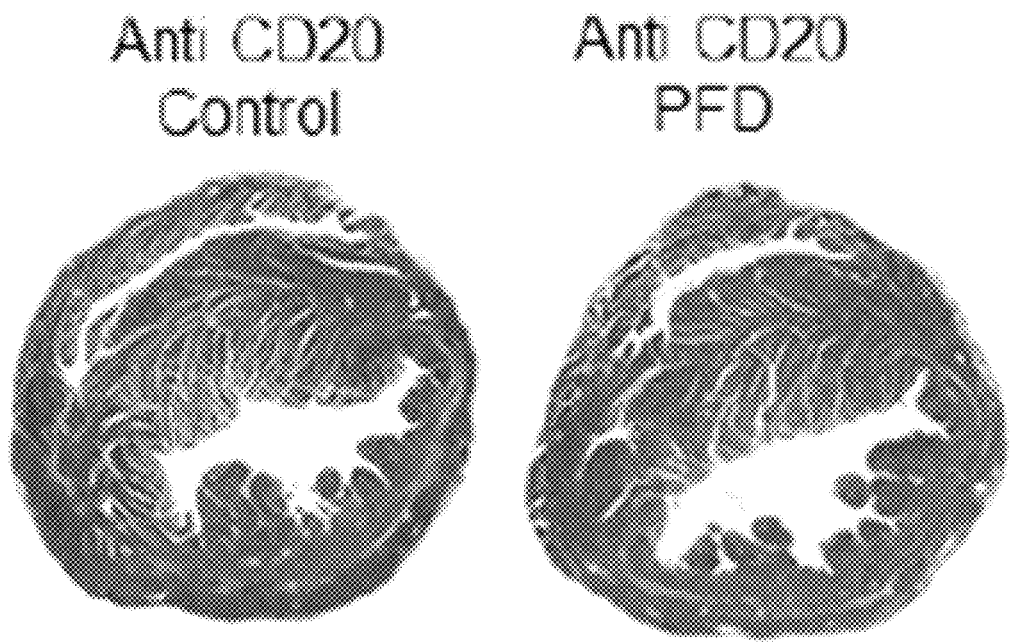
Figure 6K:
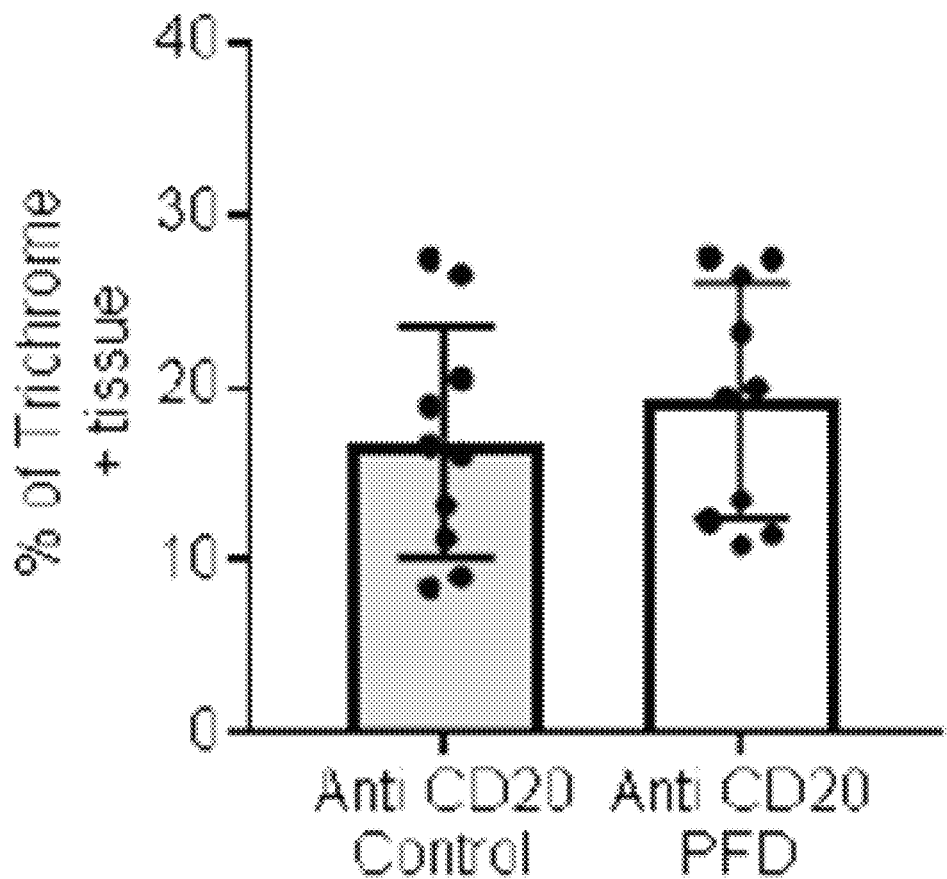

FIG. 6A, FIG. 6B, FIG. 6C, FIG. 6D, FIG. 6E, FIG. 6F, FIG. 6G, FIG. 6H, FIG. 6I, FIG. 6J and FIG. 6K show B cell depletion with anti-CD20 antibody and the effect of B cell depletion on Pirfenidone cardioprotective effect after I/R injury. FIG. 6D-FIG. 6K) Mice were injected with Anti-CD20 antibody (Anti CD20) or isotype control (Control). 7 days after injection the spleen (FIG. 6A, n=3/group) and the heart (FIG. 6I, n=3 group) were collected and analyzed via flow cytometry. FIG. 6C Mice were injected with Anti-CD20 antibody or isotype control (Control). On day 7 post injection, mice were subjected to closed chest ischemia-reperfusion injury. On day 4 post ischemia-reperfuion injury the animals were sacrificed and the myocardium was analyzed via flow cytometry. n=2 Anti CD20, n=3 Control. Bars represent average, error bars represent standard deviation. Wild type mice were B cell depleted via injection of anti-CD20 antibody. 7 days after injection of anti-CD20 antibody, B cells depleted mice were subjected to 90 minutes closed-chest ischemia reperfusion (I/R) injury. Mice were fed either chow enriched with Pirfenidone (Anti CD20 PFD) or regular chow (Anti CD20 Control). FIG. 6D Area at risk during closed chest-ischemia as determined by the simplified segmental wall motion score index (SWMSI) at time of ischemia. FIG. 6E Representative pictures of hearts harvested from anti-CD20 treated mice (left) and anti-CD20+ Pirfenidone treated animals (right). Scale bar=1 mm. FIG. 6F Gravimetric analysis of hearts harvested Pirfenidone treated animals (Anti CD20 PFD) and untreated controls (Anti CD20 Control), n=7/group. FIG. 6G-FIG. 6H) Echocardiographic assessment of myocardial function at the time of ischemia and 2 weeks after I/R injury, n=7/group. Data from non-anti-CD20 treated animals already reported in prior figures is shown again for comparison only (Control) FIG. 6G LV mass (LVM) by 2-D echocardiography FIG. 6H LV end-diastolic volume (LVEDV) F) LV ejection fraction (LVEF). FIG. 6J Representative trichrome staining of histological sections of hearts from control animals (left panel) and Pirfenidone treated animals (right panel). 1.25× magnification FIG. 6K Quantitative assessment of the % of trichrome positive staining, 2 sections analyzed per each heart, n=10 sections/group. *=p<0.05. Bars represent mean, error bars represent standard deviation. P values were calculated with Student's T test.

Figure 7A:
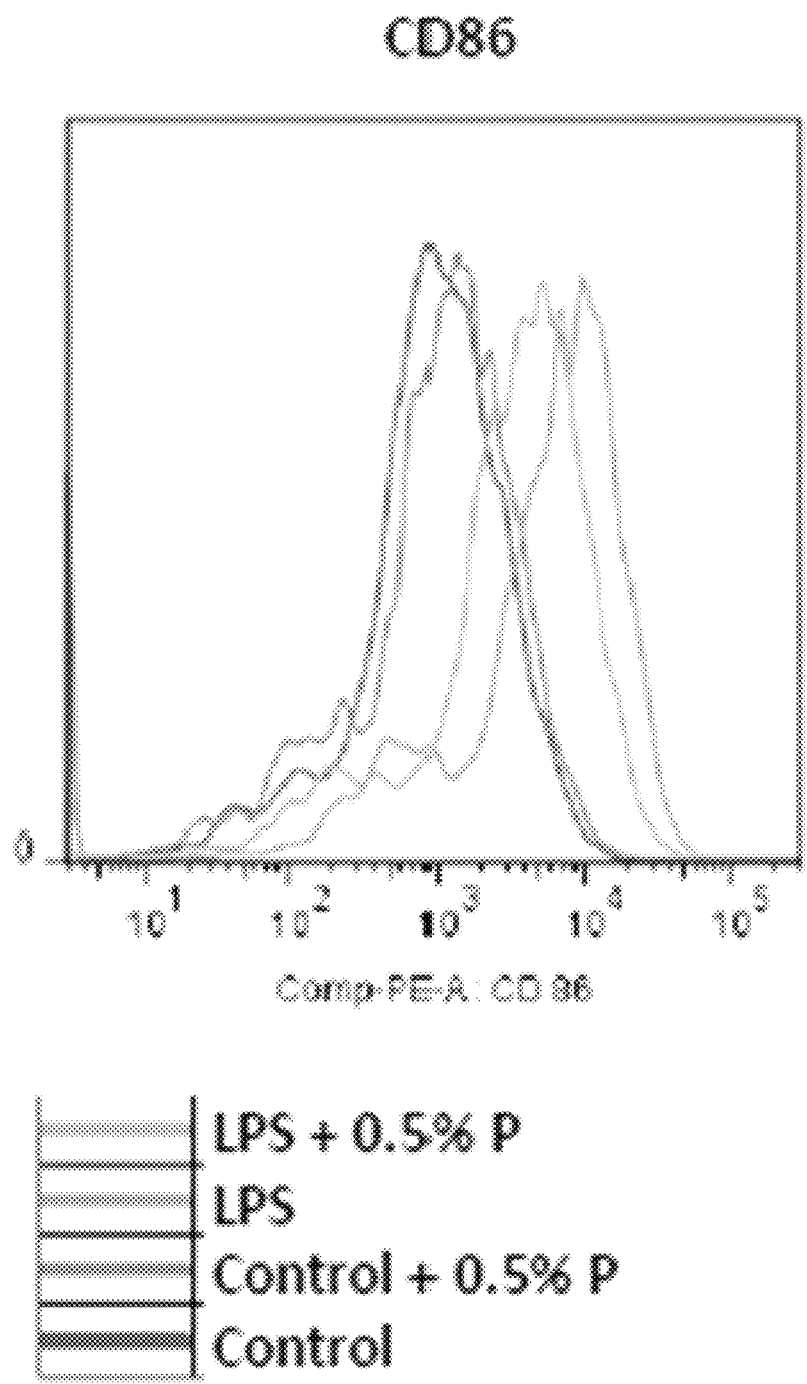
Figure 7B:
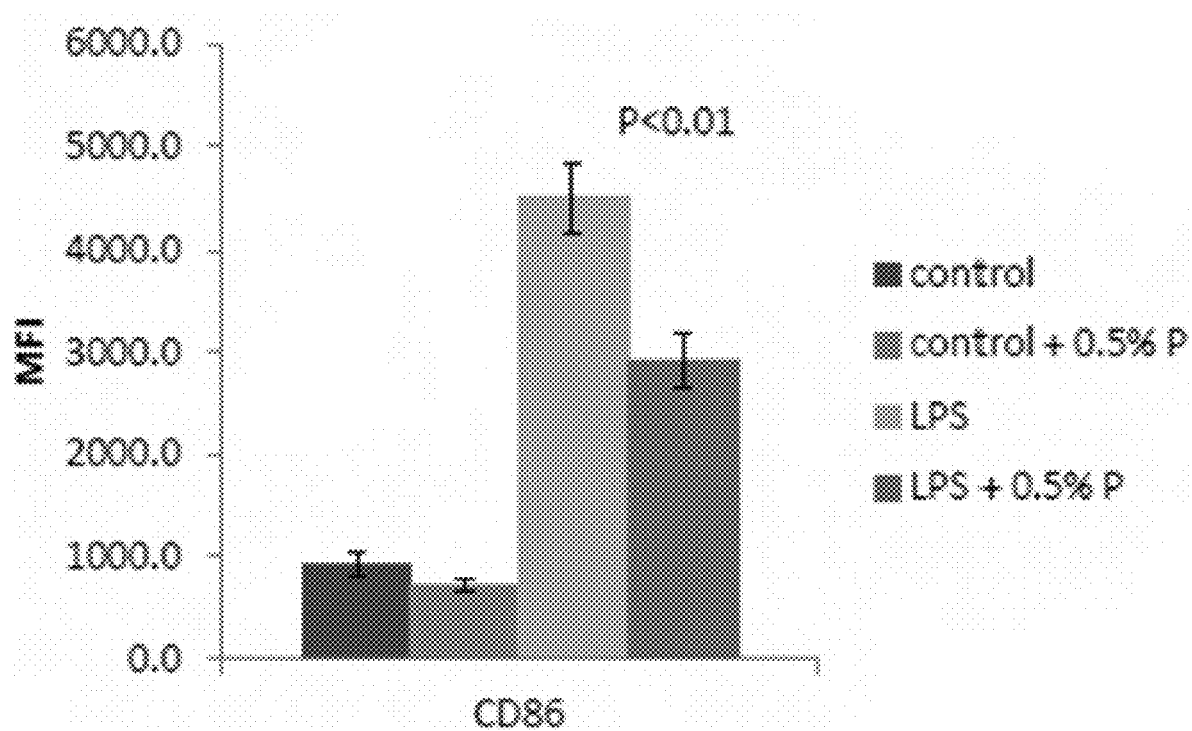

FIG. 7A and FIG. 7B illustrate by mean fluorescence intensity peaks (FIG. 7A) and graph (FIG. 7B) that in cultures of peritoneal derived inflammatory cells, pirfenidone prevents LPS induced upregulation of CD86 in CD19+ cells.

Figure 8A:
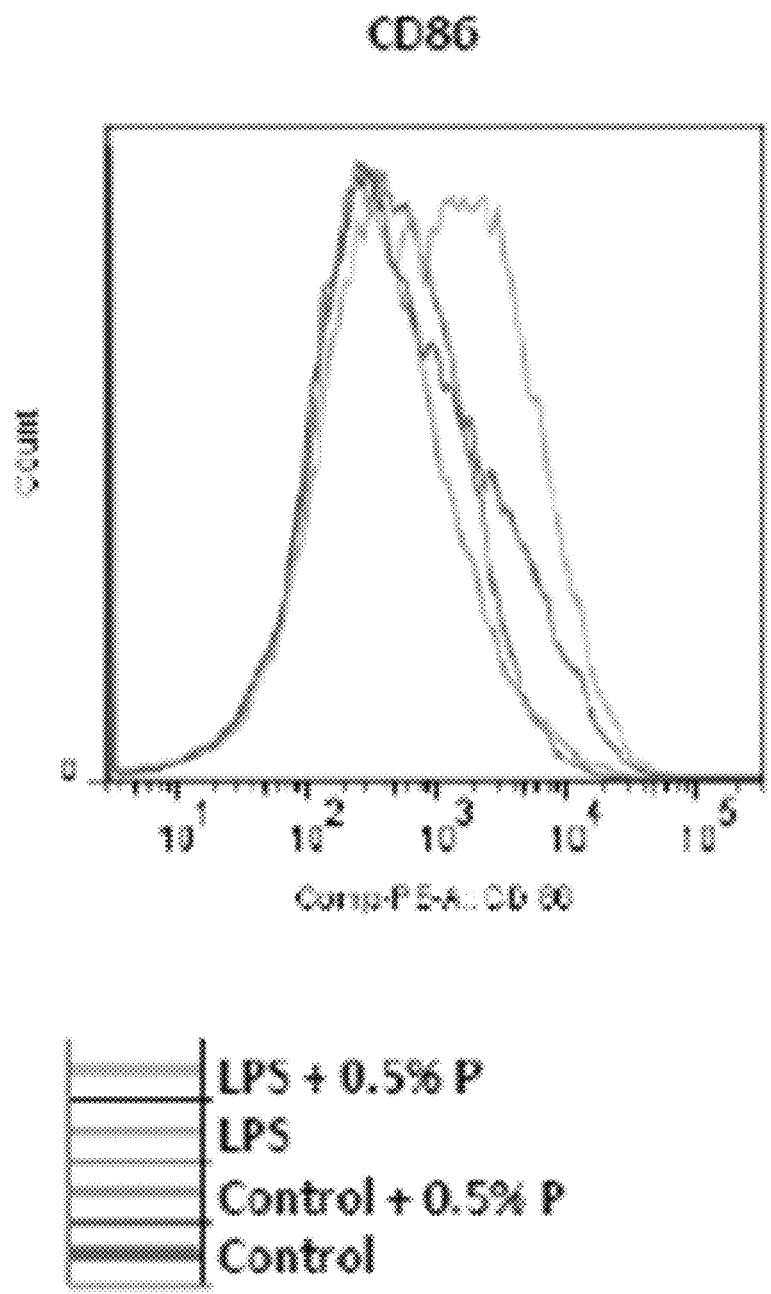
Figure 8B:
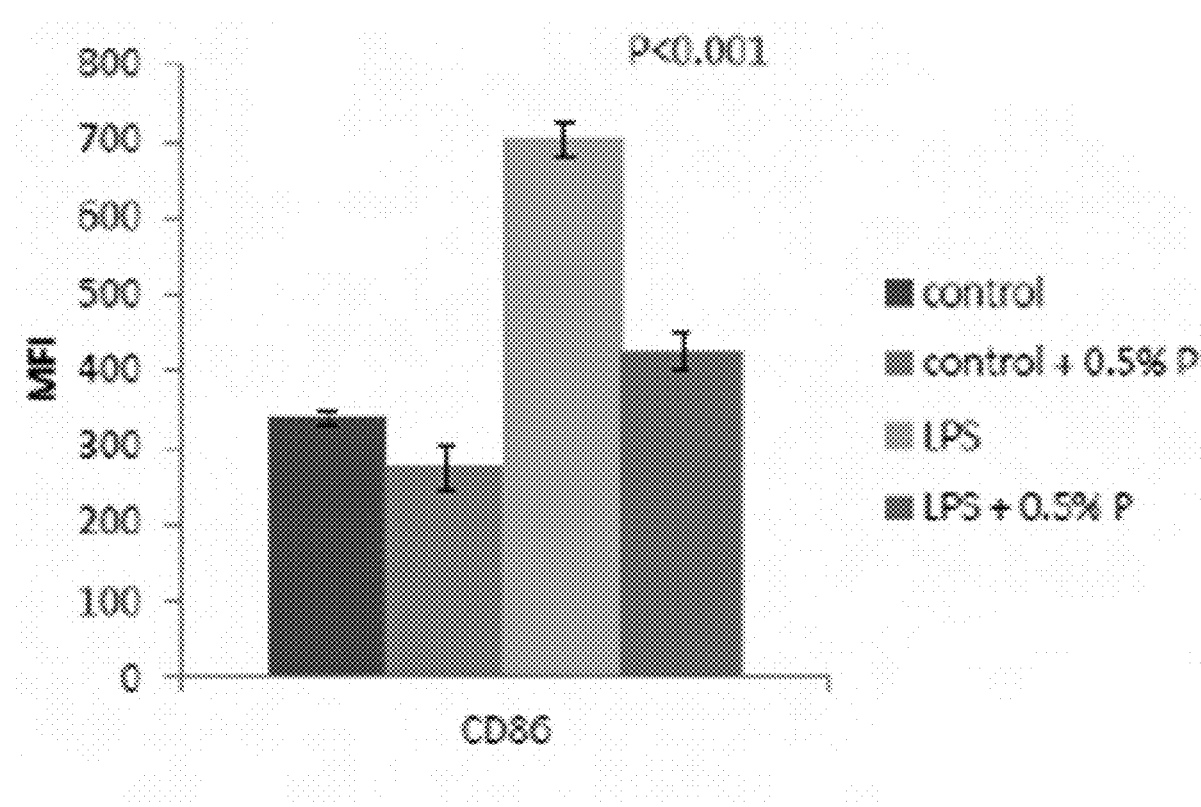

FIG. 8A and FIG. 8B illustrate by mean fluorescence intensity peaks (FIG. 8A) and graph (FIG. 8B) that in cultures of spleen derived CD19+ cells, pirfenidone prevents LPS induced upregulation of CD86 in CD19+ cells.

Figure 9A:
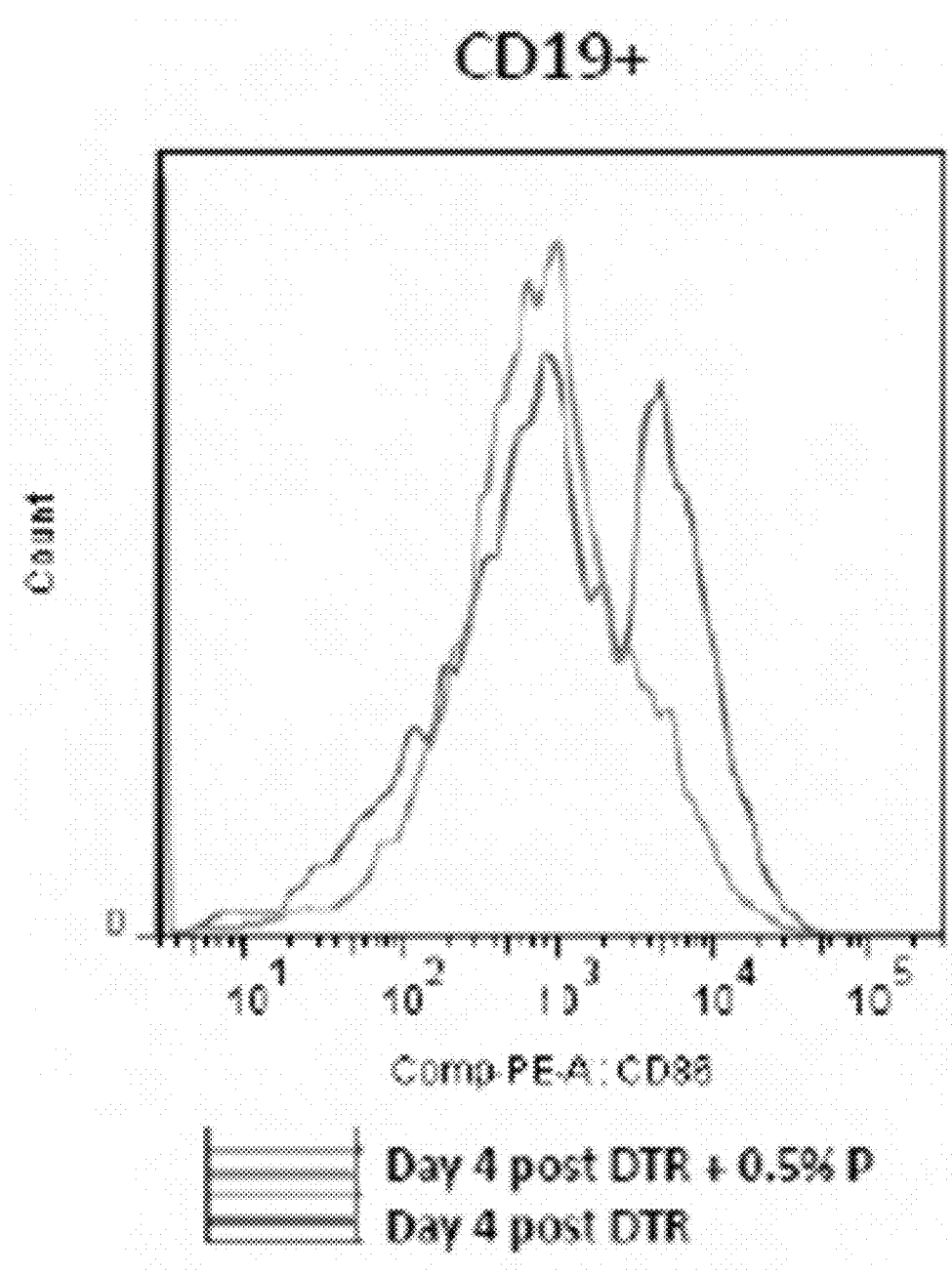
Figure 9B:
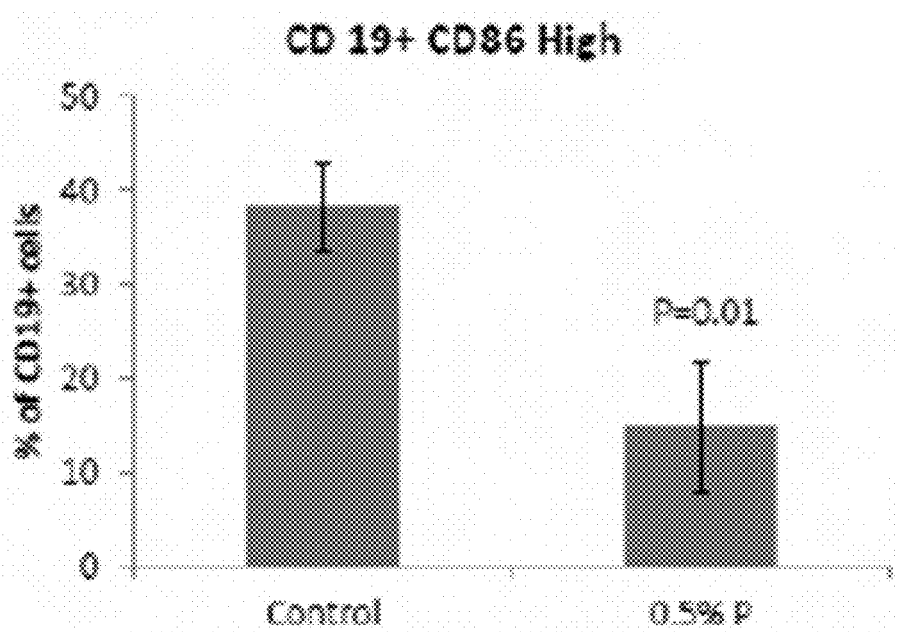

FIG. 9A and FIG. 9B illustrate by mean fluorescence intensity peaks (FIG. 9A) and graph (FIG. 9B) that pirfenidone reduces upregulation of CD86 on CD19+ cells in vivo in DTR treated mice.

Figure 10A:
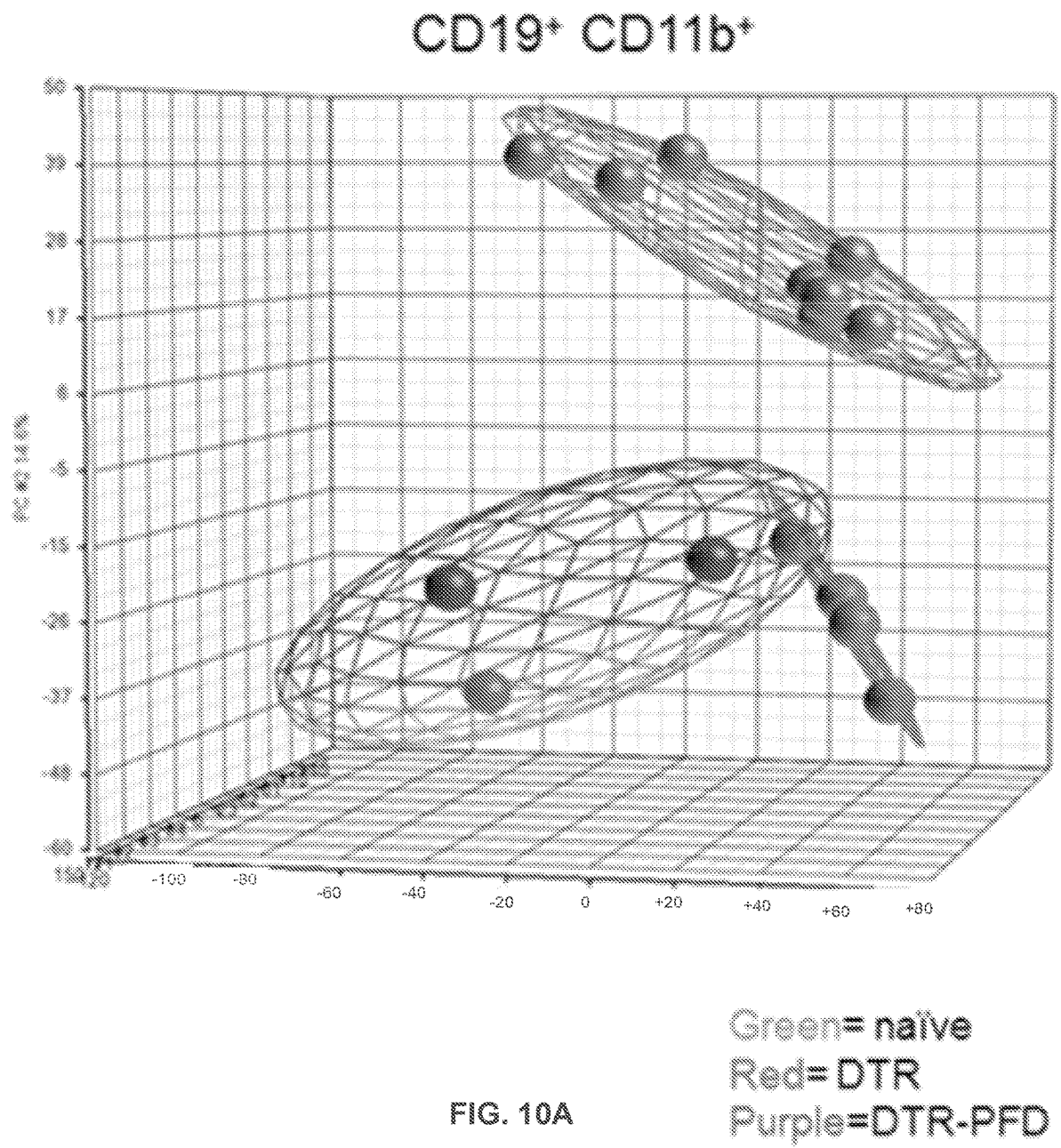
Figure 10B:
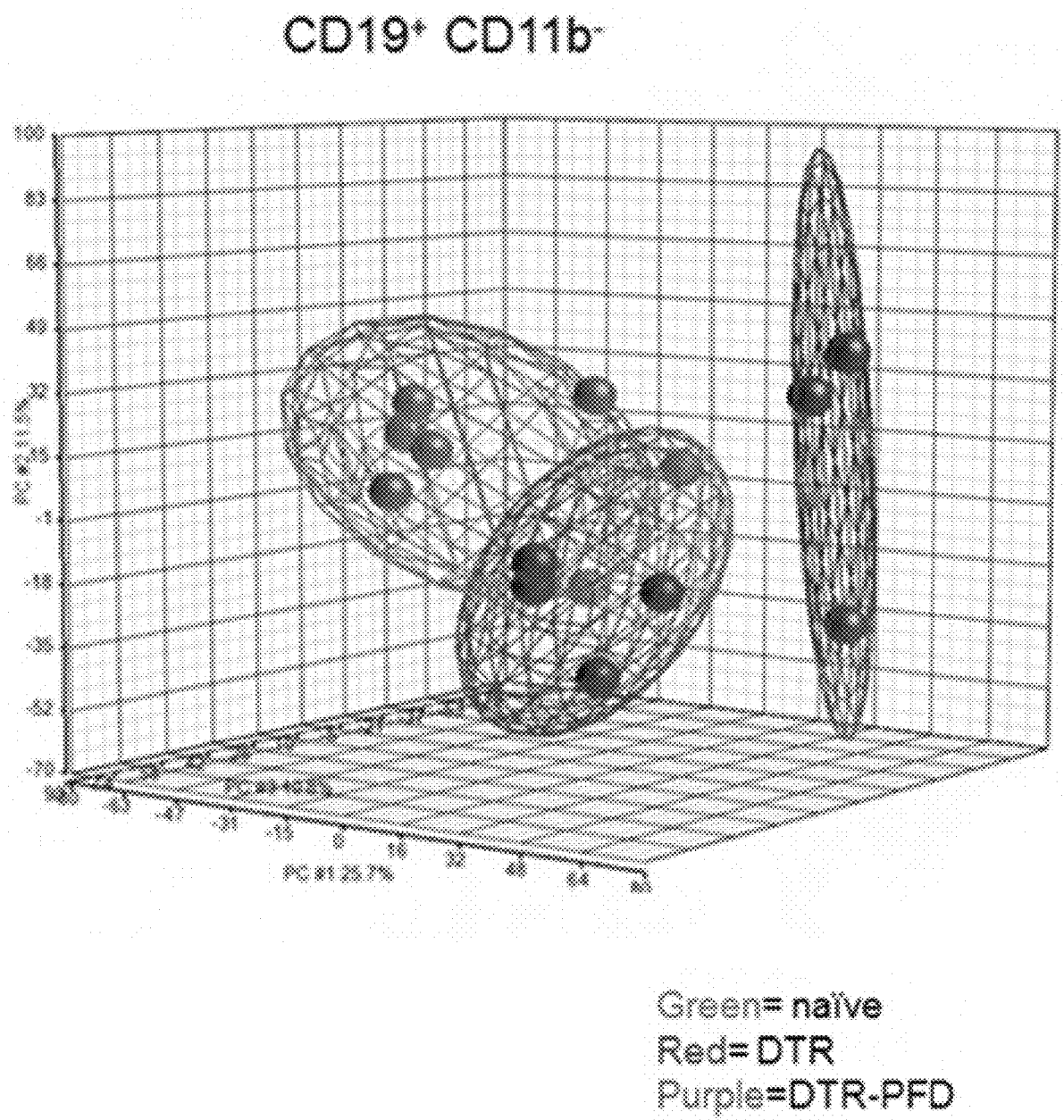
Figure 10E:
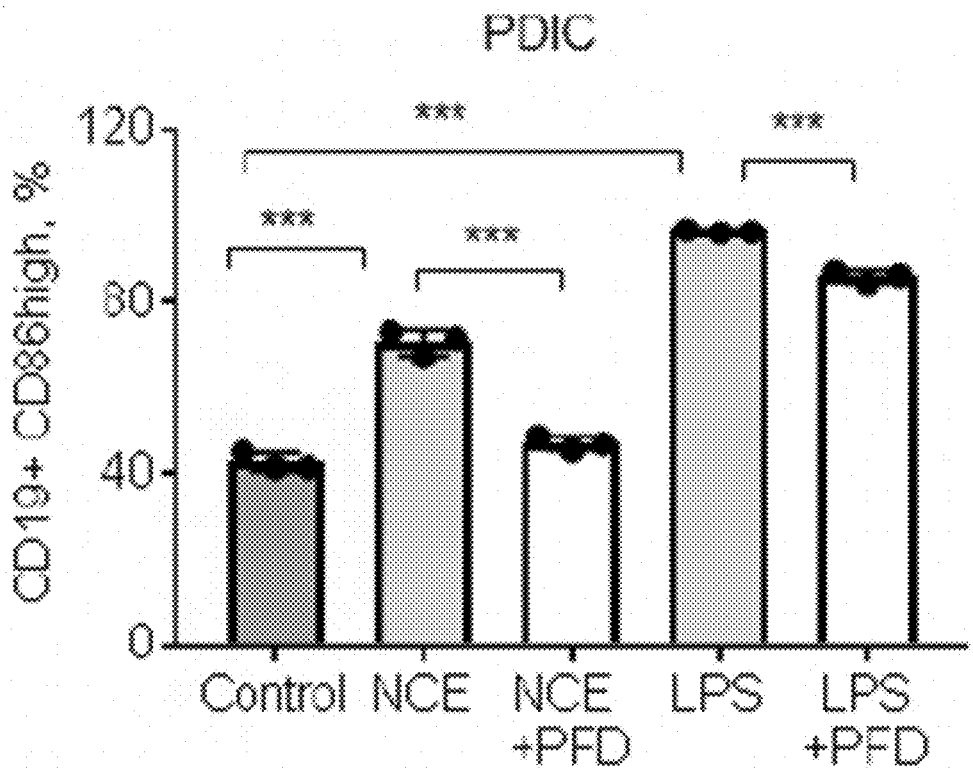
Figure 10F:
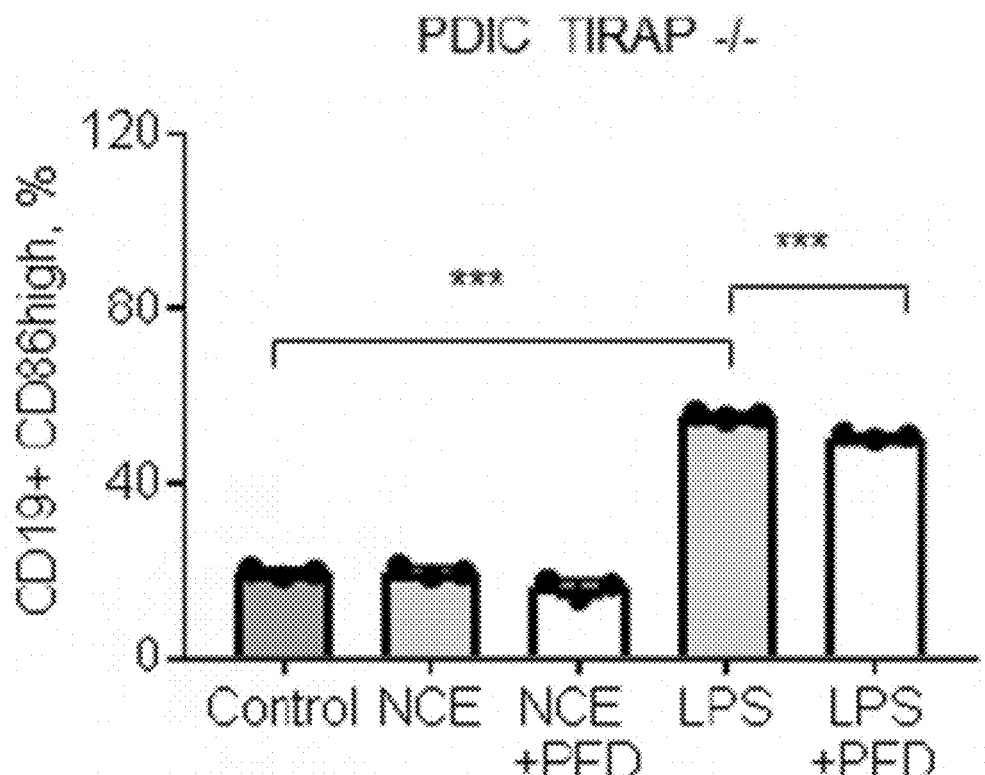
Figure 10G:
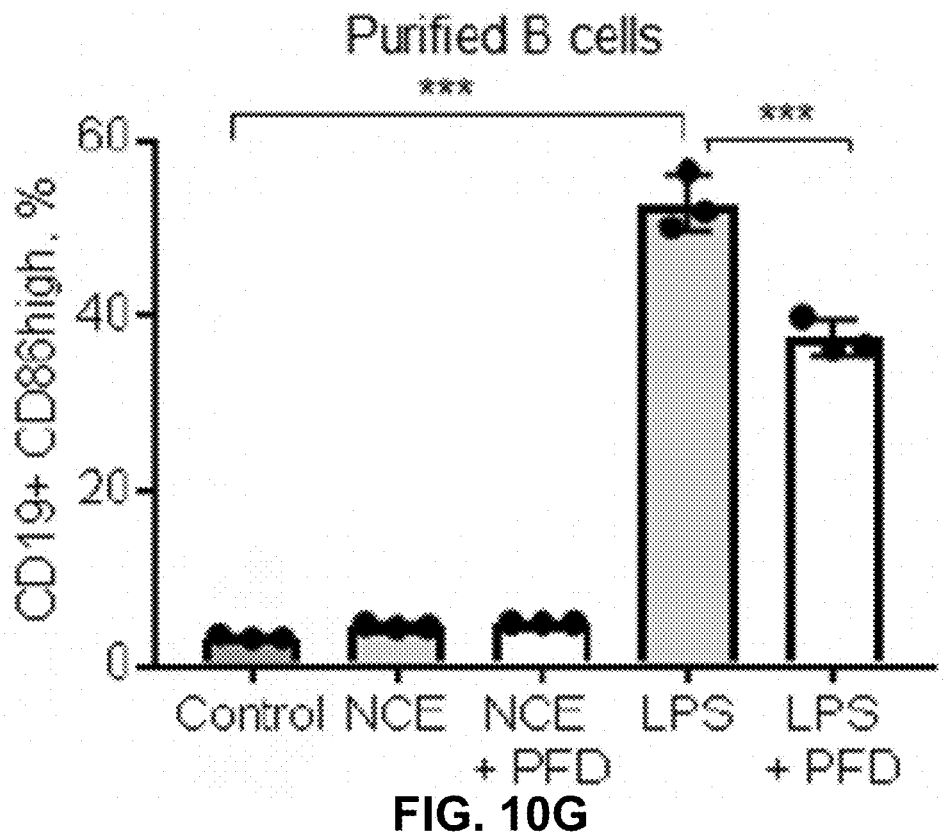
Figure 10H:
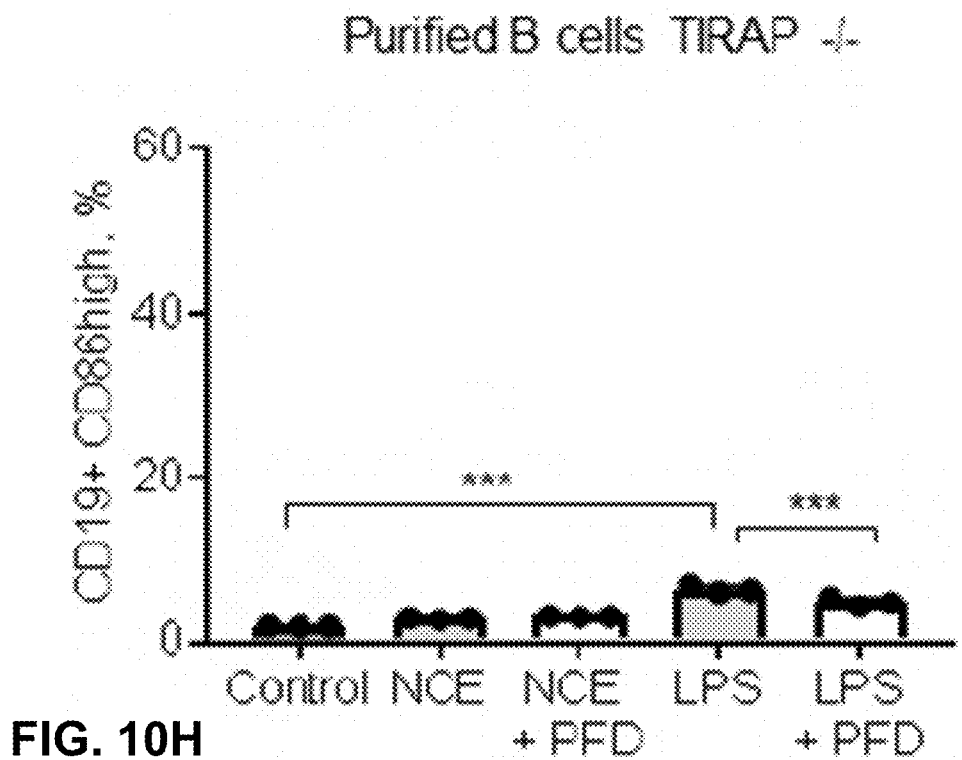
Figure 10I:
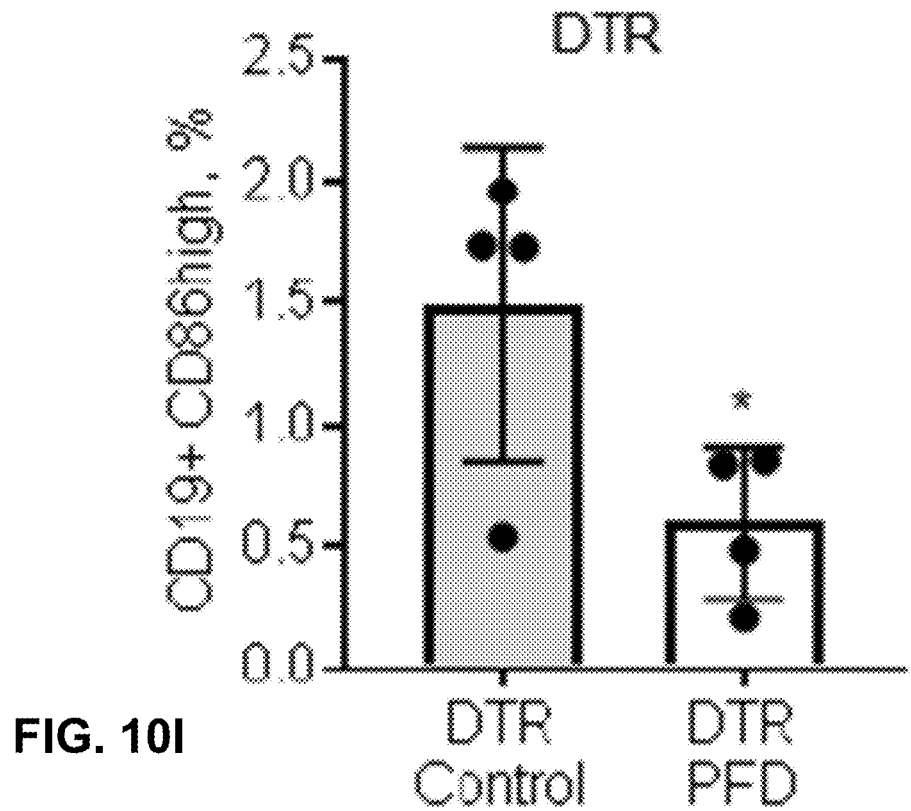
Figure 10J:
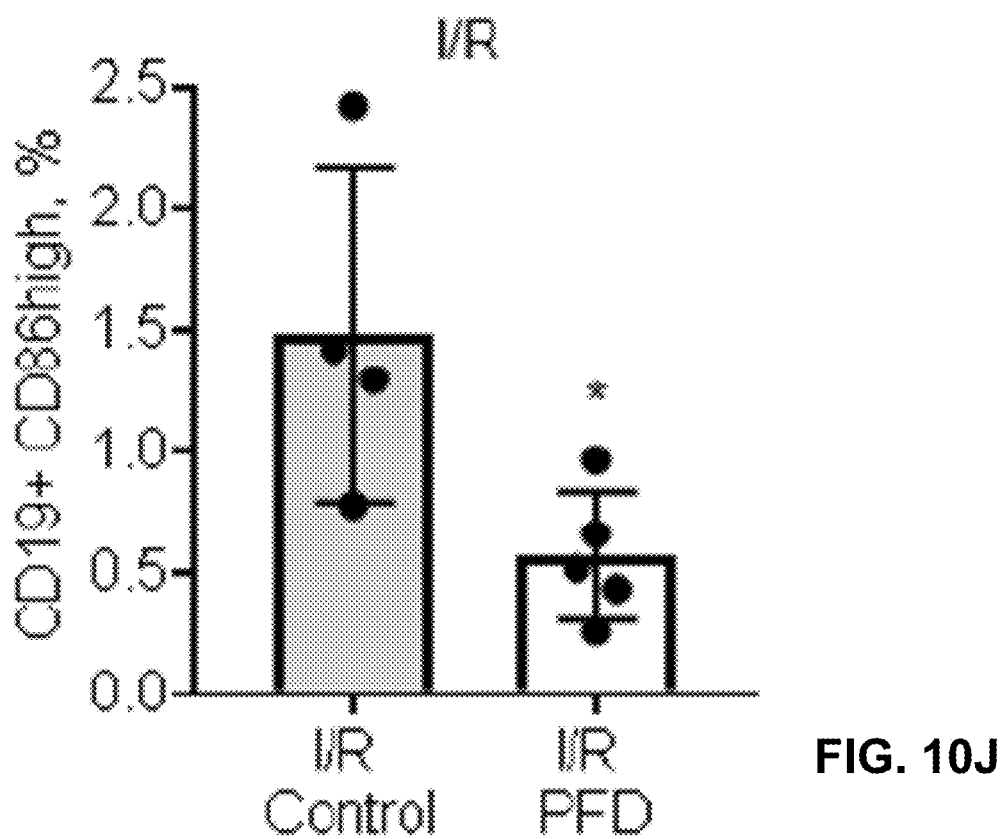

FIG. 10A, FIG. 10B, FIG. 10C, FIG. 10D, FIG. 10E, FIG. 10F, FIG. 10G, FIG. 10H, FIG. 10I and FIG. 10J show the transcriptional profiling of CD19+CD11b+ and CD19+CD11b− cells and the analysis of B cell activation in wild-type and TIRAP deficient immune cells. Mice expressing the diphtheria toxin receptor in the myocardium were either left untreated (naive) or exposed to diphtheria toxin and fed chow enriched with Pirfenidone (DTR-PFD) or regular chow (DTR). Mice were sacrificed at day 4 post diphtheria toxin (DT) injection and the heart was collected for analysis via flow cytometry. CD19+CD11b+ and CD19+CD11b− cells were FACS sorted from naïve hearts, and hearts from DT-treated mice fed regular diet (DTR) Pirfenidone enriched diet (PFD) and transcriptional profiling was performed using RNAseq. FIG. 10A) Principal component analysis of myocardial CD19+CD11b+ lymphocytes isolated from naive mice (green), DTR treated mice (red) and DTR treated mice exposed to Pirfenidone (purple). FIG. 10B) Principal component analysis of myocardial CD19+CD11b− lymphocytes isolated from naive mice (green), DTR treated mice (red) and DTR treated mice exposed to Pirfenidone (purple). FIG. 10C-FIG. 10D) KEGG pathway analysis of genes with differential expression between DTR injured and naïve mice (left column) and DTR injured+Pirfenidone and naïve mice (right column) in CD19+CD11b+ lymphocytes (FIG. 10C) and CD19+CD11b− lymphocytes (FIG. 10D). FIG. 10E-FIG. 10F), Unfractionated peritoneal derived immune cells were collected on day 4 post intraperitoneal injection of thyoglycollate and placed in culture. Cells were cultured in media alone (Control), in the presence of necrotic cells extracts from H9c2 cells (NCE), in the presence of NCE and Pirfenidone (NCE-PFD), in the presence of LPS (LPS) or in the presence of LPS and Pirfenidone (LPS-PFD). After 24 h of culture, cells were collected for flow cytometric analysis and the prevalence of CD19+CD86high cells was quantified. 3 biological replicates per each experiment are reported. FIG. 10E reports results from immune cells collected from wild type mice, FIG. 10F reports results from immune cells collected from TIRAP−/− animals. FIG. 10G-FIG. 10H), B lymphocytes were purified from the spleen and cultured for 24 hours under the same conditions described for panels A and B. After 24 h of culture, cells were collected for flow cytometric analysis and the prevalence of CD19+CD86high cells was quantified. 3 biological replicates per each experiment are reported. FIG. 10G reports results from splenic B cells purified from wild type mice, FIG. 10H reports results from immune cells collected from TIRAP−/− animals. FIG. 10I-FIG. 10J), Mice were subjected to acute myocardial injury either by exposure to diphtheria toxin (FIG. 10I) or through 90 minutes of closed chest ischemia followed by reperfusion (FIG. 10J). Mice were fed regular chow (Control) or chow enriched with Pirfenidone (PFD). On day 4 post injury, the myocardium was collected and analyzed via flow cytometry to assess the number of myocardial CD19+CD86 high cells. Panel E, n=4 per/group, Panel F, n=4 control, n=5 PFD. *=p<0.05, ***=p<0.001. Bars represent mean. Error bars represent standard deviation. P values were calculated with one-way ANOVA followed by Tukey's test for multiple comparisons in panels A to D and with Student's T-test in panels E and F.

Figure 11A:
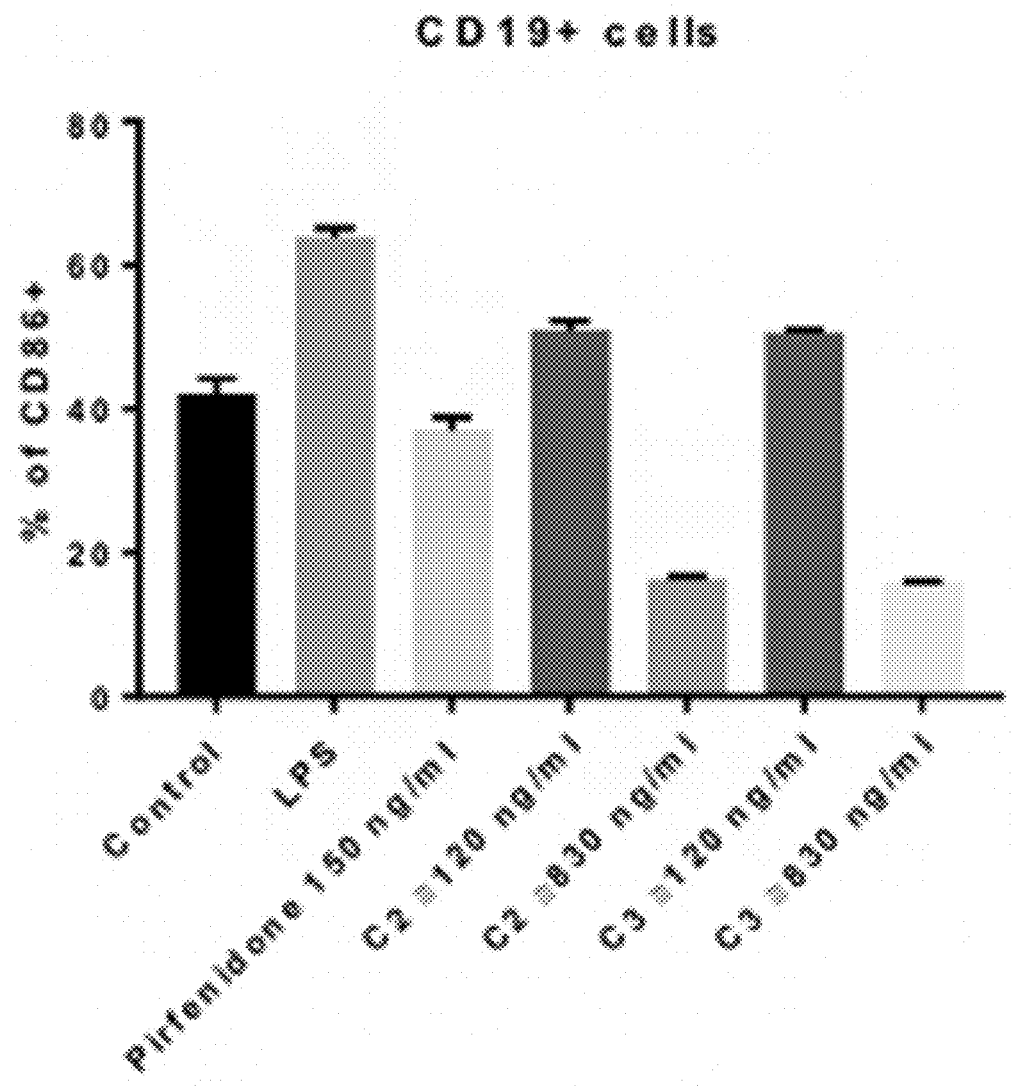
Figures 11B, 11C:
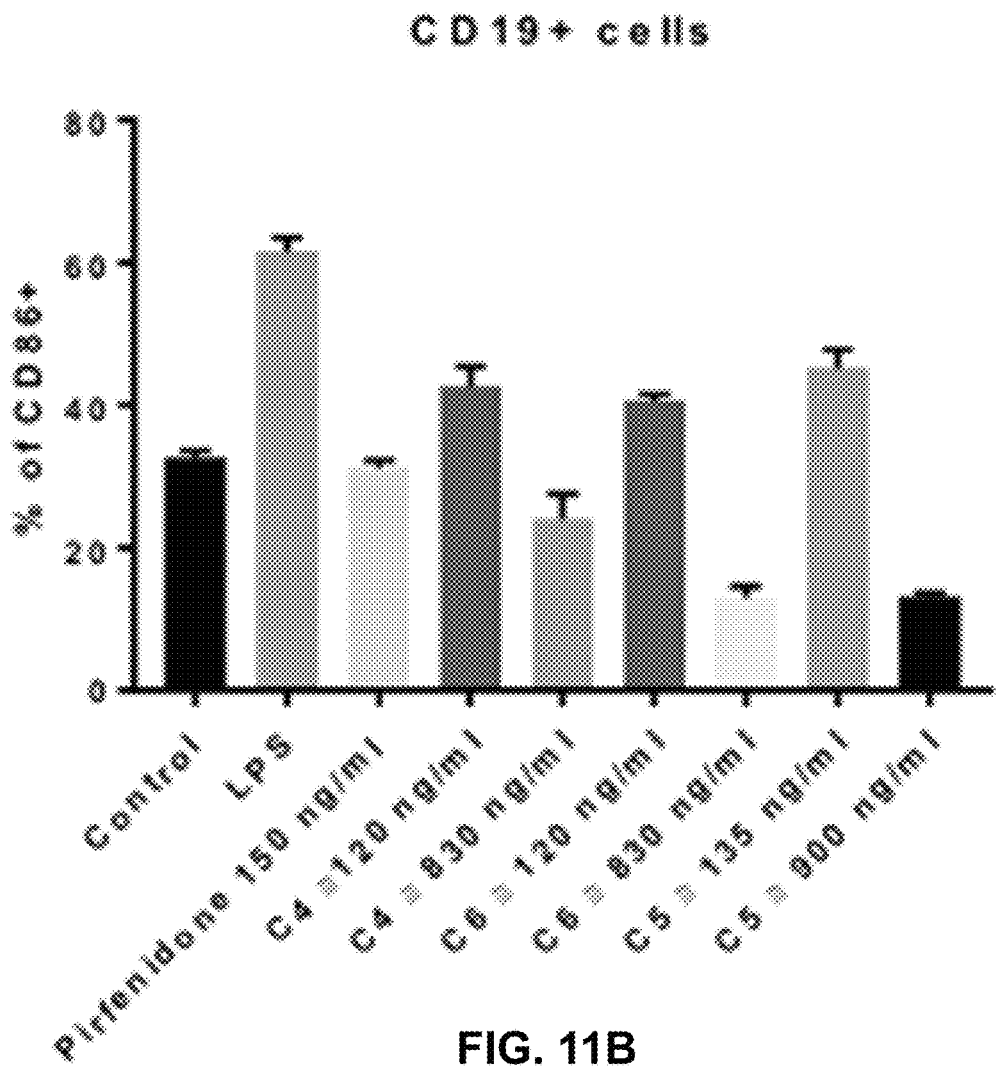
Figure 11D:
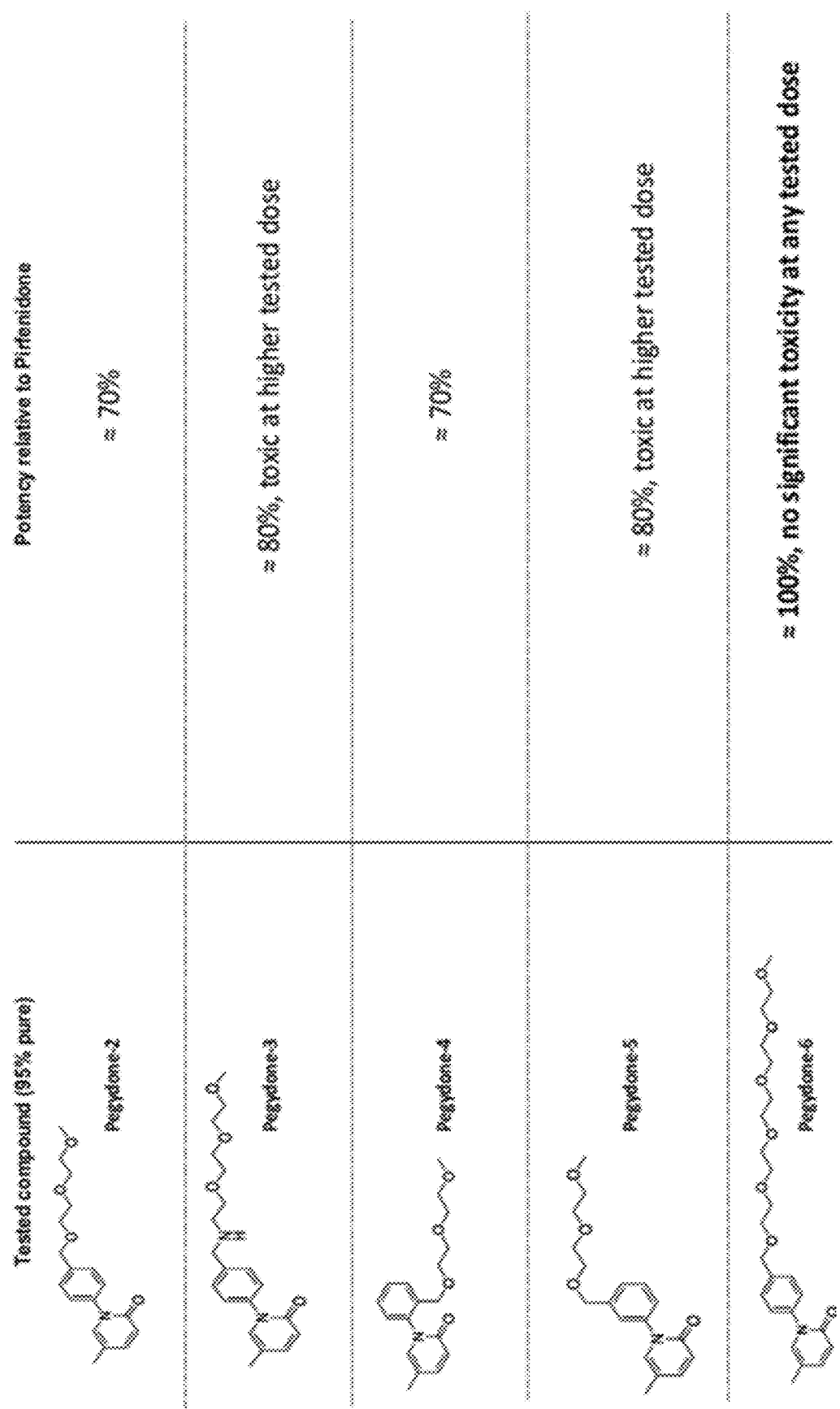

FIG. 11A, FIG. 11B, FIG. 11C and FIG. 11D show the expression of CD86 on CD19+ in peritoneal derived inflammatory cells cultured for 24 hours. Peritoneal derived inflammatory cells were collected on day for post intraperitoneal injection of Thyoglicollate. Cells were cultured for 24 h in baseline condition (control), in the presence of LPS 100 ng/ml (LPS) or in the presence of LPS 100 ng/ml and various concentrations of different forms of Pegylated Pirfenidone (named C2 and C3 in FIG. 11A and C4 to C6 in FIG. 11B)). After the 24 h in culture cells were collected and analyzed via flow cytometry to assess the expression of CD86 on CD19+ cells (B lymphocytes). The graphs in FIG. 11A and FIG. 11B show that both Pirfenidone and the tested forms of Pegylated Pirfenidone reduced the expression of CD86 on CD19+ cells. FIG. 11C reports the molecular weights of the tested forms of PEGylated Pirfenidone and the molecular weight (MW) ration between the tested compound and Pirfenidone). FIG. 11D shows the molecular structures of the tested PEGylated Pirfenidone variants (C2 to C6) together with an assessment of their relative potency to Pirfenidone (calculated converting the amount of drugs used from concentrations in weight to molarity) and an assessment of in vitro toxicity (assessed by visual inspection of the cultured cells and DAPI staining at the time of flow cytometric analysis). Importantly, the table shows that the tested variants of PEG-Pirfenidone are not equivalent and C6 (Pegydone 6) is superior to the other tested variants.

Figure 12A:
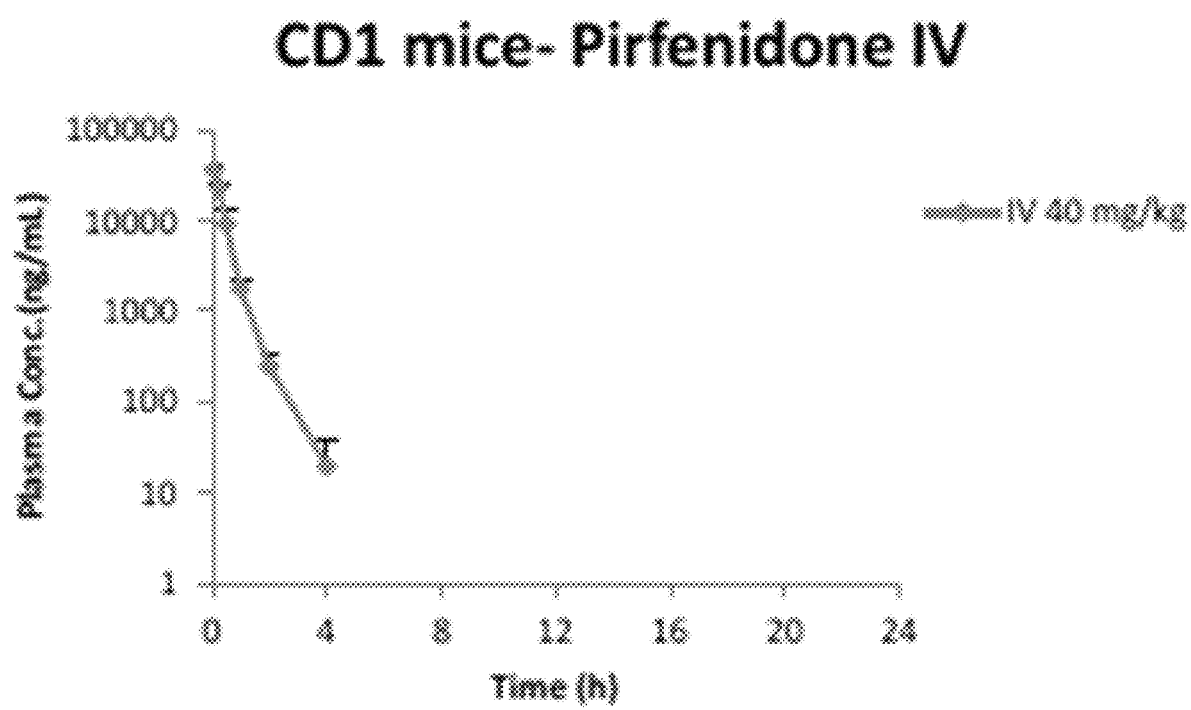
Figure 12B:
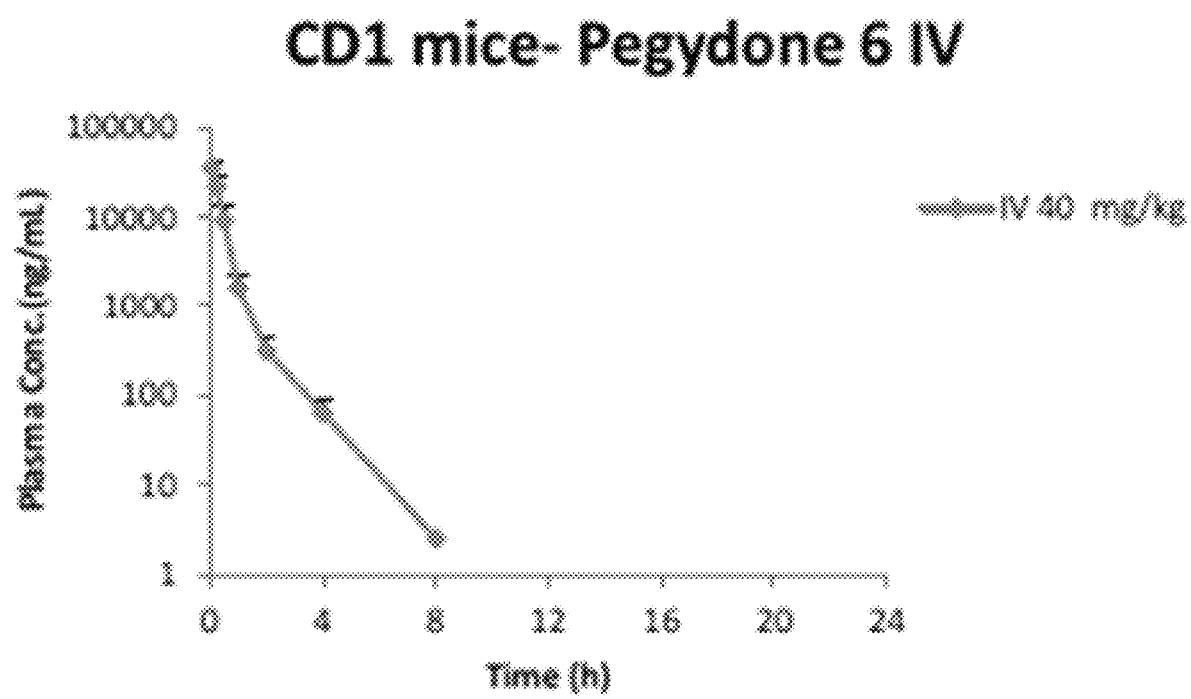

FIG. 12A, FIG. 12B, and FIG. 12C show Pk and bioavailability of Pegydone 6 compared to Pirfenidone. 6-8 weeks old CD-1/ICR mice were administered 40 mg/kg of Pirfenidone or Pegydone-6 IV or PO. Blood was collected at pre-specified time points and the concertation of the administered drug was measured by mass spectrometry (LC-MS-MS). Each time point was collected in triplicate. FIG. 12A reports the data collected after IV administration of Pirfenidone, FIG. 12B reports the data collected after administration of Pegydone 6. FIG. 12C reports the half-life of the two drugs as calculated from the graphs reported in FIG. 12A and FIG. 12B. FIG. 12C reports the calculated half-life and bioavailability of Pegydone 6 and Pirfenidone.

Figure 13A:
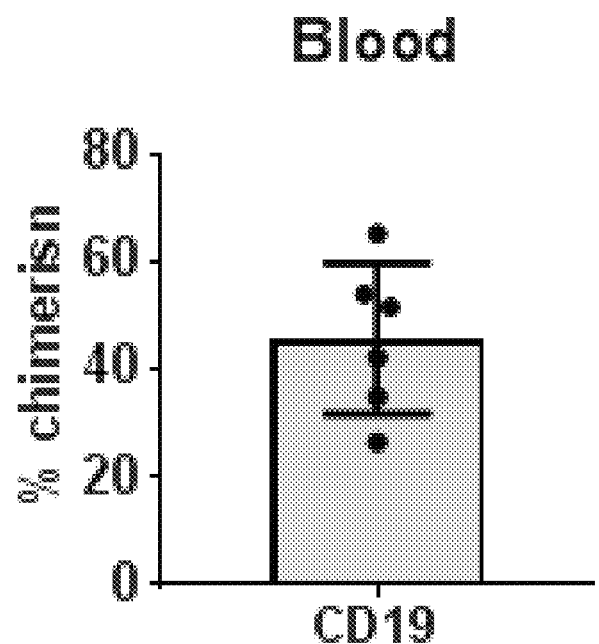
Figure 13B:
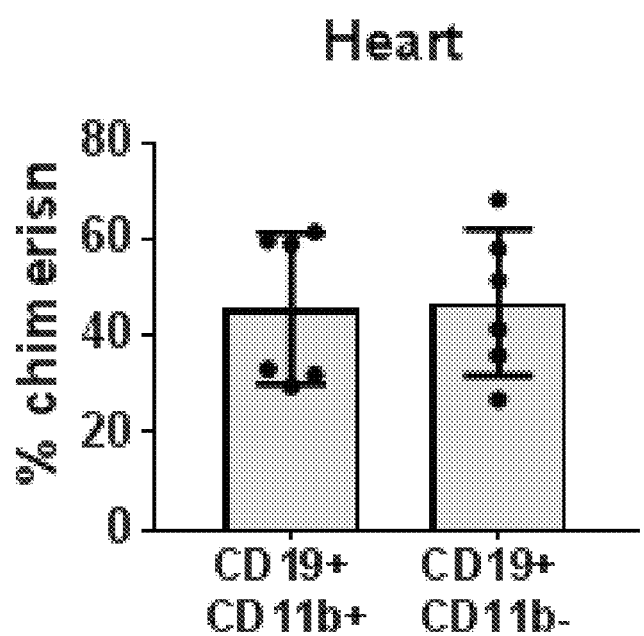
Figure 13C:
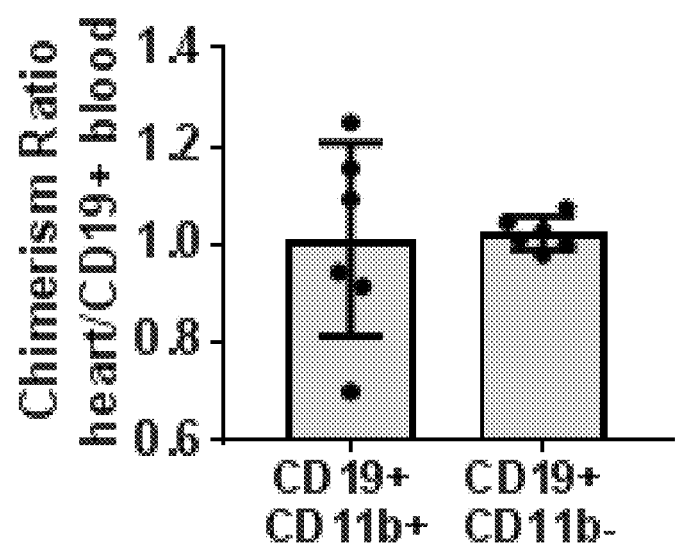

FIG. 13A, FIG. 13B, and FIG. 13C show dynamics of myocardial B lymphocytes. FIG. 13A shows after 3 weeks of Parabiosis conjoined mice show 50% chimerism of circulating CD19+ B lymphocytes. FIG. 13B Analysis of chimerism of myocardial B lymphocytes. Conjoined animals show 50% of chimerism in both CD19+CD11 b+ and CD19+CD11 b− myocardial B lymphocytes. FIG. 13C ratio of chimerism between myocardial CD19+ cells and circulating CD19+ cells. The ratio of B cell chimerism between blood and myocardium is about 1. This confirms that myocardial B lymphocytes recirculate rapidly and are at equilibrium with circulating B lymphocytes and demonstrates that the effects of Pirfenidone and/or PEGpirfenidoen on myocardial B cells could be assessed on peripheral blood B lymphocytes.

Figure 14A:
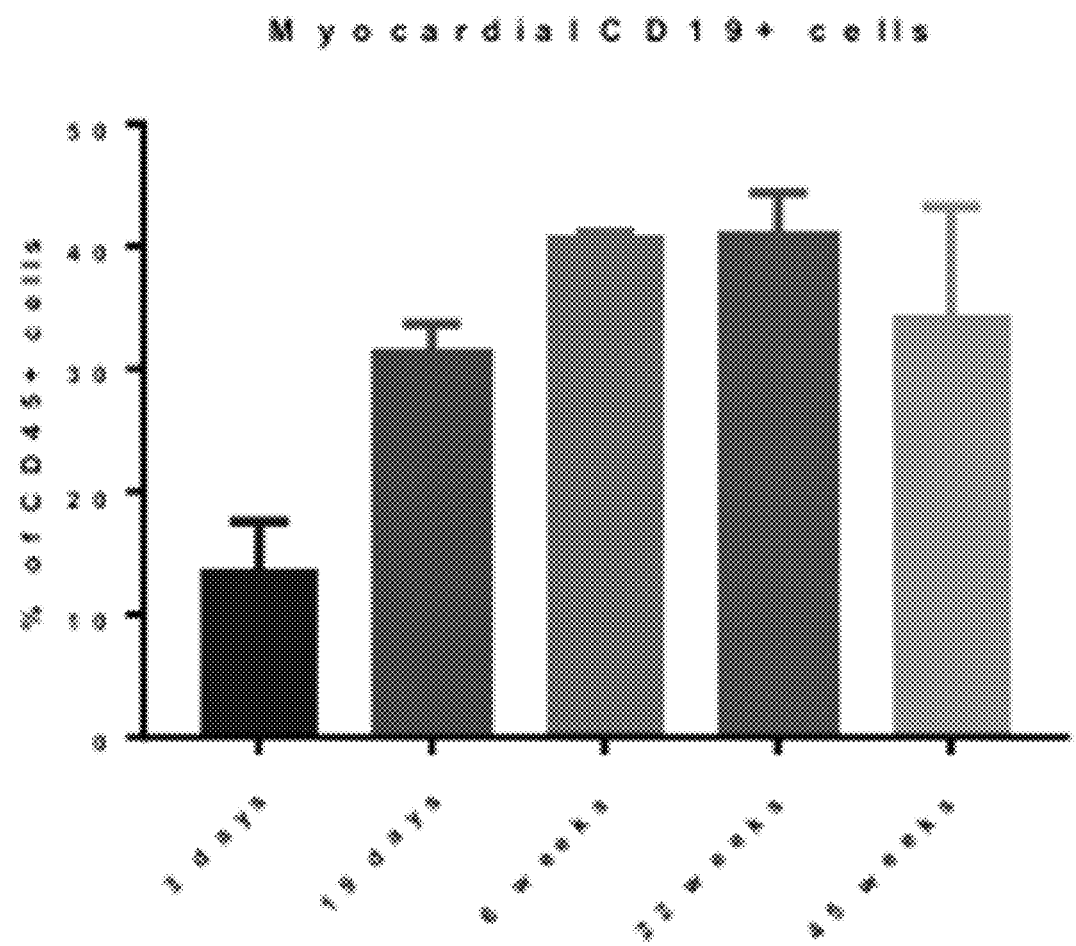
Figure 14B:
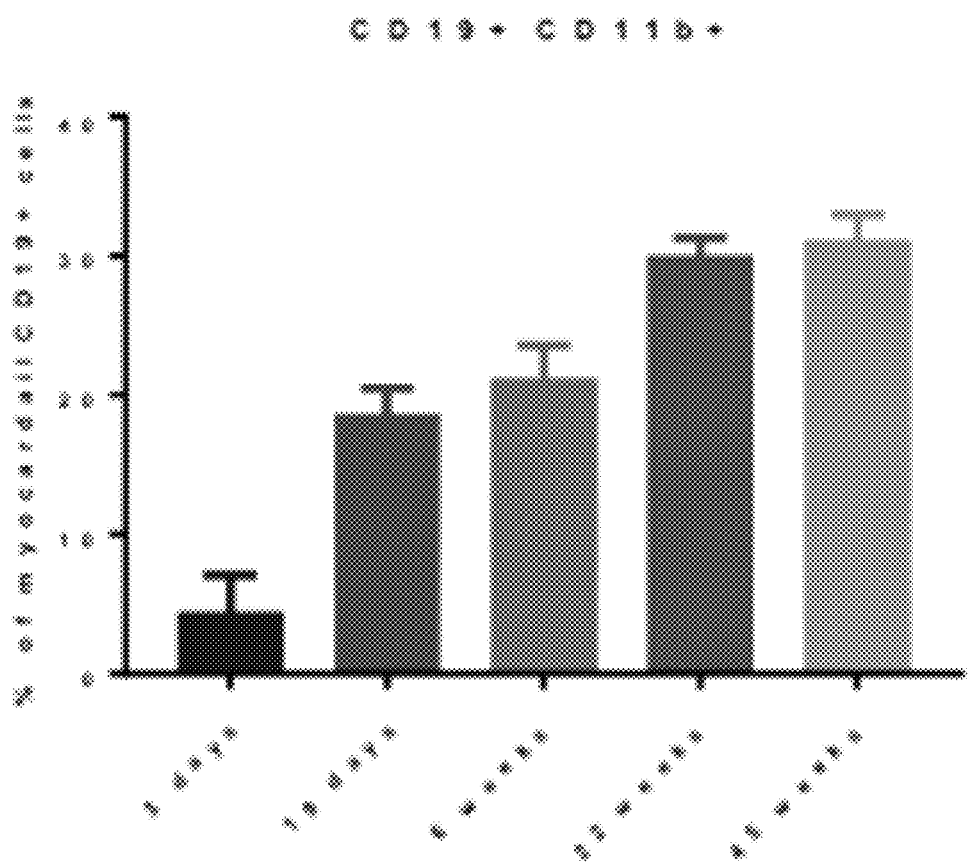
Figure 14C:
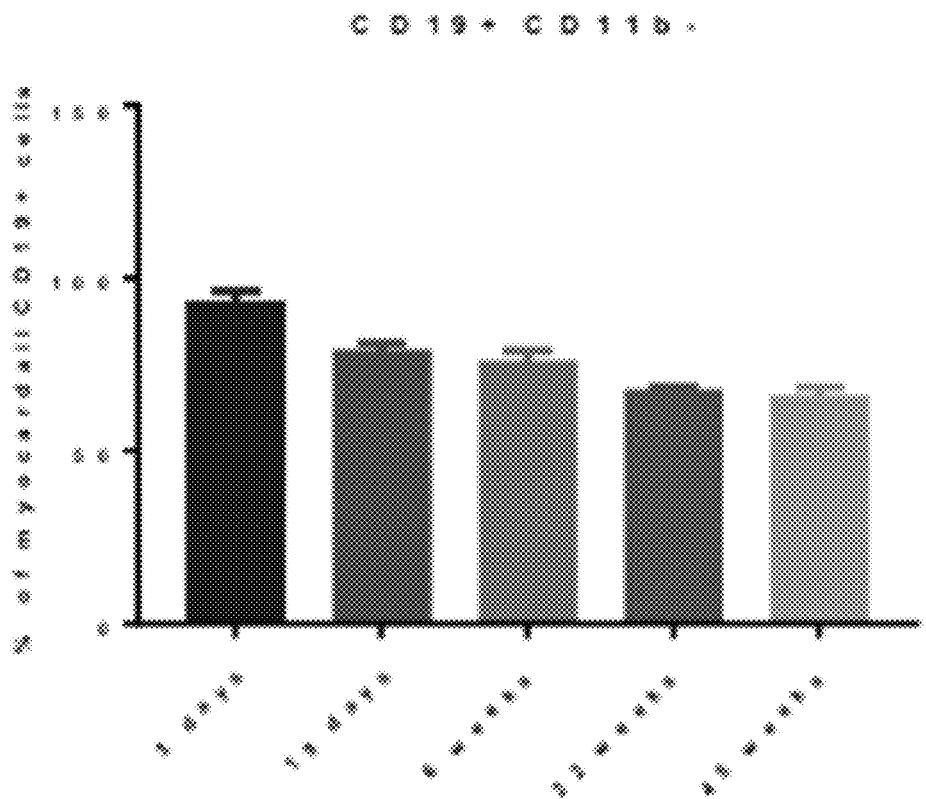
Figure 14D:
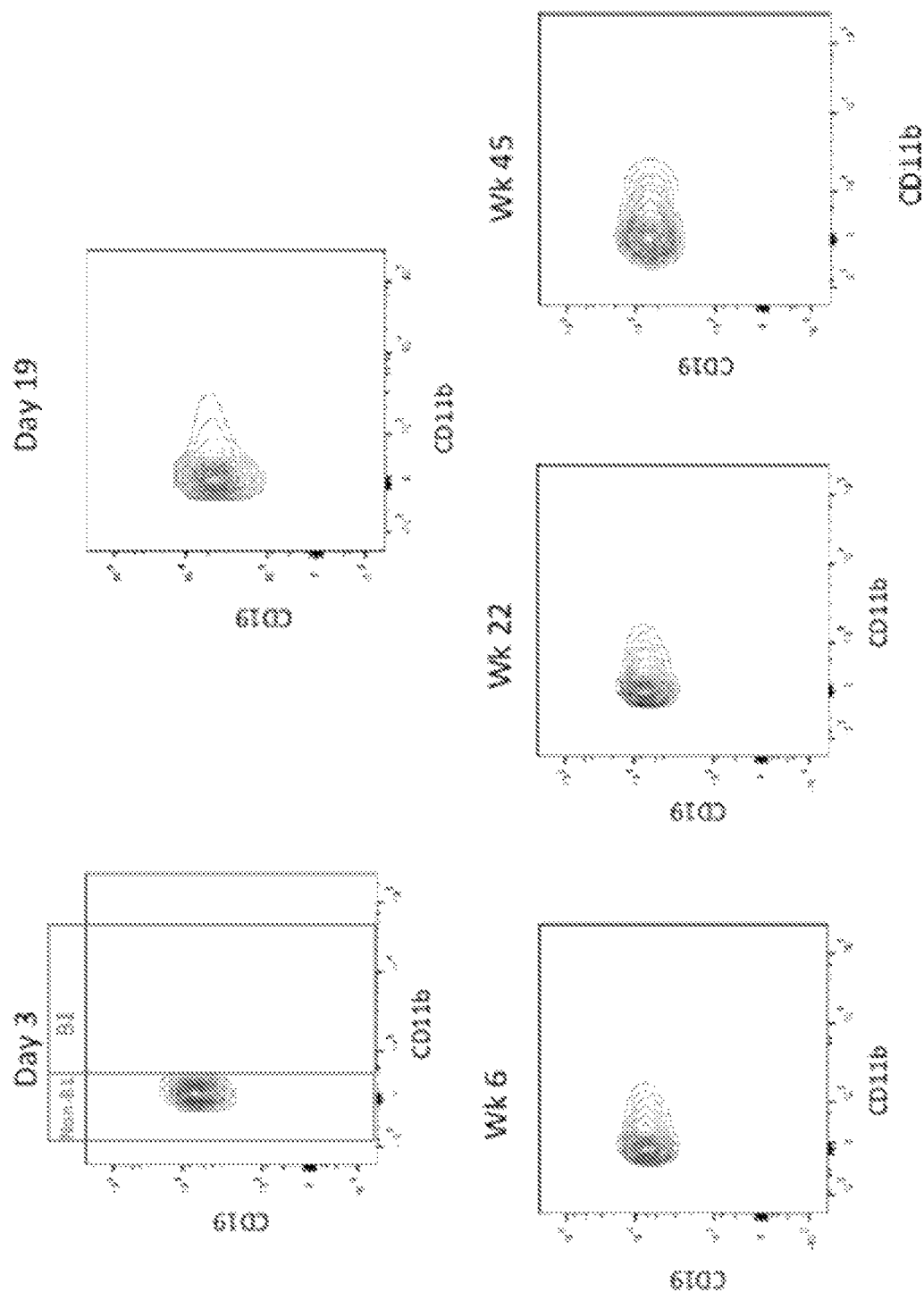

FIG. 14A, FIG. 14B, FIG. 14C and FIG. 14D show that myocardial B cells change with aging and that therefore Pirfenidone and/or PEG-Pirfenidone could be used to modulate age associated changes in myocardial B cells. Mice of the indicated different ages were sacrificed and the hearts were analyzed via flow cytometry. Each time point was measured in triplicate. FIG. 14A shows that with aging the prevalence of CD19+ cells increases. FIG. 14B shows that the prevalence of CD19+CD11b+ cells increases as well. FIG. 14C shows that with aging the prevalence of CD19+ CD11b− cells decreases.

Figure 15:
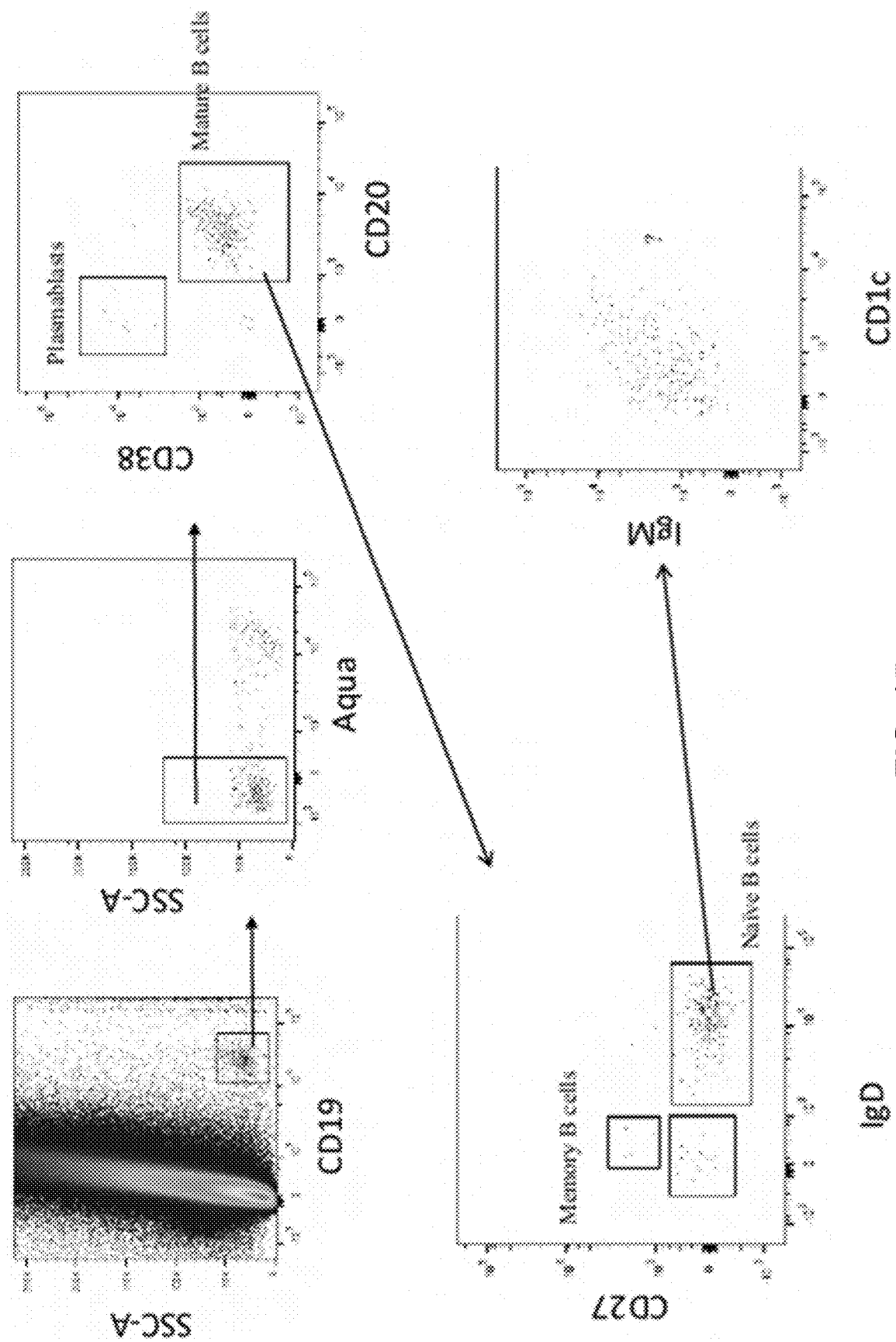

FIG. 15 shows flow cytometric analysis of B lymphocytes in a sample of a human heart. The data shows that the human heart harbors populations of B cells similar to those observed in the murine heart and therefore argues that Pirfenidone or PEG-Pirfenidone are likely to have in humans cardioprotective effects similar to those observed in mice.

FIG. 16A, FIG. 16B, FIG. 16C, FIG. 16D, FIG. 16E, FIG. 16F, FIG. 16G, FIG. 16H, FIG. 16I, FIG. 16J, FIG. 16K, FIG. 16L, FIG. 16M, FIG. 16N, FIG. 16O, FIG. 16P, FIG. 16Q, FIG. 16R, FIG. 16S, FIG. 16T, FIG. 16U, FIG. 16V and FIG. 16W illustrate the chemical structure of various PEGylated pirfenidone derivatives.

DETAILED DESCRIPTION OF THE INVENTION

Provided herein are compositions comprising a Pirfenidone (PFD) derivative and methods of use. Applicants have discovered that PFD derivatives are capable of modulating B lymphocyte activity and organ protection from acute injury. Furthermore, Applicants have discovered that pegylated Pirfenidone maintains biological activity on B lymphocytes. In some embodiments, PEG-Pirfenidone compounds are equipotent to Pirfenidone in their ability to modulate B lymphocytes activity. In some embodiments, PEG-Pirfenidone has an increased half-life and/or increased bioavailability compered to Pirfenidone.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules of the compound are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Additional aspects of the disclosure are described below.
(I) Compositions

One aspect of the present disclosure encompasses PFD or a PFD derivative. PFD or PFD derivatives may be modified to improve potency, bioavailability, solubility, stability, handling properties, or a combination thereof, as compared to an unmodified version. Thus, in another aspect, a composition of the invention comprises modified PFD or PFD derivative. In still another aspect, a composition of the invention comprises a prodrug of a PFD or PFD derivative.

A composition of the invention may optionally comprise one or more additional drug or therapeutically active agent in addition to the PFD or PFD derivative. A composition of the invention may further comprise a pharmaceutically acceptable excipient, carrier, or diluent. Further, a composition of the invention may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents, or antioxidants.

Other aspects of the invention are described in further detail below.
(a) Pirfenidone (PFD) and PFD Derivatives In general, the compounds detailed herein include compounds comprising a PFD, or 5 methyl-1-phenyl-2-[H] pyridone, structure as diagrammed below. PFD is a non-peptide synthetic molecule with a molecular weight of 185.23 daltons. Its chemical elements are expressed as $C_{12}H_{11}NO$, and its synthesis is known. For example, PFD can also be produced by a number of organic synthesis methods including those described in U.S. Pat. No. 8,519,140, herein incorporated by reference in its entirety. PFD is manufactured commercially and being evaluated clinically as a broad-spectrum anti-fibrotic drug.

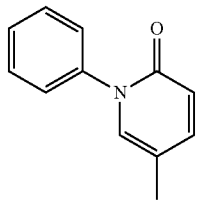

Provided herein are derivatives of PFD. PFD derivatives are modified versions of PFD that are able to modulate B lymphocyte activity. As used herein a "PFD derivative" may be a PFD derivative known in the art, a PFD derivative of Formula (I) or Formula (II). PFD derivatives are known in the art. See for example, CN 106083702, CN 105884680, WO 2009035598, Bioorg Med Chem Lett. 2014 Jan. 1; 24(1):220-3, Molecules 2012(17): 884-896, and Medicinal Chemistry Research October 2005; 14(7); 382-403, each of which are incorporated herein in its entirety by reference. PDF derivatives with the ability to modulate B lymphocyte activity are potentially used as drugs which protect organs from acute tissue damage or mitigate disease caused by dysregulation of B cell activity.

Provided herein are compounds comprising Formula (I):

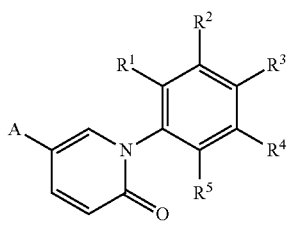

wherein:
R$^1$, R$^2$, R$^3$, R$^4$, and R$^5$ are each independently selected from the group consisting of hydrogen, deuterium or L-X—B;
wherein L is a linker which comprises a C$_{1-12}$ alkyl; X is O-PEG, NH(CH$_2$)$_m$O-PEG, or S(CH$_2$)$_m$O-PEG; m is an integer from 1-10; wherein PEG is selected the group of mPEG (methoxy polyethylene glycol), linear PEG, branched PEG, multi-arm PEG, and PEG-lipid; B is selected from the group consisting of hydrogen, deuterium, a substituted or unsubstituted C$_1$ to C$_6$ alkyl, a substituted or unsubstituted C$_1$ to C$_6$ alkenyl, a substituted or unsubstituted C$_1$ to C$_6$ alkynyl, a substituted or unsubstituted aryl, and a substituted or unsubstituted heteroaryl, or deuterated versions thereof; and A is selected from the group consisting of hydrogen, deuterium, halogen, CF$_3$, CD$_3$, CN, OH, OCH$_3$, OR", SR", NR"R", NR"COR", NR"CONR"R", NR"CO$_2$R", COR", CO$_2$R", NOR", NO$_2$, CONR"R", OC(O)NR"R", SO$_2$R", SO$_2$NR"R", NR"SO$_2$R", NR"SO$_2$NR"R", C(O)C(O)R", and C(O)CH$_2$C(O)R", a substituted or unsubstituted C$_1$ to C$_6$ alkyl, a substituted or unsubstituted C$_1$ to C$_6$ alkenyl, a substituted or unsubstituted C$_1$ to C$_6$ alkynyl, a substituted or unsubstituted aryl, and a substituted or unsubstituted heteroaryl; and R" may be independently selected from the group consisting of hydrogen, deuterium, substituted C$_1$-C$_4$ aliphatic moiety, aliphatic moiety containing nitrogen, oxygen, or sulfur, or alternately, two R" moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur.

The PEG has a molecular weight ranging from about 100 to about 50,000 Daltons, about 200 to about 50,000 Daltons, about 300 to about 50,000 Daltons, about 400 to about 50,000 Daltons, about 500 to about 50,000 Daltons, about 600 to about 50,000 Daltons, about 700 to about 50,000 Daltons, about 800 to about 50,000 Daltons, about 900 to about 50,000 Daltons, from about 1,000 to about 50,000 Daltons, from about 1,500 to about 50,000, from about 2,000 to about 50,000, from about 2,500 to about 50,000, from about 3,000 to about 50,000, from about 3,500 to about 50,000, from about 4,000 to about 50,000, from about 4,500 to about 50,000, from about 5,000 to about 50,000, from about 5,500 to about 50,000, from about 6,000 to about 50,000, from about 6,500 to about 50,000, from about 7,000 to about 50,000, from about 7,500 to about 50,000, from about 8,000 to about 50,000, from about 8,500 to about 50,000, from about 9,000 to about 50,000, from about 9,500 to about 50,000, from about 10,000 to about 50,000, from about 11,000 to about 50,000, from about 12,000 to about 50,000, from about 13,000 to about 50,000, from about 14,000 to about 50,000 Daltons, from about 15,000 to about 50,000 Daltons, from about 16,000 to about 50,000 Daltons, from about 17,000 to about 50,000 Daltons, from about 18,000 to about 50,000 Daltons, from about 19,000 to about 50,000 Daltons, from about 20,000 to about 50,000 Daltons, from about 30,000 to about 50,000 Daltons, or from about 40,000 to about 50,000 Daltons. In some embodiments the PEG has a molecular weight ranging from about 40 Daltons to about 1,200 Daltons. In some embodiments, the PEG has a molecular weight of less than about 1,000 Daltons. In some embodiments, the PEG has a molecular weight of about 1,000 Daltons.

In an embodiment, a compound of Formula (I) comprises any of the preceding compounds of Formula (I), wherein R$^1$ may be selected from the group consisting of hydrogen, deuterium or L-X—B; wherein L is a linker which comprises a C$_{1-12}$ alkyl; X is O-PEG, NH(CH$_2$)$_m$O-PEG, or S(CH$_2$)$_m$O-PEG; m is an integer from 1-10; wherein PEG is selected the group of mPEG (methoxy polyethylene glycol), linear PEG, branched PEG, multi-arm PEG, and PEG-lipid; B is selected from the group consisting of hydrogen, deuterium, a substituted or unsubstituted C$_1$ to C$_6$ alkyl, a substituted or unsubstituted C$_1$ to C$_6$ alkenyl, a substituted or unsubstituted C$_1$ to C$_6$ alkynyl, a substituted or unsubstituted aryl, and a substituted or unsubstituted heteroaryl, or deuterated versions thereof. In a particular embodiment, a compound of Formula (I) comprises any of the proceeding compounds of Formula (I), wherein R$^1$ is H.

In another embodiment, a compound of Formula (I) comprises any of the preceding compounds of Formula (I), wherein R$^2$ may be selected from the group consisting of hydrogen, deuterium or L-X—B; wherein L is a linker which comprises a C$_{1-12}$ alkyl; X is O-PEG, NH(CH$_2$)$_m$O-PEG, or S(CH$_2$)$_m$O-PEG; m is an integer from 1-10; wherein PEG is selected the group of mPEG (methoxy polyethylene glycol), linear PEG, branched PEG, multi-arm PEG, and PEG-lipid; B is selected from the group consisting of hydrogen, deuterium, a substituted or unsubstituted C$_1$ to C$_6$ alkyl, a substituted or unsubstituted $C_1$ to $C_6$ alkenyl, a substituted or unsubstituted $C_1$ to $C_6$ alkynyl, a substituted or unsubstituted aryl, and a substituted or unsubstituted heteroaryl, or deuterated versions thereof. In a particular embodiment, a compound of Formula (I) comprises any of the proceeding compounds of Formula (I), wherein $R^2$ is selected from hydrogen or L-X—B, wherein L is a linker which comprises a $C_{1-2}$ alkyl; X is O-PEG, wherein PEG is selected the group of a, linear PEG, branched PEG, multi-arm PEG, and PEG-lipid; and B is $CH_3$.

In still another embodiment, a compound of Formula (I) comprises any of the preceding compounds of Formula (I), wherein $R^3$ may be selected from the group consisting of hydrogen, deuterium or L-X—B; wherein L is a linker which comprises a $C_{1-12}$ alkyl; X is O-PEG, $NH(CH_2)_mO$-PEG, or $S(CH_2)_mO$-PEG; m is an integer from 1-10; wherein PEG is selected the group of mPEG (methoxy polyethylene glycol), linear PEG, branched PEG, multi-arm PEG, and PEG-lipid; B is selected from the group consisting of hydrogen, deuterium, a substituted or unsubstituted $C_1$ to $C_6$ alkyl, a substituted or unsubstituted $C_1$ to $C_6$ alkenyl, a substituted or unsubstituted $C_1$ to $C_6$ alkynyl, a substituted or unsubstituted aryl, and a substituted or unsubstituted heteroaryl, or deuterated versions thereof. In a particular embodiment, a compound of Formula (I) comprises any of the proceeding compounds of Formula (I), wherein $R^3$ is selected from hydrogen or L-X—B, wherein L is a linker which comprises a $C_{1-3}$ alkyl; X is O-PEG or $NH(CH_2)_mO$-PEG, wherein PEG is selected the group of mPEG (methoxy polyethylene glycol), linear PEG, branched PEG, multi-arm PEG, and PEG-lipid; m is an integer from 2-3; and B is $CH_3$.

In yet still another embodiment, a compound of Formula (I) comprises any of the preceding compounds of Formula (I), wherein $R^4$ may be selected from the group consisting of hydrogen, deuterium or L-X—B; wherein L is a linker which comprises a $C_{1-12}$ alkyl; X is O-PEG, $NH(CH_2)_mO$-PEG, or $S(CH_2)_mO$-PEG; m is an integer from 1-10; wherein PEG is selected the group of mPEG (methoxy polyethylene glycol), linear PEG, branched PEG, multi-arm PEG, and PEG-lipid; B is selected from the group consisting of hydrogen, deuterium, a substituted or unsubstituted $C_1$ to $C_6$ alkyl, a substituted or unsubstituted $C_1$ to $C_6$ alkenyl, a substituted or unsubstituted $C_1$ to $C_6$ alkynyl, a substituted or unsubstituted aryl, and a substituted or unsubstituted heteroaryl, or deuterated versions thereof. In a particular embodiment, a compound of Formula (I) comprises any of the proceeding compounds of Formula (I), wherein $R^4$ is selected from hydrogen or L-X—B, wherein L is a linker which comprises a $C_{1-3}$ alkyl; X is O-PEG or $NH(CH^2)_mO$-PEG, wherein PEG is selected the group of mPEG (methoxy polyethylene glycol), linear PEG, branched PEG, multi-arm PEG, and PEG-lipid; m is an integer from 2-3; and B is $CH_3$.

In a different embodiment, a compound of Formula (I) comprises any of the preceding compounds of Formula (I), wherein $R^5$ may be selected from the group consisting of hydrogen, deuterium or L-X—B; wherein L is a linker which comprises a $C_{1-12}$ alkyl; X is O-PEG $NH(CH_2)_mO$-PEG, or $S(CH_2)_mO$-PEG; m is an integer from 1-10; wherein PEG is selected the group of mPEG (methoxy polyethylene glycol), linear PEG, branched PEG, multi-arm PEG, and PEG-lipid; B is selected from the group consisting of hydrogen, deuterium, a substituted or unsubstituted $C_1$ to $C_6$ alkyl, a substituted or unsubstituted $C_1$ to $C_6$ alkenyl, a substituted or unsubstituted $C_1$ to $C_6$ alkynyl, a substituted or unsubstituted aryl, and a substituted or unsubstituted heteroaryl, or deuterated versions thereof. In a particular embodiment, a compound of Formula (I) comprises any of the proceeding compounds of Formula (I), wherein $R^5$ is selected from hydrogen or L-X—B, wherein L is $CH_3$; X is O-PEG, wherein PEG is selected the group of mPEG (methoxy polyethylene glycol), linear PEG, branched PEG, multi-arm PEG, and PEG-lipid; and B is $CH_3$ In an embodiment, a compound of Formula (I) comprises any of the preceding compounds of Formula (I), wherein A may be selected from the group consisting of hydrogen, halogen, $CF_3$, $CD_3$, or a substituted or unsubstituted $C_1$ to $C_6$ alkyl. In a particular embodiment, a compound of Formula (I) comprises any of the proceeding compounds of Formula (I), wherein A is selected from the group consisting of $CH_3$, $CF_3$, $CD_3$, or $CH_2$-cyclopropyl.

In exemplary embodiments, a compound of the disclosure comprises Formula (I) as shown below:

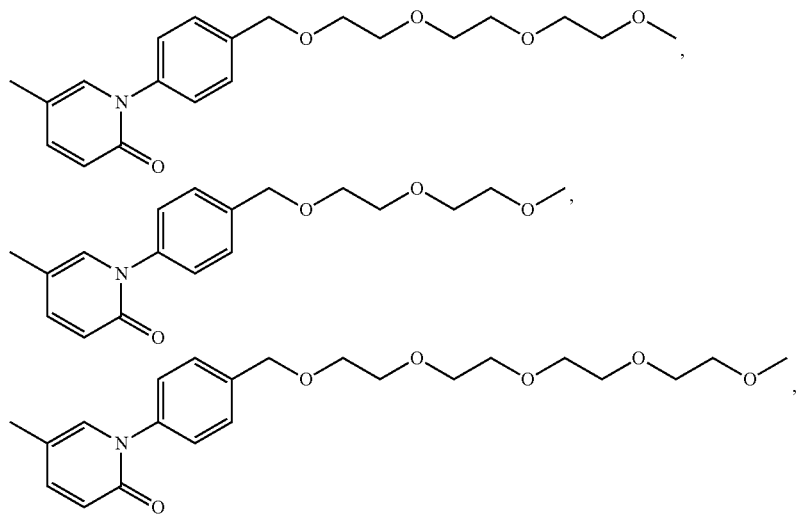

-continued
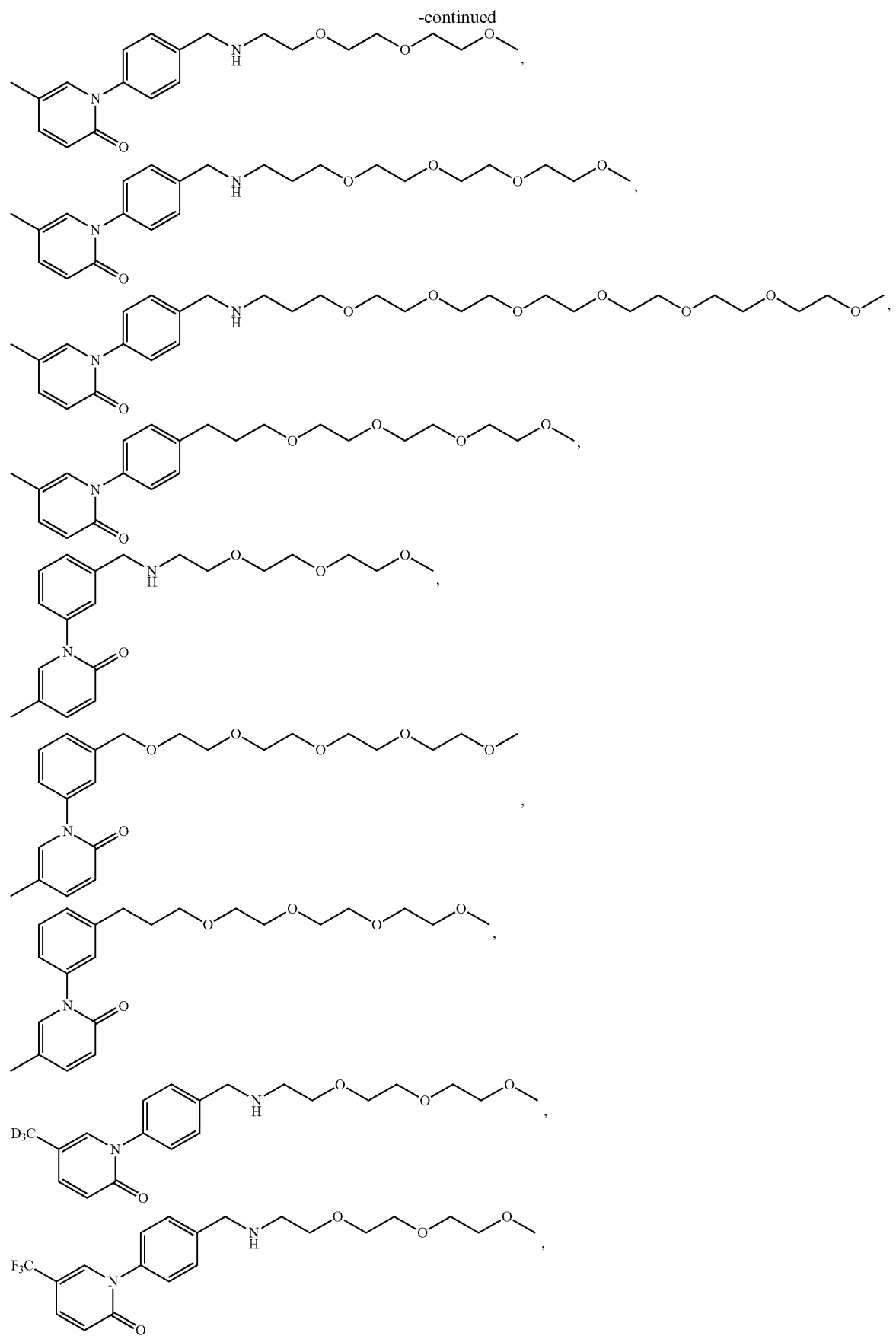

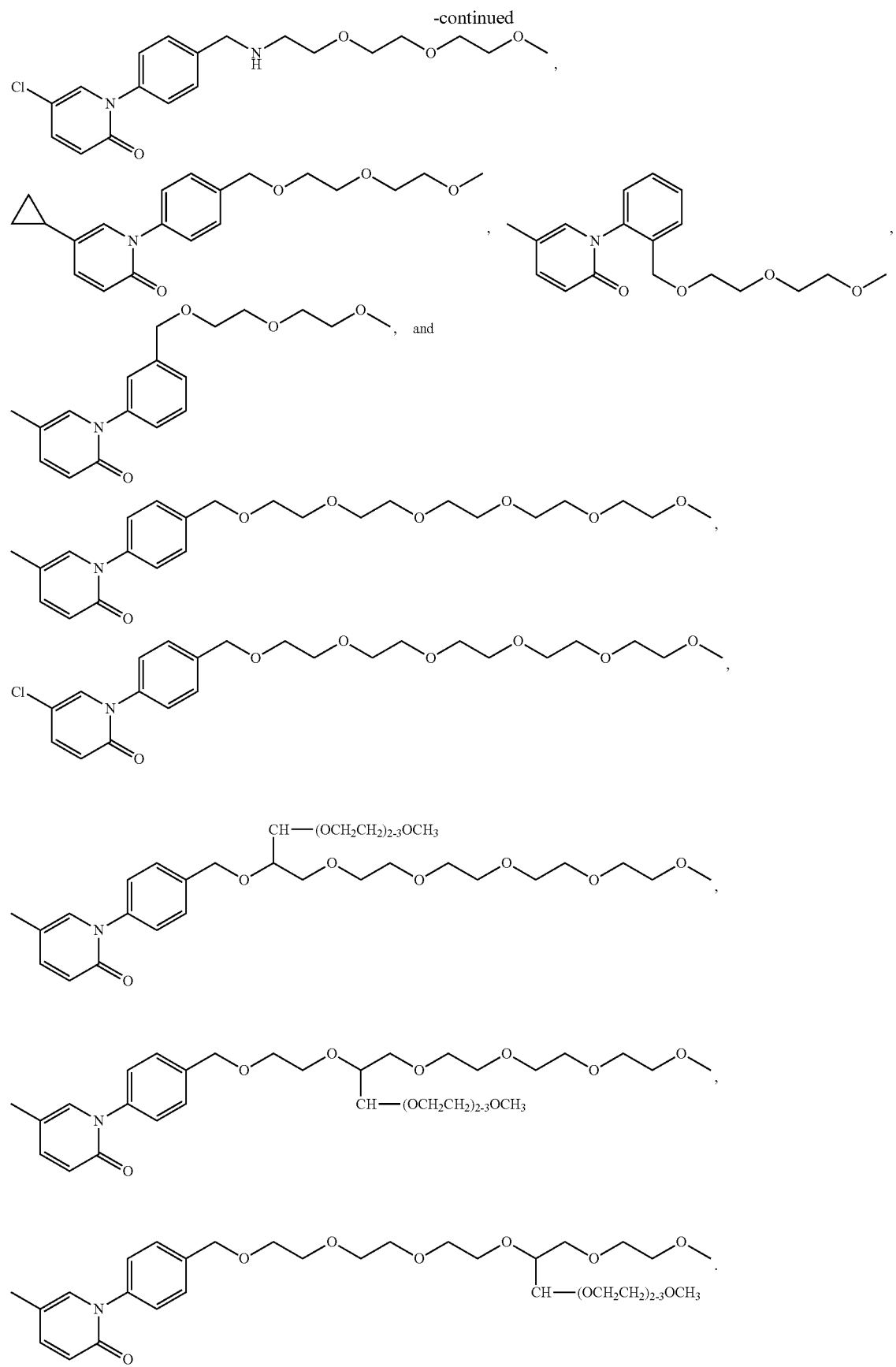

Provided herein are compounds comprising Formula (II):

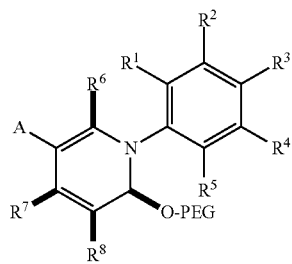

wherein:

R$^1$, R$^2$, R$^3$, R$^4$, R$^5$, R$^6$, R$^7$, and Fe are each independently selected from the group consisting of hydrogen, deuterium or L-X—B;
  wherein L is a linker which comprises a C$_{1-12}$ alkyl; X is O-PEG, NH(CH$_2$)$_m$O-PEG, or S(CH$_2$)$_m$O-PEG; m is an integer from 1-10; wherein PEG is selected the group of mPEG (methoxy polyethylene glycol), linear PEG, branched PEG, multi-arm PEG, and PEG-lipid; B is selected from the group consisting of hydrogen, deuterium, a substituted or unsubstituted C$_1$ to C$_6$ alkyl, a substituted or unsubstituted C$_1$ to C$_6$ alkenyl, a substituted or unsubstituted C$_1$ to C$_6$ alkynyl, a substituted or unsubstituted aryl, and a substituted or unsubstituted heteroaryl, or deuterated versions thereof;

O-PEG is selected the group of mPEG (methoxy polyethylene glycol), linear PEG, branched PEG, multi-arm PEG, and PEG-lipid, wherein the PEG end-cap is selected from the group consisting of hydrogen, deuterium, a substituted or unsubstituted C$_1$ to C$_6$ alkyl, a substituted or unsubstituted C$_1$ to C$_6$ alkenyl, a substituted or unsubstituted C$_1$ to C$_6$ alkynyl, a substituted or unsubstituted aryl, and a substituted or unsubstituted heteroaryl, or deuterated versions thereof;

A is selected from the group consisting of hydrogen, deuterium, halogen, CF$_3$, CD$_3$, CN, OH, OCH$_3$, OR", SR", NR"R", NR"COR", NR"CONR"R", NR"CO$_2$R", COR", CO$_2$R", NOR", NO$_2$, CONR"R", OC(O)NR"R", SO$_2$R", SO$_2$NR"R", NR"SO$_2$R", NR"SO$_2$NR"R", C(O)C(O)R", and C(O)CH$_2$C(O)R", a substituted or unsubstituted C$_1$ to C$_6$ alkyl, a substituted or unsubstituted C$_1$ to C$_6$ alkenyl, a substituted or unsubstituted C$_1$ to C$_6$ alkynyl, a substituted or unsubstituted aryl, and a substituted or unsubstituted heteroaryl; and
  R" may be independently selected from the group consisting of hydrogen, substituted C$_1$-C$_4$ aliphatic moiety, aliphatic moiety containing nitrogen, oxygen, or sulfur, or alternately, two R" moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur.

The PEG or mPEG has a molecular weight ranging from about 100 to about 50,000 Daltons, about 200 to about 50,000 Daltons, about 300 to about 50,000 Daltons, about 400 to about 50,000 Daltons, about 500 to about 50,000 Daltons, about 600 to about 50,000 Daltons, about 700 to about 50,000 Daltons, about 800 to about 50,000 Daltons, about 900 to about 50,000 Daltons, from about 1,000 to about 50,000 Daltons, from about 1,500 to about 50,000, from about 2,000 to about 50,000, from about 2,500 to about 50,000, from about 3,000 to about 50,000, from about 3,500 to about 50,000, from about 4,000 to about 50,000, from about 4,500 to about 50,000, from about 5,000 to about 50,000, from about 5,500 to about 50,000, from about 6,000 to about 50,000, from about 6,500 to about 50,000, from about 7,000 to about 50,000, from about 7,500 to about 50,000, from about 8,000 to about 50,000, from about 8,500 to about 50,000, from about 9,000 to about 50,000, from about 9,500 to about 50,000, from about 10,000 to about 50,000, from about 11,000 to about 50,000, from about 12,000 to about 50,000, from about 13,000 to about 50,000, from about 14,000 to about 50,000 Daltons, from about 15,000 to about 50,000 Daltons, from about 16,000 to about 50,000 Daltons, from about 17,000 to about 50,000 Daltons, from about 18,000 to about 50,000 Daltons, from about 19,000 to about 50,000 Daltons, from about 20,000 to about 50,000 Daltons, from about 30,000 to about 50,000 Daltons, or from about 40,000 to about 50,000 Daltons. In some embodiments the PEG has a molecular weight ranging from about 40 Daltons to about 1,200 Daltons. In some embodiments, the PEG has a molecular weight of less than about 1,000 Daltons. In some embodiments, the PEG has a molecular weight of about 1,000 Daltons.

Dosages of a compound of Formula (I) or Formula (II) can vary between wide limits, depending upon the disease or disorder to be treated, the age and condition of the subject to be treated. In an embodiment where a composition comprising a compound of Formula (I) or Formula (II) is contacted with a sample, the concentration of a compound of Formula (I) or Formula (II) may be from about 0.1 μM to about 40 μM. Alternatively, the concentration of a compound of Formula (I) or Formula (II) may be from about 5 μM to about 25 μM. For example, the concentration of a compound of Formula (I) or Formula (II) may be about 0.1, about 0.25, about 0.5, about 0.6, about 0.7, about 0.8, about 0.9, about 1, about 2.5, about 5, about 6, about 7, about 8, about 9, about 10, about 11, about 12, about 13, about 14, about 15, about 16, about 17, about 18, about 19, about 20, about 21, about 22, about 23, about 24, about 25, about 30, about 35, or about 40 μM. Additionally, the concentration of a compound of Formula (I) or Formula (II) may be greater than 40 μM. For example, the concentration of a compound of Formula (I) or Formula (II) may be about 40, about 45, about 50, about 55, about 60, about 65, about 70, about 75, about 80, about 85, about 90, about 95, or about 100 μM.

In an embodiment where the composition comprising a compound of Formula (I) is administered to a subject, the dose of a compound of Formula (I) or Formula (II) may be from about 0.1 mg/kg to about 500 mg/kg. For example, the dose of a compound of Formula (I) or Formula (II) may be about 0.1 mg/kg, about 0.5 mg/kg, about 1 mg/kg, about 5 mg/kg, about 10 mg/kg, about 15 mg/kg, about 20 mg/kg, or about 25 mg/kg. Alternatively, the dose of a compound of Formula (I) or Formula (II) may be about 25 mg/kg, about 50 mg/kg, about 75 mg/kg, about 100 mg/kg, about 125 mg/kg, about 150 mg/kg, about 175 mg/kg, about 200 mg/kg, about 225 mg/kg, or about 250 mg/kg. Additionally, the dose of a compound of Formula (I) or Formula (II) may be about 300 mg/kg, about 325 mg/kg, about 350 mg/kg, about 375 mg/kg, about 400 mg/kg, about 425 mg/kg, about 450 mg/kg, about 475 mg/kg or about 500 mg/kg.

(c) Components of the Composition

The present disclosure also provides pharmaceutical compositions. The pharmaceutical composition comprises a PFD, PFD derivative, a compound of Formula (I), or a compound of Formula (II), as an active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In each of the embodiments described herein, a composition of the invention may optionally comprise one or more additional drug or therapeutically active agent in addition to the PFD, PFD derivative, compound of Formula (I), or compound of Formula (II). In some embodiments, the additional drug or therapeutically active agent induces anti-inflammatory effects or is capable of decreasing levels of plasma cells and/or B-cells in the subject. In some embodiments, the secondary agent is an antibody. In some embodiments, the secondary agent is not dexpramipexole. In some embodiments, the secondary agent is selected from a corticosteroid, a non-steroidal anti-inflammatory drug (NSAID), an intravenous immunoglobulin, a tyrosine kinase inhibitor, a fusion protein, a monoclonal antibody directed against one or more pro-inflammatory cytokines, a chemotherapeutic agent and a combination thereof. In some embodiments, the secondary agent may be a glucocorticoid, a corticosteroid, a non-steroidal anti-inflammatory drug (NSAID), a phenolic antioxidant, an anti-proliferative drug, a tyrosine kinase inhibitor, an anti IL-5 or an IL5 receptor monoclonal antibody, an anti IL-13 or an anti IL-13 receptor monoclonal antibody, an IL-4 or an IL-4 receptor monoclonal antibody, an anti IgE monoclonal antibody, a monoclonal antibody directed against one or more pro-inflammatory cytokines, a TNF-α inhibitor, a fusion protein, a chemotherapeutic agent or a combination thereof. In some embodiments, the secondary agent is an anti-inflammatory drug. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, curcumin, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, lysofylline, meclofenamate sodium, meclofenamic acid, meclorisone dibutyrate, mefenamic acid, mesalamine, meseclazone, methylprednisolone suleptanate, mom iflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, mepolizumab, prodrugs thereof, and a combination thereof. In some embodiments the tyrosine kinase inhibitor is imatinib. In some embodiments the anti IL-5 monoclonal antibody is mepolizumab or reslizumab. In some embodiments, the IL-5 receptor monoclonal antibody is benralizumab. In some embodiments, the anti IL-13 monoclonal antibody is lebrikizumab or dulipumab. In some embodiments the anti IL-4 monoclonal antibody is dulipumab. In some embodiments, the anti IgE monoclonal antibody is omalizumab. In some embodiments, the TNF-α inhibitor is infliximab, adalimumab, certolizumab pegol, or golimumab. In some embodiments, the secondary agent is a drug used to treat heart failure such as a beta-blocker, an ACE-inhibitor, an angiotensin receptor blocker (ARB), a neprilisine inhibitor or an aldosterone antagonist.

(i) Diluent

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

(ii) Binder

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylam ides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

(iii) Filler

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

(iv) Buffering Agent

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

(v) pH Modifier

In various embodiments, the excipient may be a pH modifier. By way of non-limiting example, the pH modifying agent may be sodium carbonate, sodium bicarbonate, sodium citrate, citric acid, or phosphoric acid.

(vi) Disintegrant

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

(vii) Dispersant

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

(viii) Excipient

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

(ix) Lubricant

In a further embodiment, the excipient may be a lubricant. Non-limiting examples of suitable lubricants include minerals such as talc or silica; and fats such as vegetable stearin, magnesium stearate, or stearic acid.

(x) Taste-Masking Agent

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

(xi) Flavoring Agent

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

(xii) Coloring Agent

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

(d) Administration (i) Dosage Forms

The composition can be formulated into various dosage forms and administered by a number of different means that will deliver a therapeutically effective amount of the active ingredient. Such compositions can be administered orally (e.g. inhalation), parenterally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof. For administration by inhalation, the compounds are delivered in the form of an aerosol spray from pressured container or dispenser which contains a suitable propellant, e.g., a gas such as carbon dioxide, or a nebulizer.

For parenteral administration (including subcutaneous, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising PFD, PFD derivative, a compound of Formula (I), or a compound of Formula (II), is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of PFD, PFD derivative, a compound of Formula (I), or a compound of Formula (II), in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, the PFD, PFD derivative, compound of Formula (I), or compound of Formula (II) may be selectively delivered to a cell by encapsulation in a liposome that fuses with the targeted cell's membrane.

Liposomes may be comprised of a variety of different types of phosolipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying PFD, PFD derivative, a compound of Formula (I), or a compound of Formula (II), may be prepared by any known method of preparing liposomes for drug delivery, such as, for example, detailed in U.S. Pat. Nos. 4,241,046; 4,394,448; 4,529,561; 4,755,388; 4,828,837; 4,925,661; 4,954,345; 4,957,735; 5,043,164; 5,064,655; 5,077,211; and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar lipsomes.

As would be apparent to one of ordinary skill, all of the parameters that govern liposome formation may be varied. These parameters include, but are not limited to, temperature, pH, concentration of PFD, PFD derivative, a compound of Formula (I), or a compound of Formula (II), concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The compound of Formula (I) or Formula (II) may be encapsulated in a microemulsion by any method generally known in the art.

In yet another embodiment, a PFD, PFD derivative, a compound of Formula (I), or a compound of Formula (II), may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

(II) Methods

The present disclosure encompasses a method of modulating B lymphocyte activity in a sample, the method comprising contacting a composition comprising an effective amount of Pirfenidone, a Pirfenidone derivative, a compound of Formula (I), a compound of Formula (II) or combinations thereof. In another aspect, the present disclosure encompasses a method of modulating B lymphocyte activity or provide protection to organs and tissues from acute damage or age associated changes in a subject in need thereof, the method comprising administering to the subject a composition comprising a therapeutically effective amount a compound of Pirfenidone, a Pirfenidone derivative, a compound of Formula (I), a compound of Formula (II) or combinations thereof. In yet another aspect, the present disclosure provides a composition comprising Pirfenidone, a Pirfenidone derivative, a compound of Formula (I), a compound of Formula (II) or combinations thereof, for use in vitro, in vivo, or ex vivo. Suitable compositions comprising PFD, a PFD derivate, or compounds disclosed herein, for instance those described in Section I.

According to an aspect of the invention a pharmaceutical composition comprising a PFD, a PFD derivative, a compound of Formula (I), a compound of Formula (II) or a combination thereof is used for modulating B lymphocyte activity. The method generally comprises contacting a B lymphocyte with a pharmaceutical composition comprising PFD, a PFD derivative, a compound of Formula (I), a compound of Formula (II) or a combination thereof. In some embodiments, the method comprising contacting a B lymphocyte in vivo by administering a pharmaceutical composition comprising PFD, a PFD derivative, a compound of Formula (I), a compound of Formula (II) or a combination thereof to a subject in need thereof. B lymphocyte activity is measured by the activity or expression of genes associated with cytokine-cytokine receptor interaction, B cell receptor signaling pathways, cell adhesion molecules, antigen processing and presentation, MAPK signaling, Toll-like receptor (TLR) signaling, TNF signaling pathway and chemokine receptor signaling pathway. In some embodiments, B cell activity is measured CD86 expression, wherein increased expression of CD86 indicates increased B cell activity. CD86, also known as Cluster of Differentiation 86 and B7-2, is a protein expressed on B cells that provides costimulatory signals necessary for T cell activation and survival. In some embodiments, B cell activity is measured through TIRAP dependent signaling pathways. TIRAP is an adapter protein required for signaling downstream of TLR1/2, TLR2/6, TLR4, and TLR10. In some embodiments, B lymphocyte recruitment to a tissue or organ is measured.

In some embodiments, contacting a B lymphocyte with a pharmaceutical composition comprising PFD, a PFD derivative, a compound of Formula (I), a compound of Formula (II) or a combination thereof results in reduced B lymphocyte activity and/or reduced recruitment of B lymphocytes to an organ or tissue. In some embodiments, B lymphocyte activity or number is reduced in the presence of a pharmaceutical composition comprising PFD, a PFD derivative, a compound of Formula (I), a compound of Formula (II) or a combination thereof, relative to an untreated control. In some embodiments, B lymphocyte activity or number is reduced in the presence of a pharmaceutical composition comprising PFD, a PFD derivative, a compound of Formula (I), a compound of Formula (II) or a combination thereof, relative to an activated B lymphocyte or relative to the number of B lymphocytes in a damaged tissue or organ.

As used herein, the terms "B-lymphocyte" or "B-cell" refer to a lymphocyte. In some embodiments, the terms "B-lymphocyte" or "B-cell" refer to B lymphocytes. In some embodiments, the terms "B-lymphocyte" or "B-cell" refer to a B-cell residing in the bone marrow, in the systemic circulatory system, and/or in organ tissues. In some embodiments, the organ tissue is the heart, the brain, the kidney, the liver, lymph nodes, or combinations thereof.

According to an aspect of the invention a pharmaceutical composition comprising at least one of a PFD, a PFD derivative, a compound of Formula (I), or a compound of Formula (II) described herein is used to protect a subject from development or progression of dysfunction of an organ after acute organ injury. The method generally comprises administering to a subject a pharmaceutical composition comprising a therapeutically effective amount of at least one of a PFD, a PFD derivative, a compound of Formula (I), or a compound of Formula (II). In some embodiments, the subject is administered the composition when organ damage is anticipated, and wherein administration of the composition prevents or slows the progression of organ damage, wherein the organ is selected from the group consisting of heart, liver, kidney, gut, and brain. In some embodiments, the composition is administered to a subject to prevent the effects of acute tissue injury or ischemia. In some embodiments, the composition is administered before organ transplantation in a subject. In some embodiments, the organ is selected form the group consisting of heart, kidney, liver, gut, and brain.

According to another aspect of the invention a pharmaceutical composition comprising at least one of a PFD, a PFD derivative, a compound of Formula (I), or a compound of Formula (II) described herein is used to treat a disorder associated with dysregulated B cell activity. Thus, a PFD, a PFD derivative, a compound of Formula (I), or a compound of Formula (II) as described herein may be used in a method to treat or prevent a B cell disorder. Thus, compositions comprising a PFD, a PFD derivative, a compound of Formula (I), or a compound of Formula (II) of this disclosure are useful in treating B cell disorders. A "B cell disorder", as used herein, is a condition that is characterized by B cell mediated hyperproliferative, inflammatory, or autoimmune diseases. The method generally comprises administering to a subject a pharmaceutical composition comprising a therapeutically effective amount of at least one of a PFD, a PFD derivative, a compound of Formula (I), or a compound of Formula (II).

B cell disorders include disorders characterized by autoantibody production or autoimmune diseases. In non-limiting examples, autoimmune diseases and diseases associated with B cell dysfunction include arthritis, rheumatoid arthritis, juvenile rheumatoid arthritis, osteoarthritis, polychondritis, psoriatic arthritis, psoriasis, dermatitis, polymyositis/dermatomyositis, inclusion body myositis, inflammatory myositis, toxic epidermal necrolysis, systemic scleroderma and sclerosis, CREST syndrome, responses associated with inflammatory bowel disease, Crohn's disease, ulcerative colitis, respiratory distress syndrome, adult respiratory distress syndrome (ARDS), scleroderma, meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), subacute cutaneous lupus erythematosus, discoid lupus, lupus myelitis, lupus cerebritis, juvenile onset diabetes, multiple sclerosis, allergic encephalomyelitis, neuromyelitis optica, rheumatic fever, Sydenham's chorea, immune responses associated with acute and delayed hypersensitivity mediated by cytokines and T-lymphocytes, tuberculosis, sarcoidosis, granulomatosis including Wegener's granulomatosis and Churg-Strauss disease, agranulocytosis, vasculitis (including hypersensitivity vasculitis/angiitis, ANCA and rheumatoid vasculitis), aplastic anemia, Diamond Blackfan anemia, immune hemolytic anemia including autoimmune hemolytic anemia (AIHA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple sclerosis, multiple organ injury syndrome, mysathenia gravis, antigen-antibody complex mediated diseases, anti-glomerular basement membrane disease, anti-phospholipid antibody syndrome, allergic neuritis, Behcet disease, Castleman's syndrome, Goodpasture's syndrome, Lambert-Eaton Myasthenic Syndrome, Reynaud's syndrome, Sjorgen's syndrome, Stevens-Johnson syndrome, solid organ transplant rejection, graft versus host disease (GVHD), pemphigoid bullous, pemphigus, autoimmune polyendocrinopathies, seronegative spondyloarthropathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), Henoch-Schonlein purpura, autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes (also referred to as insulin-dependent diabetes mellitus (IDDM)) and Sheehan's syndrome; autoimmune hepatitis, lymphoid interstitial pneumonitis (HIV), bronchiolitis obliterans (non-transplant) vs NSIP, Guillain-Barre'Syndrome, large vessel vasculitis (including polymyalgia rheumatica and giant cell (Takayasu's) arteritis), medium vessel vasculitis (including Kawasaki's disease and polyarteritis nodosa), polyarteritis nodosa (PAN) ankylosing spondylitis, Berger's disease (IgA nephropathy), rapidly progressive glomerulonephritis, primary biliary cirrhosis, Celiac sprue (gluten enteropathy), cryoglobulinemia, cryoglobulinemia associated with hepatitis, amyotrophic lateral sclerosis (ALS), coronary artery disease, heart failure with reduced ejection fraction, heart failure with preserved ejection fraction, familial Mediterranean fever, microscopic polyangiitis, Cogan's syndrome, Whiskott-Aldrich syndrome and thromboangiitis obliterans.

B-cell cancers include B-cell lymphomas (such as various forms of Hodgkin's disease, non-Hodgkins lymphoma (NHL) or central nervous system lymphomas), leukemias (such as acute lymphoblastic leukemia (ALL), chronic lymphocytic leukemia (CLL), Hairy cell leukemia and chronic myoblastic leukemia), and myelomas (such as multiple myeloma). Additional B cell cancers include small lymphocytic lymphoma, B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma of mucosa-associated (MALT) lymphoid tissue, nodal marginal zone B-cell lymphoma, follicular lymphoma, mantle cell lymphoma, diffuse large B-cell lymphoma, mediastinal (thymic) large B-cell lymphoma, intravascular large B-cell lymphoma, primary effusion lymphoma, Burkitt lymphoma/leukemia, B-cell proliferations of uncertain malignant potential, lymphomatoid granulomatosis, and post-transplant lymphoproliferative disorder.

In certain aspects, a therapeutically effective amount of a composition of the invention may be administered to a subject. Administration is performed using standard effective techniques, including peripherally (i.e. not by administration into the central nervous system) or locally to the central nervous system. Peripheral administration includes but is not limited to oral, inhalation, intravenous, intraperitoneal, intra-articular, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation. The route of administration may be dictated by the disease or condition to be treated. For example, if the disease or condition is COPD or IPF, the composition may be administered via inhalation. Alternatively, is the disease or condition is osteoarthritis, the composition may be administered via intra-articular invention. It is within the skill of one in the art, to determine the route of administration based on the disease or condition to be treated. In a specific embodiment, a composition of the invention is administered orally.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents, and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners.

For therapeutic applications, a therapeutically effective amount of a composition of the invention is administered to a subject. A "therapeutically effective amount" is an amount of the therapeutic composition sufficient to produce a measurable response (e.g., cell death of senescent cells, an anti-aging response, an improvement in symptoms associated with a degenerative disease, or an improvement in symptoms associated with a function-decreasing disorder). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, age, the age-related disease or condition, the degenerative disease, the function-decreasing disorder, the symptoms, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine.

The frequency of dosing may be daily or once, twice, three times, or more per day, per week or per month, as needed as to effectively treat the symptoms. The timing of administration of the treatment relative to the disease itself and duration of treatment will be determined by the circumstances surrounding the case. Treatment could begin immediately, such as at the site of the injury as administered by emergency medical personnel. Treatment could begin in a hospital or clinic itself, or at a later time after discharge from the hospital or after being seen in an outpatient clinic. Duration of treatment could range from a single dose administered on a one-time basis to a life-long course of therapeutic treatments.

Typical dosage levels can be determined and optimized using standard clinical techniques and will be dependent on the mode of administration.

A subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the subject is a human.

Definitions

When introducing elements of the present disclosure or the preferred aspects(s) thereof, the articles "a," "an," "the," and "said" are intended to mean that there are one or more of the elements. The terms "comprising," "including," and "having" are intended to be inclusive and mean that there may be additional elements other than the listed elements.

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry," Thomas Sorrell, University Science Books, Sausalito: 1999, and "March's Advanced Organic Chemistry," 5$^{th}$ Ed., Smith, M. B. and March, J., eds. John Wiley & Sons, New York: 2001, the entire contents of which are hereby incorporated by reference.

The term "alkyl" as used herein alone or as part of a group refers to saturated monovalent hydrocarbon radicals having straight or branched hydrocarbon chains or, in the event that at least 3 carbon atoms are present, cyclic hydrocarbons or combinations thereof and contains 1 to 20 carbon atoms (C.sub.1-20alkyl), suitably 1 to 10 carbon atoms (C.sub.1-10alkyl), preferably 1 to 8 carbon atoms (C.sub.1-8alkyl), more preferably 1 to 6 carbon atoms (C.sub.1-4alkyl), and even more preferably 1 to 4 carbon atoms (C.sub.1-4alkyl). Examples of alkyl radicals include methyl, ethyl, propyl, isopropyl, n-butyl, isobutyl, sec-butyl, tert-butyl, pentyl, isoamyl, hexyl, cyclopropyl, cyclobutyl, cyclopentyl, cyclohexyl, and the like.

The term "alkenyl" as used herein alone or as part of a group refers to monovalent hydrocarbon radicals having a straight or branched hydrocarbon chains having one or more double bonds and containing from 2 to about 18 carbon atoms, preferably from 2 to about 8 carbon atoms, more preferably from 2 to about 5 carbon atoms. Examples of suitable alkenyl radicals include ethenyl, propenyl, alkyl, 1,4-butadienyl, and the like.

The term "alkynyl" as used herein alone or as part of a group refers to monovalent hydrocarbon radicals having a straight or branched hydrocarbon chains having one or more triple bonds and containing from 2 to about 10 carbon atoms, more preferably from 2 to about 5 carbon atoms. Examples of alkynyl radicals include ethynyl, propynyl, (propargyl), butyny,1 and the like.

The term "aryl" as used herein, alone or as part of a group, includes an organic radical derived from an aromatic hydrocarbon by removal of one hydrogen, and includes monocyclic and polycyclic radicals, such as phenyl, biphenyl, naphthyl.

The term "alkoxy" as used herein, alone or as part of a group, refers to an alkyl ether radical wherein the term alkyl is as defined above. Examples of alkyl ether radical include methoxy, ethoxy, n-propoxy, isopropoxy, n-butoxy, isobutoxy, sec-butoxy, tert-butoxy, and the like.

The term "cycloalkyl" as used herein, alone or in combination, means a saturated or partially saturated monocyclic, bicyclic or tricyclic alkyl radical wherein each cyclic moiety contains from about 3 to about 8 carbon atoms, more preferably from about 3 to about 6 carbon atoms. Examples of such cycloalkyl radicals include cyclopropyl, cyclobutyl, cyclopentyl, cyclohexyl, and the like.

The term "cycloalkylalkyl" as used herein, alone or in combination, means an alkyl radical as defined above which is substituted by a cycloalkyl radical as defined above. Examples of such cycloalkylalkyl radicals include cyclopropylmethyl, cyclobutyl-methyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, cyclohexylbutyl, and the like.

The term "substituted" as used herein means that one or more of the hydrogen atoms bonded to carbon atoms in the chain or ring have been replaced with other substituents. Suitable substituents include monovalent hydrocarbon groups including alkyl groups such as methyl groups and monovalent heterogeneous groups including alkoxy groups such as methoxy groups.

The term "unsubstituted" as used herein means that the carbon chain or ring contains no other substituents other than carbon and hydrogen.

The term "branched" as used herein means that the carbon chain is not simply a linear chain. "Unbranched" means that the carbon chain is a linear carbon chain.

The term "saturated" as used herein means that the carbon chain or ring does not contain any double or triple bonds. "Unsaturated" means that the carbon chain or ring contains at least one double bond. An unsaturated carbon chain or ring may include more than one double bond.

The term "hydrocarbon group" means a chain of 1 to 25 carbon atoms, suitably 1 to 12 carbon atoms, more suitably 1 to 10 carbon atoms, and most suitably 1 to 8 carbon atoms. Hydrocarbon groups may have a linear or branched chain structure. Suitably the hydrocarbon groups have one branch.

The term "carbocyclic group" means a saturated or unsaturated hydrocarbon ring. Carbocyclic groups are not aromatic. Carbocyclic groups are monocyclic or polycyclic. Polycyclic carbocyclic groups can be fused, spiro, or bridged ring systems. Monocyclic carbocyclic groups contain 4 to 10 carbon atoms, suitably 4 to 7 carbon atoms, and more suitably 5 to 6 carbon atoms in the ring. Bicyclic carbocyclic groups contain 8 to 12 carbon atoms, preferably 9 to 10 carbon atoms in the rings.

The term "heteroatom" means an atom other than carbon e.g., in the ring of a heterocyclic group or the chain of a heterogeneous group. Preferably, heteroatoms are selected from the group consisting of sulfur, phosphorous, nitrogen and oxygen atoms. Groups containing more than one heteroatom may contain different heteroatoms.

The term "heterocyclic group" means a saturated or unsaturated ring structure containing carbon atoms and 1 or more heteroatoms in the ring. Heterocyclic groups are not aromatic. Heterocyclic groups are monocyclic or polycyclic. Polycyclic heteroaromatic groups can be fused, spiro, or bridged ring systems. Monocyclic heterocyclic groups contain 4 to 10 member atoms (i.e., including both carbon atoms and at least 1 heteroatom), suitably 4 to 7, and more suitably 5 to 6 in the ring. Bicyclic heterocyclic groups contain 8 to 18 member atoms, suitably 9 or 10 in the rings.

The terms "Isomer," "isomeric form," "stereochemically isomeric forms," or "stereoisomeric forms," as used herein, defines all possible isomeric as well as conformational forms, made up of the same atoms bonded by the same sequence of bonds but having different three-dimensional structures which are not interchangeable, which compounds or intermediates obtained during said process may possess. Unless otherwise mentioned or indicated, the chemical designation of a compound encompasses the mixture of all possible stereochemically isomeric forms which said compound may possess. Said mixture may contain all diastereoisomers, epimers, enantiomers, and/or conformers of the basic molecular structure of said compound. More in particular, stereogenic centers may have the R- or S-configuration, diastereoisomers may have a syn- or anti-configuration, substituents on bivalent cyclic saturated radicals may have either the cis- or trans-configuration and alkenyl radicals may have the E or Z-configuration. All stereochemically isomeric forms of said compound both in pure form or in admixture with each other are intended to be embraced within the scope of the present invention.

Specific embodiments disclosed herein may be further limited in the claims using "consisting of" or "consisting essentially of" language, rather than "comprising". When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

As various changes could be made in the above-described materials and methods without departing from the scope of the invention, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Figure 1A:
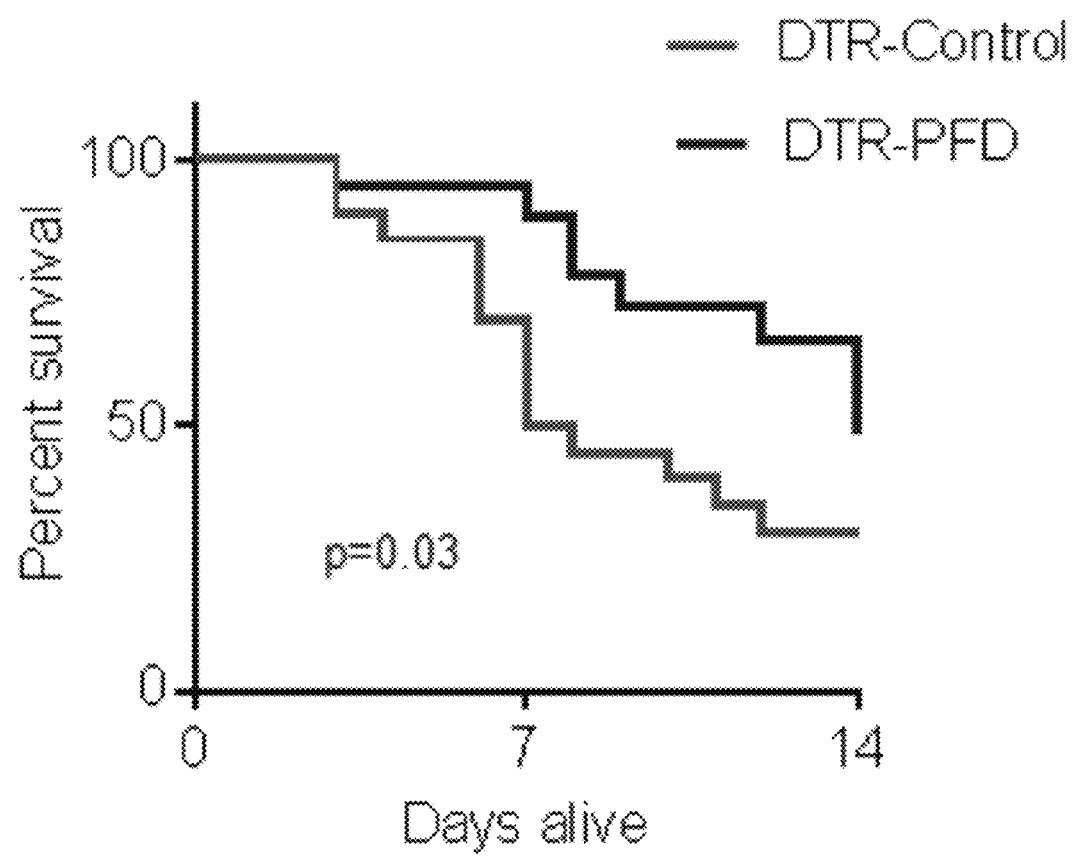
FIG. 1A, FIG. 1B, FIG. 1C and FIG. 1D illustrates the effect of Pirfenidone on mortality and cardiac myocyte cell death after DT treatment. Mice expressing the diphtheria toxin receptor (DTR) in the myocardium were exposed to diphtheria toxin and fed either chow enriched with Pirfenidone (DTR-PFD) or regular chow (DTR-control).
Figure 1B:
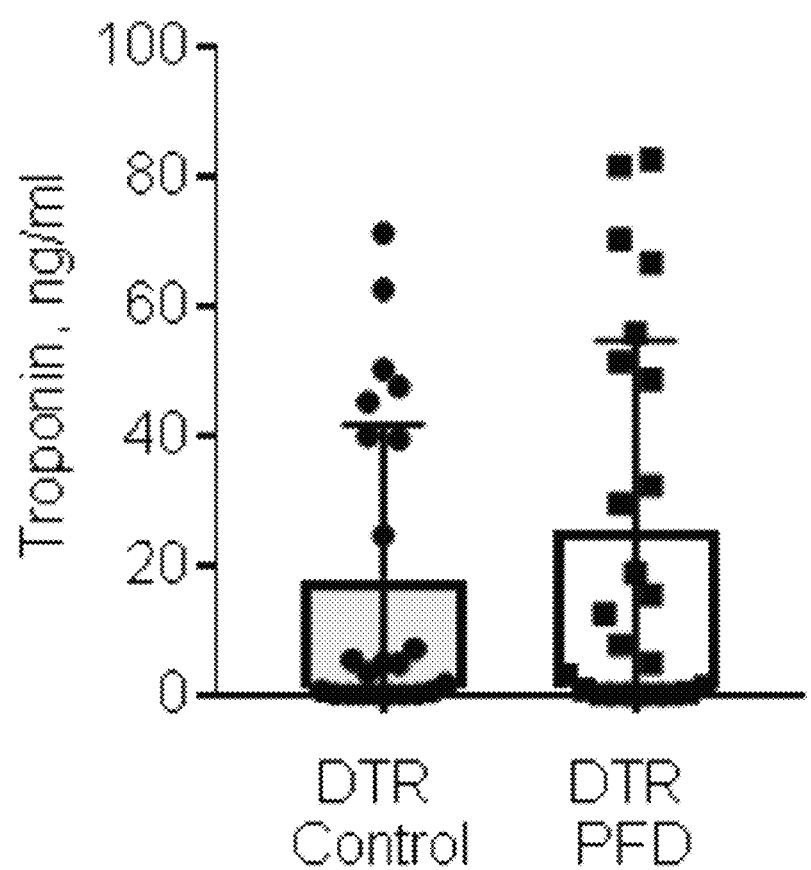
Figure 1C:
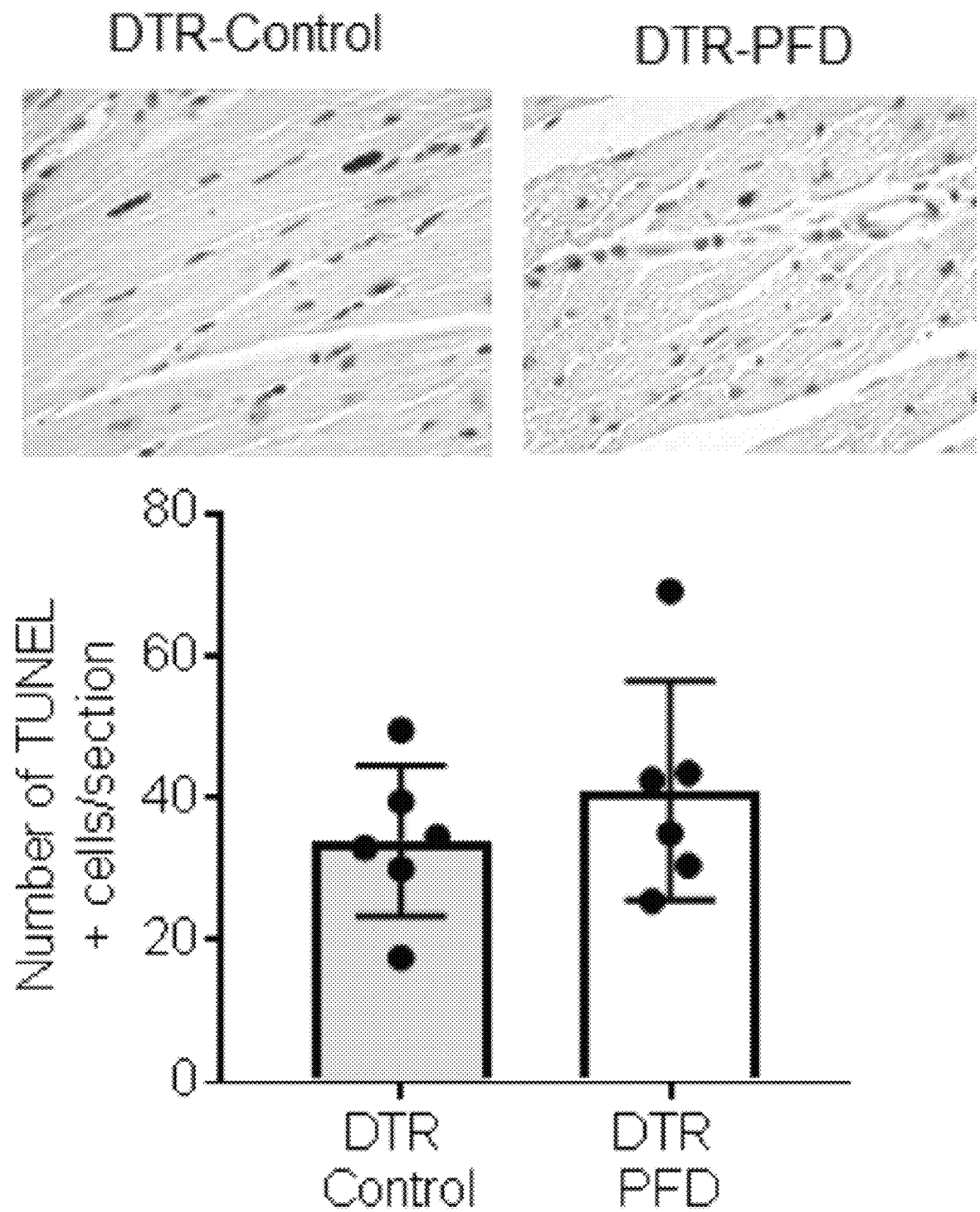
Figure 1D:
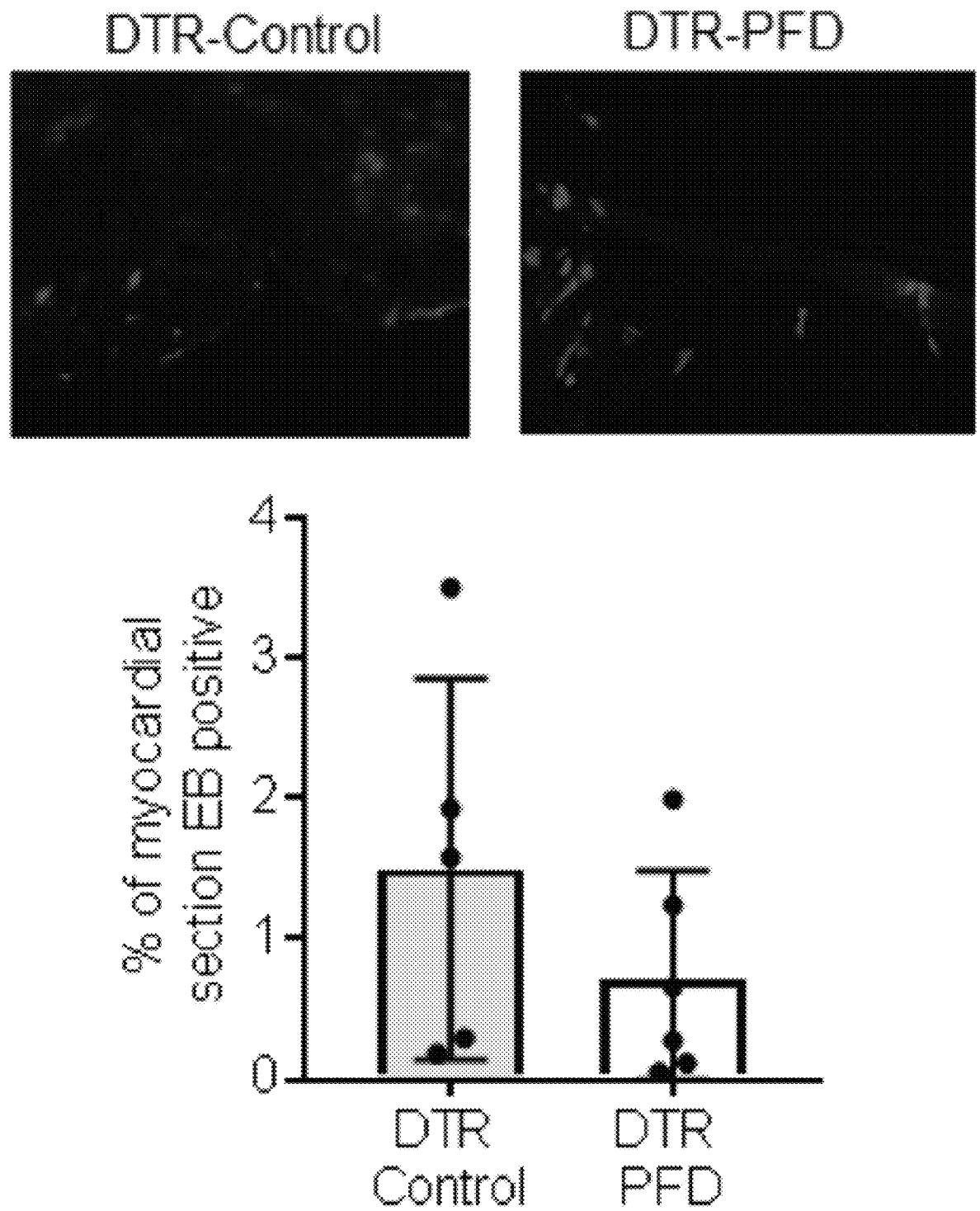

Example 1: Pirfenidone Improves Survival after Diphtheria Toxin Mediated Acute Myocardial Injury To determine the effects of Pirfenidone on acute myocardial injury we employed the diphtheria toxin (DT) cardiac myocyte cell ablation model, as previously described (13). Adult Rosa26-DT Mlc2v-Cre mice injected with DT develop LV dysfunction and remodeling, and associated increased mortality within 2 weeks (13). As shown in FIG. 1A, the survival of Pirfenidone treated mice was significantly improved when compared to untreated DT-treated littermate controls (p=0.03). The protective effect of Pirfenidone was not secondary to a significant attenuation in DT-induced cardiac myocyte cell death, insofar as there were no significant differences in serum troponin levels (p=0.34, FIG. 1B), the prevalence of cardiac myocyte apoptosis (p=0.39, FIG. 1C), and extent of Evans Blue dye uptake (p=0.26, FIG. 1D) between the mice fed normal chow and mice fed chow with Pirfenidone.

Example 2: Pirfenidone Reduces Cardiac CD19+ B Lymphocytes Following Diphtheria Toxin-Mediated Acute Myocardial Injury Given that treatment with Pirfenidone did not reduce cardiac myocyte necrosis or apoptosis, we asked whether Pirfenidone improved survival by modulating the innate immune response to acute cardiac injury. Accordingly, we performed FACS analysis 4 days after DT injection. The gating strategy for this FACS analysis is shown in FIG. 2A. In preliminary control studies, we determined that treatment with Pirfenidone for 1 week in naïve WT hearts had no significant effect on the number of CD45+ cells/mg tissue (p=0.53), Ly6G+ neutrophils (p=0.82), Ly6C+CD64 low/− monocytes (p=0.81), CD64+Ly6Clow/− macrophages (p=0.82) or CD19+ B-lymphocytes (p=0.94; FIG. 2B and FIG. 2C).

As shown in FIG. 2, there were no significant differences in the DT-injured hearts from mice treated with Pirfenidone chow or normal chow with respect to the number of myocardial CD45+ cells (p=0.8, FIG. 2D), Ly6G+ neutrophils (p=0.27, FIG. 2E), Ly6C+ CD64$^{low}$/− monocytes (p=0.15 FIG. 2E) and Ly6C$^{low}$/− CD64+ macrophages (p=0.9, FIG. 2B). The adult heart macrophage pool consists of resident and recruited cells, the latter of which have been associated with adverse LV remodeling following injury. These subpopulations are largely divided by the expression of CCR2 and MHC-II (13, 14). Therefore, we further characterized the macrophage populations in control and Pirfenidone-treated and animals. As shown in FIG. 2F, and FIG. 2G there was no significant difference in the percentage of MHC-IIhighCCR2low (p=0.43), MHC-IIhighCCR2high (p=0.36), MHC-IIlowCCR2high (p=0.21), MHC-IIlowCCR2low (p=0.11) macrophage subsets in the presence and absence of treatment with Pirfenidone. Despite the lack of differences in cardiac myeloid populations after damage, we did observe that treatment with Pirfenidone resulted in >3-fold reduction in the percentage of CD19+ myocardial B lymphocytes following DT-injury (p=0.02, FIG. 2E) when compared to mice that were fed normal chow.

Example 3: Pirfenidone Reduces Adverse LV Remodeling and Cardiac CD19+ B Lymphocytes After Closed-Chest Ischemia-Reperfusion Injury To determine the effects of Pirfenidone in a more pathophysiologically relevant model of cardiac injury, we subjected control mice and Pirfenidone-treated mice to closed chest ischemia (90 minutes) reperfusion (I/R) injury, as previously described (15). As shown in FIG. 3A, there was no difference (p=0.68) in the area at risk in control and Pirfenidone-treated animals, as determined by the segmental wall motion score index (SWMSI). Treatment with Pirfenidone resulted in a significant decrease in the heart-weight-to-tibia length ratio (FIG. 3B and FIG. 3C) and LV mass measured by 2-D echocardiography (p=0.03, FIG. 3D) when compared to control mice. Consistent with these findings, we observed a significant (p=0.02) decrease in LV end-diastolic volumes (FIG. 3E) in Pirfenidone treated animals when compared to control animals, whereas there was a trend (p=0.08) towards improvement in LVEF in the treatment group (FIG. 3F). FIG. 3G shows representative Masson's trichrome staining in control and Pirfenidone-treated animals, whereas FIG. 3H summarizes the results of group data. As shown in FIG. 3H, there was no significant difference (p=0.4) in the percentage of myocardium exhibiting collagen staining with Masson's at 2 weeks, when the Pirfenidone chow mice were compared to the mice fed normal chow. The amount of trichrome staining in the myocardium of pirfenidone treated mice was not significantly different from that of control mice. Pirfenidone treatment did not reduce myocardial fibrosis after ischemia-reperfusion injury.

As the preceding experiments examined the effect of pre-treatment with Pirfenidone prior to I/R injury, we sought to determine whether the acute administration of Pirfenidone was sufficient to influence LV remodeling after I/R-injury. We therefore treated mice with intravenous Pirfenidone or diluent soon after reperfusion injury, followed by i.p. injections for 1 day and oral Pirfenidone in the chow for 14 days. FIG. 4A shows that the area at risk was not different (p=0.47) in the control and Pirfenidone-treated animals. However, the salient finding shown by FIG. 4A is that acute administration of Pirfenidone significantly (p=0.015) reduced the heart-weight/tibia length ratio (p=0.015; FIG. 4B), LV mass by 2-D echocardiography (p=0.029; FIG. 4D) and LV end-diastolic volume (p=0.037; FIG. 4E), when compared to diluent treated control mice.

Example 4: Pirfenidone Modulates Subsets of Cardiac B Lymphocytes Following Cardiac Injury To further interrogate the effects of Pirfenidone on cardiac B lymphocytes, we first analyzed the surface antigens of cardiac B cells using known markers of B lymphocytic subtypes. The gating strategy that was used is illustrated in FIG. 5A and staining of splenic B lymphocytes is provided for reference in FIG. 5B. As shown in FIG. 5, the majority of CD19+ cardiac B cells in the uninjured adult heart were CD19+ CD11b−. Further characterization of this population revealed that they were IgD+ and IgMlow/− CD21− CD23− CD11c−, (FIG. 5A). Approximately 10% of the resident cardiac B cells in uninjured hearts were CD19+CD11b+. This population of cells was predominately CD5− IgM+, which is characteristic of B1b lymphocytes, whereas a smaller percentage was CD5+ IgM+, which is characteristic of B1a lymphocytes (16) (FIG. 5C).

We next analyzed B cell profiles in the presence or absence of Pirfenidone in the DT-induced injury model and the closed chest I/R injury model. As shown in FIG. 4, in both models of cardiac injury, the relative ratio of CD19+ CD11b− cells to B1 cells on day 4 after cardiac injury remained unchanged relative to naïve hearts. In the DT-injury hearts (day 4) there was a small but non-significant (FIG. 5D) increase in the number of CD19+ cells/mg of cardiac tissue (p=0.09) and CD19+CD11b+ cells/mg of cardiac tissue (p=0.14), but no change in the number of CD19+CD11b− cells/mg of cardiac tissue (p=0.96) when compared to naïve hearts. In contrast there was a significant 2-fold increase in CD19+ (p<0.001) and CD19+CD11b− (p<0.001) cells at the same time point following I/R-injury (FIG. 5E). In the DT-injury cardiac myocyte ablation model, the Pirfenidone treated animals had significantly fewer (p<0.01) CD19+ cells/mg of tissue, with a significant (p=0.04) reduction in subset of CD19+CD11b− cells (FIG. 5D). We observed very similar changes in the closed-chest I/R injury model, in which Pirfenidone treatment resulted in a significant (p<0.001) reduction in CD19+ lymphocytes on day 4 post I/R, as well as a significant (p<0.001) reduction in the subset of CD19+CD11b− B lymphocytes (FIG. 5E).

Example 5: The Cardioprotective Effect of Pirfenidone is Mediated by B-Lymphocytes Viewed together, the above results suggest that the cardioprotective effects of Pirfenidone may be mediated, at least in part, by cardiac B lymphocytes. To test this hypothesis, we depleted native B cells using a commercially available anti CD20 antibody, and then repeated the closed-chest I/R studies in the presence and absence of Pirfenidone. Given that the mice were instrumented 7 days prior to I/R injury in the closed-chest model, we injected the mice with anti-CD20 antibody at the time of instrumentation. The efficiency of anti-CD20 antibody B cell depletion was assessed 8 days post-anti-CD20 injection (i.e., at the time that I/R injury is performed) and on day 12 post-injection (i.e. day 4 post I/R). As shown in FIG. 6A and FIG. 6B, a single injection of anti-CD20 antibody ablated over 99% of splenic B cells and cardiac B cells by day 8. We noticed that the number of cardiac B cells began to recover on day 4 post-I/R injury (i.e. day 12 post-injection). However, the total number of B cells remained less than 10% that of untreated controls (FIG. 6C). Notably, while post I/R injury B cell depletion significantly reduced (p<0.01) the number of CD19+CD11b− cells, it did not significantly (p=0.2) reduce the total number of CD19+CD11b+ cells (FIG. 6C). However, when we examined CD19+CD11b+ subsets, treatment with the anti-CD20 antibody did significantly (p=0.05) reduce the number of B1b lymphocytes, whereas it had no effect on the number of cardiac B1a lymphocytes (p=0.58; FIG. 6C). There was no significant difference in the heart-weight-to-tibia length ratio (p=0.75; FIG. 6E), LV mass (p=0.21, FIG. 6G), LV end-diastolic volume (p=0.40, FIG. 6H), LVEF (p=0.15, FIG. 6I) or percentage of trichrome positive myocardium (p=0.43, FIG. 6J-6K) between the B-cell depleted mice and B-cell depleted+Pirfenidone treated mice 2 weeks after I/R injury. Thus, the cardioprotective effects of Pirfenidone following I/R injury were B cell dependent.

Example 6: LPS Induced Expression of CD86 is Reduced in the Presence of Pirfenidone B lymphocytes from the peritoneum (FIG. 7A-7B) and spleen (FIG. 8A-8B) were cultured for 24 hours with or without LPS (a TLR agonist). The groups cultured with or without LPS stimulation, were further divided into groups with or without 0.5% pirfenidone (Groups: Control, Control+0.5% pirfenidone, LPS, and LPS+0.5% pirfenidone). LPS increased the expression of the costimulatory molecule CD86 on B cells. This induction was significantly reduced in the presence of pirfenidone.

Example 7: Pirfenidone Reduced Upregulation of CD86 on CD19+ Cells In Vivo in DTR Treated Mice In this experiment DTR mice (described in Example 1) were fed control or 0.5% pirfenidone supplemented chow, and cardiac B lymphocytes stained for CD19 and CD86 and analyzed by flow cytometry, at day 4 post-DTR treatment. This experiment included animals with severe injury (troponin>10). Treatment with pirfenidone reduced the expression of CD86 on B lymphocytes (FIG. 9A-9B), confirming in vivo the in vitro finding of Example 6.

Example 8: Pirfenidone Modulates B Cell Activation Through a TIRAP Dependent Signaling Pathway The observation that B cell depletion abrogated the salutary effects of Pirfenidone suggested that the beneficial effects Pirfenidone were not necessarily mediated by decreasing the number of B cells following tissue injury, and raised the intriguing possibility that Pirfenidone might be modulating the response of B cells to tissue injury. To gain insight into the mechanism(s) responsible for the immunomodulatory effects of Pirfenidone, we performed transcriptional profiling on CD19+CD11b+ and CD19+CD11b− cardiac lymphocytes that were FACS sorted from naïve, DT-injured mice fed normal chow, and DT-injured mice treated with Pirfenidone chow. As shown in FIG. 10 principal component analysis of the transcriptome of cardiac B cells suggested that the mRNAs for the CD19+CD11b+ (FIG. 10A) and CD19+CD11 b− (FIG. 10B) cells from DT-injured hearts had a profile that was distinct from cells from naïve hearts. Importantly, the transcriptional profile of the Pirfenidone treated DT-injured mice clustered between the profile of the naïve and the untreated hearts, suggesting that Pirfenidone modulated the changes in B lymphocyte gene expression that were provoked by cardiac injury. KEGG pathway analysis of mRNAs differentially expressed between DT and naïve hearts>2 fold, FDR<0.05, identified 6 pathways that were enriched in the CD19+CD11b+ lymphocytes from the DT hearts (FIG. 10C): hematopoietic cell lineage (p=1×10-5), cytokine-cytokine receptor interaction (p=3×10-3), B cell receptor signaling pathway (p=1×10-3), cell adhesion molecules (p=0.04), antigen processing and presentation (p=0.04), and MAPK signaling (p=0.05). These pathways were not activated in the CD19+CD11b+ lymphocytes isolated from the DTR+PFD hearts (FIG. 10C), demonstrating that Pirfenidone alters the gene expression changes in B cells that are driven by cardiac injury. As shown in FIG. 10D, the KEGG pathway analysis identified 5 pathways in CD19+CD11b− cells: two pathways that were also activated in the CD19+CD11b+, specifically hematopoietic cell lineage (p=2×10-3) and cytokine-cytokine receptor interaction (p=1×10-3), as well as 3 unique pathways, specifically Toll-like receptor (TLR) signaling (p=1×10-3), TNF signaling pathway (p=7×10-3) and chemokine receptor signaling pathway (p=0.02). With the exception of the hematopoietic cell lineage pathway, none of these pathways was significantly enriched in the CD19+CD11 b− lymphocytes isolated from the DTR+PFD hearts (FIG. 10D). The gene lists for each of these KEGG pathways are provided in Supplementary Table 1 and Table 2. Viewed together, these studies suggest that myocardial CD19+CD11b+ and CD19+CD11b− lymphocytes share common biological responses, but also have unique biological responses to tissue injury, and that both these common and unique responses to cardiac injury are modulated by Pirfenidone.

Noting that prior studies have shown that B cells are activated by engagement of TLR by damage-associated molecular patterns (DAMPs) released by necrotic cells (17), and noting that TLR signaling was present in CD19+CD11b− lymphocytes sorted from DT injured animals but absent in the same cells sorted from DT injured animals treated with Pirfenidone, we focused our in vitro studies on CD19+ cells using lipolysaccharide (a classic TLR4 agonist and a T-independent antigen), as well as necrotic cardiac cell extracts, which we and others have shown signal through TLR4 (18). Based on a prior study which showed that activation of TLR signaling was a strong inducer of the co-stimulatory molecule CD86 in cultured B cells (19), we used upregulation of CD86 as a marker of B cell activation. As shown in FIG. 10E, stimulation of PDICs with LPS or cytosolic extracts from necrotic cells provoked a robust (p<0.001 for both) increase in the CD19+ CD86high lymphocytes. Importantly, the number of CD19+ CD86high was significantly attenuated (p<0.001 for both) by Pirfenidone. To further explore the role of TLR mediated signaling, we repeated these experiments in PDICs obtained from thioglycolate-stimulated TIRAP−/− mice. As shown in FIG. 10F, necrotic cytosolic extracts did not provoke a significant increase in the percentage of CD19+ CD86high lymphocytes, whereas LPS stimulation resulted in a significant increase in the percentage of CD19+ CD86high lymphocytes (p<0.001), albeit to a lesser extent than was observed in PDICs from TIRAP+/+ mice. Notably, treatment with Pirfenidone resulted in a small but significant (p<0.001) decrease in CD19+ CD86high lymphocytes in LPS simulated cultures. These findings suggest that, in the context of a mixed population of inflammatory cells, necrotic cytosolic extracts modulate expression of co-stimulatory molecules on B cells through a TIRAP dependent mechanism, whereas LPS modulates expression of co-stimulatory molecules on B cells through a mechanism that is TIRAP independent. Importantly, both mechanisms were sensitive to treatment with Pirfenidone (FIG. 10E and FIG. 10F).

We next sought to determine whether the response of B cells to necrotic cytosolic extracts and LPS were cell autonomous, by repeating the above in vitro experiments in purified B lymphocytes harvested from the spleen. Interestingly, while the effect of LPS on purified B cells was very similar to that observed on PDICs, the effect of necrotic cytosolic extracts was greatly attenuated. As shown in FIG. 10G, LPS provoked a significant (p<0.001) increase in CD19+ CD86high cells that was partially sensitive to inhibition with Pirfenidone. In contrast, necrotic cytosolic extracts induced a small, non-statistically significant (p=0.62) upregulation of CD19+ CD86high B cells when compared to diluent treated cells (FIG. 10G). Similar results were obtained in splenic B lymphocytes from TIRAP−/− animals (FIG. 10H). Viewed together, these findings suggest that the B cell response to LPS and its modulation by Pirfenidone are cell-autonomous, and are mediated, at least in part, through TIRAP-dependent signaling. In contrast, the response of B cells to necrotic cell extracts and the immunomodulatory effects of Pirfenidone are non-cell autonomous, which suggest that they are likely to be context- and tissue-dependent.

To determine whether our findings with respect to activation of CD19+ B cells in vitro were relevant in vivo, we measured the number of myocardial CD19+ CD86high B cells isolated from the hearts of mice from the DT-injury model and the closed chest I/R-model in the presence and absence of Pirfenidone. As shown in FIG. 10I, treatment with Pirfenidone was associated with a significant (p<0.04) decrease in the number of myocardial CD19+CD86high B lymphocytes in the DT-injury model and FIG. 10J shows that treatment with Pirfenidone was associated with a significant (p<0.03) decrease in the number of myocardial CD19+ CD86high following I/R injury.

Discussion of Examples 1-8

Provided herein are the cardioprotective effects of Pirfenidone, a small molecule that is FDA-approved for the treatment of idiopathic pulmonary fibrosis, and evidence that Pirfenidone exerts beneficial effects in the heart through a unique mechanism that involves immune modulation of the cardiac B lymphocyte response to tissue injury. The following lines of evidence support this statement. First, treatment with Pirfenidone resulted in improved survival in a genetic model of cardiac myocyte injury. Notably, the improved survival was not secondary to a decrease in apoptotic or necrotic cardiac myocyte cell death (FIG. 1). Moreover, the improved survival was not secondary to decreased influx of Ly6G+ neutrophils, Ly6C+CD64low/− monocytes, CD64+ Ly6Clow/− macrophages. Rather, we observed a significant decrease in the number of CD19+ lymphocytes in the heart following Pirfenidone treatment (FIG. 2). Second, treatment with Pirfenidone significantly reduced cardiac remodeling after closed chest I/R injury, as demonstrated by a decrease in the heart weight-to-body ratio, LV mass and LV end diastolic volume (FIG. 3). Importantly, the salutary effects of Pirfenidone were present whether animals were pre-treated with the drug or it was administered after I/R injury. The attenuation in LV remodeling was not secondary to decreased influx of Ly6G+ neutrophils, Ly6C+ CD64low/− monocytes or CD64+ Ly6Clow/− macrophages. Similar to the observations made in the DT-injury model, a significant decrease in CD19+ lymphocytes in the heart following Pirfenidone treatment. Remarkably, B cell depletion with anti-CD20 antibody attenuated the cardioprotective effects of Pirfenidone, suggesting that although the effects of Pirfenidone were B cell dependent, they were not necessarily mediated by decreasing the number of B cells in the injured heart. Third, treatment with Pirfenidone altered the biological response to tissue injury of myocardial CD19+ CD11b+ lymphocytes and of a novel population of CD19+ CD11b− CD23− CD21− IgMlow IgDhigh lymphocytes in vivo, as well as decreased the expression CD86 on B cells in vitro and in vivo. While our data does not exclude an effect of Pirfenidone on other cell types, viewed together the above observations suggest that Pirfenidone is cardioprotective through a unique mechanism that involves immune modulation of myocardial B cells subsets. Although we did not observe an anti-fibrotic effect of Pirfenidone after I/R injury, as has been reported previously by some (4, 5, 7, 9-12), but not all groups (8), this discrepancy may be secondary to differences in the experimental models used and the duration and/or doses of Pirfenidone that were used.

Myocardial B Lymphocytes in Health and Disease

Recent studies have shown that several discrete populations of leukocytes reside in the normal adult murine myocardium. Antigen-presenting mononuclear cells (CD11b+ CD11c+ F4/80+, MHCII+) represent the most prominent population, followed by B cells, monocytes and T cells (20). Although there has been tremendous recent interest in the role of macrophages, dendritic cells and T-cells in the heart, comparatively less is known about the role of B cells. Very little is known about the composition of myocardial B cells in naïve hearts. Ramos et al have shown that the naïve adult murine myocardium harbors two populations of B220+ (CD45R) lymphocytes, a larger population of IgMhigh IgDlow cells and a smaller population of IgMlow IgDhigh cells (21); however, neither the ontology nor functional role of these two populations of lymphocytes was characterized in this study. The existing literature suggests that B lymphocytes play an important role in chronic left ventricular remodeling following cardiac injury, although the specific B-cell mediated mechanisms have not been identified completely. Three different groups have studied the role of myocardial B lymphocytes following acute coronary ligation (MI). Both Yan et al (22) and Zouggari et al (23) reported that the number of myocardial CD19+ cells increased after MI. Zouggari showed that CD19+IgD+IgM-low B lymphocytes influx into the infarcted myocardium and contribute to adverse LV remodeling by recruiting Ly6C+ monocytes from the bone marrow through a CCL7-dependent mechanism (23). In contrast, a recent study found that CD19+ cells are recruited preferentially to fat associated lymphoid clusters in pericardial adipose tissue, with minimal detection of CD19+ cells in the myocardium after MI (24). Using a non-surgical model of cardiac injury, Cordero-Reyes showed that adverse cardiac remodeling was attenuated by antibody-dependent depletion of B cells in wild-type mice (25). Although the mechanisms of action of B-lymphocyte mediated myocardial damage have not been fully elucidated, there are several mechanisms that have been proposed, including dysregulation of B-cell subpopulations (B1 vs B2 vs B-regs), deposition of IgM or IgG antibodies, as well as B-cell mediated recruitment Ly6C+ monocytes (23). In this regard, it is interesting to note that Zhang et al showed that natural IgMs play a role in myocardial I/R injury, although they did not specifically study myocardial B lymphocytes (26).

The results of the presented herein both confirm and expand upon prior studies that have described myocardial B lymphocytes and suggested that B lymphocytes play an important role in modulating adverse cardiac remodeling following cardiac injury. For the first time it was shown that in naïve murine hearts the majority of B lymphocytes are CD19+ CD11b− CD21− CD23− CD11c− IgD+ IgMlow/−, whereas a minority of myocardial B lymphocytes is CD19+ CD11b+. In this latter group, a smaller fraction express CD5, which is characteristic of B1a lymphocytes, and a larger fraction is CD5−, which is characteristic of B1b lymphocytes(16). Although the phenotype of the CD19+ CD11b− cells that we describe overlaps the phenotypic description of the B cells that accumulated in the myocardium post-infarction in the report by Zouggari et al. (i.e, CD19+IgD+ IgMlow), it bears emphasis that the precise ontogeny of the CD19+ CD11b− CD21− CD23− CD11c− IgD+ IgMlow/− cells described herein is not known. To our knowledge, the phenotype of these cells does not match the profile of any previously described B cells subset (27). B cells can be broadly characterized into B1 and B2 lymphocytes, which are classically considered, respectively, innate and adaptive. Whereas B1a lymphocyte development occurs primarily during fetal and perinatal life, B1b and B2 lymphocyte production continues throughout adult life. The observation that these cells express relatively high levels of IgD+, which is characteristic of B2 cells, and low levels of IgM, which are characteristically expressed by B1 cells, suggests that these cells are not B1 cells (31). Of note, several authors have reported that a distinct population of mature CD19+ CD21−CD23− B cells accumulate in aging mice (28). However, these "age associated B cells" are CD11c+ and express the transcription factor T-bet, whereas we did not detect CD11c expression via FACS, nor gene expression of T-bet by RNAseq (data not shown). Our results further expand upon the existing literature on myocardial B cells also by showing that unique subsets of B lymphocytes increase in the heart following I/R injury, and that different subsets of myocardial B lymphocytes (CD19+ CD11 b+ and CD19+ CD11 b− lymphocytes) are activated differentially following cardiac injury, in a process that is modulated by Pirfenidone. Although, we did not observe a statistically significant increase in CD19+ lymphocytes in the heart after DT-mediated cardiac injury, the overall trends were similar to those observed with I/R injury. The quantitative differences in B cell response may be secondary to differences in the degree of tissue injury and/or differences in B lymphocyte kinetics in the two different injury models.

Our findings suggest that B cells are required for the cardioprotective effects of Pirfenidone after acute tissue injury and that B cell depletion does not mimic the cardioprotective effects of Pirfenidone following tissue injury in vivo. Although these results are seemingly incongruent at first blush, they suggest a more nuanced model supported by our transcriptional profiling studies in vivo, wherein Pirfenidone exerts its beneficial effects by modulating the immune response of B cells to tissue injury. Based on the results of our informatics analysis we hypothesized that activation of TLR signaling in response to the release of the cytosolic contents from necrotic cells (i.e. damage-associated molecular patterns, DAMPS) might activate B cells through a Pirfenidone sensitive process. We found that necrotic cell extracts were sufficient to upregulate the co-stimulatory molecule CD86 in B lymphocytes isolated from cultures of mixed inflammatory cells, whereas necrotic cell extracts were not sufficient to upregulate CD86 in purified B cell preparations. In contrast, LPS, a classic TLR4 agonist, induced upregulation of CD86 in CD19+ cells in PDICs as well as in purified B cell preparations. These findings are consistent with prior reports, showing that B lymphocytes response to TLR agonists is context-dependent (29) and suggest that B lymphocyte activation in response to necrotic cell extract is, at least in part, non-cell autonomous. Importantly, we observed that Pirfenidone significantly attenuated the number CD19+CD86+ lymphocytes in PDIC cultures stimulated with necrotic cell extracts or LPS. Consistent with our in vitro studies, we observed that there was a significant decrease in CD19+ CD86high lymphocytes in the hearts of DT-injured and I/R injured mice treated with Pirfenidone when compared to untreated controls. Our in vitro results with TIRAP−/− cells suggest that activation of B cells by necrotic cell extracts is TIRAP-dependent. However, LPS induced activation of B cells in vitro was attenuated but not abrogated in TIRAP−/− mice. This is consistent with prior observations that LPS signaling can activate multiple intracellular pathways in B cells (30).

In our work we found that Pirfenidone dependent immunomodulation of the cardiac inflammatory infiltrate improved cardiac function after acute injury. Surprisingly, treatment with Pirfenidone was not associated with a reduction in Troponin on day 4 after administration of diphtheria toxin (FIG. 1B) nor a reduction in infarct size after UR injury, as assessed by trichrome staining (FIG. 3G-FIG. 3H). This finding suggests that cardiac B lymphocytes might modulate cardiac remodeling post injury.

Although it has been long recognized that the innate immune system plays an important role in the adverse cardiac remodeling and myocardial dysfunction that ensues following acute myocardial injury, the quest to identify viable therapeutic targets has been elusory to date, because of the inherent duality of the innate immune response, which is required for initiating cardiac repair following tissue injury (32). Here we show a previously unappreciated complexity of the B lymphocyte component of the acute inflammatory response triggered by acute myocardial damage, and we show that B cells response to myocardial injury can be modulated through a small molecule based approach, as opposed to an antibody based approach. This raises the interesting question of whether Pirfenidone might be repurposed as an immunomodulatory agent in the setting of ischemia reperfusion injury following percutaneous cardiac angioplasty for ST-segment myocardial infarction. In contrast to monocytes/macrophages which are essential for cardiac repair, B lymphocytes function, at least in part, by modulating interactions between T cells, cardiac macrophages and dendritic cells. Accordingly, immunomodulatory strategies that are designed to target B cells may be less likely to lead to untoward effects, than are strategies that are aimed at cytokines and cell types that are critical for myocardial repair. Lastly, given the increasing recognition of the importance of B lymphocytes in the heart (21, 25, 33), these studies may also serve the heuristic purpose of focusing future studies on better understanding the origins, dynamics, temporal development and functional significance of the myocardial B lymphocytes in health, disease and aging.

Methods of Examples 1-8

Mouse Injury Models

To evaluate the effects of Pirfenidone on acute myocardial injury, we used two distinct in vivo experimental models of myocardial injury: a nonsurgical model of selective cardiac myocyte cell death (13) and a well-characterized surgical model of closed-chest ischemia reperfusion (I/R) injury. (34) (15) The mice for these experiments were bred and maintained at the Washington University School of Medicine and all experimental procedures were done in accordance with the animal use oversight committee.

DT-Injury Model. Mlc2v-Cre mice (C57BL/6J [Jackson Labs]) were crossed to Rosa26-DT mice (C57BL/6J) to generate lines of Rosa26-DT Mlc2v-Cre mice. Female mice, 9-40 weeks of age, were injected IP with 2.5 ng/g of diphtheria toxin (Sigma). Diphtheria toxin was solubilized according to manufacturer instructions and stored in aliquots at a concentration of 2000 ng/µL at −80° C. Aliquots stored at −80° C. were diluted to 20 ng/µL in PBS 1-10 days prior to use and stored at −20° C. Diphtheria toxin was diluted to a final concentration of 1 ng/µL in PBS immediately prior to injections. Littermate controls were used for each experiment. Mice were treated and studied as they became available and the results from all available experiments were compiled for analyses.

To assess the extent of myocyte injury following DT-induced injury, we measured troponin release and Evan's blue dye uptake. Troponin was measured day 4 after injection of DT at the time of terminal sacrifice. Blood was collected in BD microtainer tubes and the serum was diluted 1:4 in PBS (50 µl serum+150 µl PBS). Serum troponin was measured using a commercial chemiluminescent microparticle assay (Abbot Laboratories, Chicago, Il, USA). Evan's Blue dye uptake was assessed on day 4 after DT injection, as described (35, 36). Hearts were examined at the level of the papillary muscle using Image J software. Data are expressed as the percent area of the myocardium with red fluorescence.

Ischemia Reperfusion (I/R) Injury. Hearts from wild-type (WT) mice (C57BL/6J; purchased from Jackson Laboratory) were subjected to ischemia reperfusion (I/R) injury, using the closed-chest ischemia reperfusion model developed by Entman and colleagues (34), and modified as we have described previously (15). For the studies described herein we used 9-10 week old mice that were instrumented, then at 1 week post instrumentation were anesthetized with 1.5% isoflurane, and subjected to 90 minutes of closed-chest ischemia, followed by reperfusion for 2 weeks.

Pirfenidone Treatment

In order to administer Pirfenidone, mice were fed powdered chow mixed with Pirfenidone (eNovation Chemicals, Bridgewater, NJ, USA, Cat #D404655) at 0.5% in weight or powdered chow alone. This dosage has been commonly used in rodent models and has been suggested to result in plasma concentrations similar to those observed in humans treated with Pirfenidone (37). Unless specifically noted, mice were switched to a diet enriched with Pirfenidone 3 days prior to DT-induced injury or I/R-injury, and maintained on this diet throughout the duration of the experiments. In parallel studies, we fed mice normal chow prior to I/R injury and then administered Pirfenidone acutely at the time of cardiac injury. For these latter studies, mice were injected i.p. with diluent (200 µL phosphate-buffered solution [PBS]) or i.p. with Pirfenidone (200 µL of Pirfenidone [5 mg/mL] in PBS) after reperfusion and the morning after I/R injury (2 injections total). They were switched to Pirfenidone-enriched diet or control diet the evening of I/R injury and maintained on the same diet until completion of the experiment.

B Cell Depletion

For the B cell depletion studies, mice were injected with 100 µg of anti-CD20 antibody (Biolegend, Clone SA271G2, Catalog #152104) through the jugular vein. The injected antibody was diluted in PBS, pH 7.2, containing no preservative (endotoxin level<0.01 U/µg of protein) and filtered using a 0.2 µm filter. Immunodepletion was assessed at different time points, as described in the results section.

Gravimetric and Histological Analysis

Rosa26-DT Mlc2v-Cre and littermate control WT mice were euthanized 14 days after DT injection, and the hearts were removed and weighed to determine the heart-weight-to-tibia-length-ratio. WT mice were euthanized 14 days after I/R injury and the hearts were removed and weighed to determine the heart-weight-to-tibia-length-ratio. Hearts were processed, paraffin-embedded, and stained with hematoxylin/eosin and Masson's trichrome, as described (38). TUNEL staining was performed with the Millipore (Burlington, MA, USA) S7200 ApopTag Peroxidase In Situ Oligo Ligation Apoptosis Detection Kit according to the manufacturer's instruction.

Echocardiographic Studies

Image acquisition. Ultrasound examination of the cardiovascular system was performed using a Vevo 2100 Ultrasound System (VisualSonics Inc, Toronto, Ontario, Canada) equipped with a 30 MHz linear-array transducer, as previously described (15).

Imaging Protocol. Mice were imaged by echocardiography at the time of ischemia and 2 weeks after reperfusion to evaluate LV structure and function, as described (39). The echocardiographer was blinded to study group assignment. Animals with poor acoustic windows or small areas at risk (<0.45) at the time of ischemia were excluded from further analysis.

Cell Culture

Peritoneal derived inflammatory cells (PDICs) were harvested from the peritoneal cavity of thioglycolate-stimulated wild-type and TIRAP−/− deficient mice. PDIC cultures contain an admixture of inflammatory cells, including CD19+ B cells (40). TIRAP deficient mice were a gift from Dr. Ruslan Medzhitov (Yale University, New Haven, CT). PDICs were harvested on day 4 after i.p. injection of 1 ml of thioglycolate medium (Millipore, Billerica, MA, USA). Mice were euthanized, and the peritoneal cavity was washed 3-4 times with 3 mLs of Dulbecco's modified medium containing 10% fetal calf serum. A 3 mL syringe with an 18-gauge needle was used to inject the peritoneal cavity and retrieve the medium containing PDICs. Harvested cells were centrifuged at 250 g for 5 minutes, re-suspended in 5 mL of media and then filtered through a 40 µm strainer. Cells were plated at ~1.5 million cells/mL in 12 or 24 well plates. Primary splenic derived B lymphocytes were isolated with the MagniSort Mouse B cell Enrichment Kit (Invitrogen, Carlsbad, CA, USA) according to manufacturer's instruction and plated in 96 well plates at 1 million cells/ml. The purity of isolated B cells was checked by flow cytometry and was >85% in all reported experiments. Both PDICs and primary B lymphocytes were cultured in DMEM with 10% FCS, 1 mM sodium pyruvate, penicillin/streptomycin (GIBCO, 1×), 2 mM L-Glutamine, 10 mM Hepes and 55 µM 2-Mercaptoethanol.

We used LPS-EB ultrapure lipopolysaccharide (InvivoGen, San Diego, CA, USA) or necrotic cell extracts (NCEs) to stimulate the cell cultures. For stimulation with LPS, LPS was added at 100 ng/mL at the time of plating. NCEs were prepared from H9c2 cells, in a similar manner to the protocol described for mouse heart and mouse liver extracts (18). For stimulation, NCEs were added at a final concentration of 10 µg/mL at the time the cells were plated. LPS and NCE stimulation were performed in the presence and absence of Pirfenidone for 24 hours. Pirfenidone was solubilized (10 mg/mL) in Dulbecco's Modified Eagles medium (DMEM) by two rounds of gentle heating in a water bath at 65Co for 5 minutes, followed by vortexing for 20 seconds. The Pirfenidone solution was stored at 4Co and used within 24 hours from preparation. Pirfenidone was added at a final concentration of 150 ng/m L. For flow cytometric analysis (FACS), both adherent and non-adherent cultured cells were collected. Non-adherent cells were collected by pipetting up and down the culture media prior to media collection and a single rapid wash with Cell Stripper (Corning, NY, USA) and then gently centrifuged at 250×g for 3 minutes. To collect the adherent fraction, cells were incubated for 30 minutes at 37Co with Cell Stripper (Corning, NY, USA) and then detached by gentle pipetting followed by mechanical detachment with a cell lifter. The adherent cells were mixed with the non-adherent cells, spun down at 250×g for 3 minutes and resuspended in 300 µL of FACS buffer for further processing.

Flow Cytometry

For flow cytometry experiments, mice were euthanized in a CO2 chamber and the hearts were perfused with cold PBS, carefully dissected from extracardiac tissue under a stereo microscope, finely minced, suspended in 3 ml of DMEM, and then digested with 120 U of DNAse (Sigma), 180 U of hyaluronidase (Sigma) and 1350 U of Collagenase (Sigma) for 60 minutes at 37Co. The digested material was filtered through 40 µm filters and pelleted by centrifugation (250×g for 3 minutes at 4° C.) in HBSS supplemented with 2% FCS+0.2% bovine serum albumin (BSA). Red blood cells were lysed in ACK lysis buffer (Invitrogen) for 15' on ice and the remaining cells were resuspended in 300 µL of FACS buffer (PBS with 2% FCS and 2 mM EDTA). Cultured cells were collected for FACS analysis as described above and resuspended in 300 µL of FACS buffer. Samples were labeled with the fluorescently conjugated antibodies outlined in the table below. Cells were stained for 45 minutes on ice, and washed in FACS buffer prior to analysis. All antibodies from Biolegend were used at 0.2 µL per 300 µL sample, while antibodies from BD biosciences were used at 0.4 µL per 300 µL sample. FACS was performed on Beckton Dickinson analyzers (LSRII, Canto, X20 or Fortessa). Compensation controls were generated using UltraComp ebeads (Invitrogen, Carlsbad, CA, USA) and verified on single color control samples obtained staining primary splenocytes. For flow cytometry experiments that involved the DT injury model, we collected serum at the time of terminal sacrifice for quantification of troponin. In pilot studies we observed that mice with a serum troponin<1 ng/ml did not have appreciable tissue injury; therefore, mice with serum troponin<1 were excluded from further analysis. Cell sorting was performed using a FACSAria sorting instrument (Beckton Dickinson) at the Washington University Department of Pathology Flow Cytometry and Sorting Core. A list of all antibodies used including brand, clone number and fluorophores used in provided in Table 1

Transcriptional Profiling

We performed transcriptional profiling of cardiac lymphocytes that were isolated from naïve and DTR injured hearts in the presence and absence of Pirfenidone. We FACS sorted CD19+CD11b+ and CD19+CD11b− cardiac lymphocytes from naïve, DT-injured hearts, and DT+Pirfenidone hearts directly into lysis buffer for RNA isolation. A total of 600 to 12,000 cells were sorted from each heart. RNA was extracted using the Zymo Research QuickRNA MicroPrep (Zymo Research, Irvine, CA, USA), according to the manufacturer's instructions. RNA was eluted in 11 µl and the whole volume was submitted for whole transcriptome analysis. Myocardial B lymphocytes were sorted from 8 naïve animals, 6 DT mice and 3 DT+PFD treated mice. Total RNA obtained from sorted B cell populations was selected for polyadenylated RNA and converted to RNA-sequencing libraries using the SMARTer v2 kit from Clontech. Single-end, 50 bp reads were obtained on an Illumina HiSeq 3000 and aligned to the Illumina iGenomes GRCm38_Ensembl release of the mouse transcriptome using Tophat2.1(41), yielding an average of $1.8 \times 10^7$ aligned reads per sample. Gene-level quantitation was performed using HTSeq 2(42). mRNAs were included in downstream analyses if present in all biological replicates in any of the 6 experimental groups (CD19+CD11b+ and CD19+CD11b− from WT, DT and DT+PFD) at an abundance of at least 1 read per million. A total of 12,097 mRNAs were obtained from this filtering procedure. In order to compare gene expression respectively in CD19+CD11b+ cells and CD19+CD11b− cells across untreated, DT-injured and DT-injured+Pirfenidone conditions, gene expression data were corrected for variability among experimental batches and a principal components analysis across all 12,097 mRNAs for the 17 sequenced samples was performed. This highlighted 5 samples (1 CD19+CD11b+/DT heart, 2 CD19+CD11b−/naïve hearts and 1 CD19+CD11b−/DT heart) that were strong outliers being outside the 95% confidence interval (2 standard deviations) for their group and that were removed from further analysis. The data is available on the NCBI GEO repository, accession number GSE112984. The limma-voom procedure was used to identify mRNAs with differential expression between experimental conditions(43). KEGG pathway analysis was performed on mRNAs with >2 fold change in expression level between specific experimental groups using the appropriate functional annotation module within the 2017 release of the NIH online resource DAVID (44) and accepting an FDR≤0.05 (Benjamini-Hochberg method) to identify pathways enriched between the assigned conditions. KEGG pathways within the following 3 categories were analyzed: signal transduction (3.2), signaling molecules and interactions (3.3), and immune system (5.1).

Statistics

Data are expressed as mean±standard deviation. Two tailed Student's t test was used for pairwise comparisons between two groups, one-way ANOVA with Tukey's correction for multiple post hoc comparisons was used to compare multiple experimental groups, while two-way ANOVA with Tukey's correction for multiple post hoc comparisons was used to compare across multiple experimental groups with multiple conditions in each group. The Gehan-Breslow-Wilcoxon method was used to compare Kaplan-Meier curves. A p value<0.05 was considered statistically significant. The specific statistical test used in each experiment is indicated in the figure captions. All calculations were made using GraphPad Prism Version 7.04.

Example 9: In Vitro Immunomodulatory Effect of Tested PEG Compounds

Peritoneal derived inflammatory cells were collected on day for post intraperitoneal injection of Thyoglicollate. Cells were cultured for 24 h in baseline condition (control), in the presence of LPS 100 ng/ml (LPS) or in the presence of LPS 100 ng/ml and various concentrations of different forms of Pegylated Pirfenidone (named C2 and C3 in FIG. 11A and C4 to C6 in FIG. 11B)). After the 24 h in culture cells were collected and analyzed via flow cytometry to assess the expression of CD86 on CD19+ cells (B lymphocytes). The graphs in FIG. 11A and FIG. 11B show that both Pirfenidone and the tested forms of Pegylated Pirfenidone reduced the expression of CD86 on CD19+ cells. FIG. 11C reports the molecular weights of the tested forms of PEGylated Pirfenidone and the molecular weight (MW) ration between the tested compound and Pirfenidone). FIG. 11D shows the molecular structures of the tested PEGylated Pirfenidone variants (C2 to C6) together with an assessment of their relative potency to Pirfenidone (calculated converting the amount of drugs used from concentrations in weight to molarity) and an assessment of in vitro toxicity (assessed by visual inspection of the cultured cells and DAPI staining at the time of flow cytometric analysis). Importantly, the table shows that the tested variants of PEG-Pirfenidone are not equivalent and C6 (Pegydone 6) is superior to the other tested variants.

Example 10: Pk and Bioavailability of Pegydone 6 Compared to Pirfenidone

Blood was collected at pre-specified time points and the concertation of the administered drug was measured by mass spectrometry (LC-MS-MS). Each time point was collected in triplicate. FIG. 12A reports the data collected after IV administration of Pirfenidone, FIG. 12B reports the data collected after administration of Pegydone 6. FIG. 12C reports the half-life of the two drugs as calculated from the graphs reported in FIG. 12A and FIG. 12B. FIG. 12C reports the calculated half-life and bioavailability of Pegydone 6 and Pirfenidone.

Example 11: Measurement of Pirfenidone Effects on Circulating B Cells In Vivo

FIG. 13A shows after 3 weeks of Parabiosis conjoined mice show 50% chimerism of circulating CD19+ B lymphocytes. FIG. 13B Analysis of chimerism of myocardial B lymphocytes. Conjoined animals show 50% of chimerism in both CD19+CD11 b+ and CD19+CD11 b− myocardial B lymphocytes. FIG. 13C ratio of chimerism between myocardial CD19+ cells and circulating CD19+ cells. The ratio of B cell chimerism between blood and myocardium is about 1. This confirm that myocardial B lymphocytes recirculate rapidly and are at equilibrium with circulating B lymphocytes and demonstrates that the effects of Pirfenidone and/or PEGpirfenidoen on myocardial B cells could be assessed on peripheral blood B lymphocytes Example 12: Pirfenidone in the Treatment of Age Associated Myocardial Changes in Vivo Myocardial B cells change with aging and that therefore Pirfenidone and/or PEG-Pirfenidone could be used to modulate age associated changes in myocardial B cells. Mice of the indicated different ages were sacrificed and the hearts were analyzed via flow cytometry. Each time point was measured in triplicate. FIG. 14A shows that with aging the prevalence of CD19+ cells increases. FIG. 14B shows that the prevalence of CD19+CD11 b+ cells increases as well. FIG. 14C shows that with aging the prevalence of CD19+ CD11b− cells decreases.

Example 13: Use of Pirfenidone to Modulate Myocardial B Cells in Humans

The data shows that the human heart harbors populations of B cells similar to those observed in the murine heart and therefore argues that Pirfenidone or PEG-Pirfenidone are likely to have in humans cardioprotective effects similar to those observed in mice.

Example 14: Pegylated Pirfenidone Derivatives

Various pegylated pirfenidone derivatives were designed and synthesized by incorporating polyethylene glycol (PEG) polymer into pirfenidone. The potential benefits of the pegylated small molecules are to: 1) modify biodistribution, 2) decrease transport out of cells, 3) improve oral availability, 4) modify metabolism, and 5) modify drug half-life and other pharmacokinetic properties.

Figure 16A:
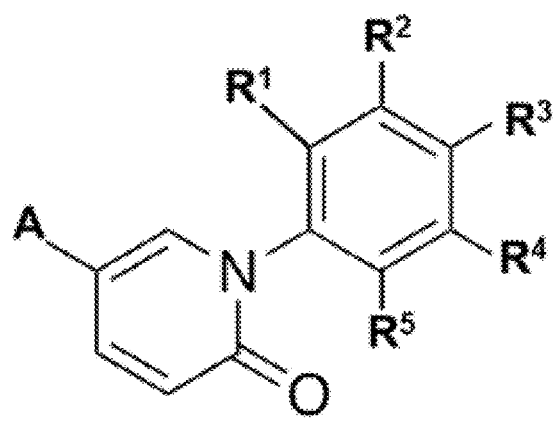
Figure 16B:
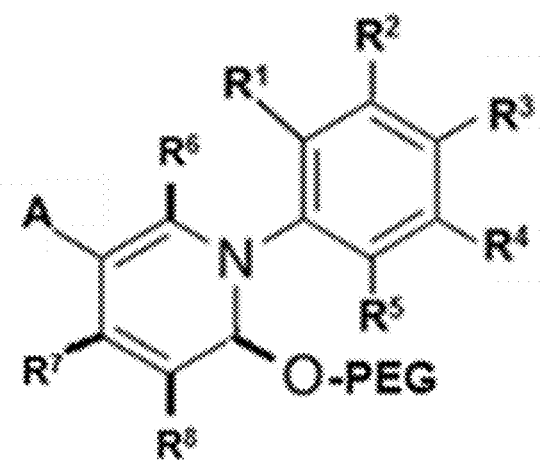
Figure 16C:
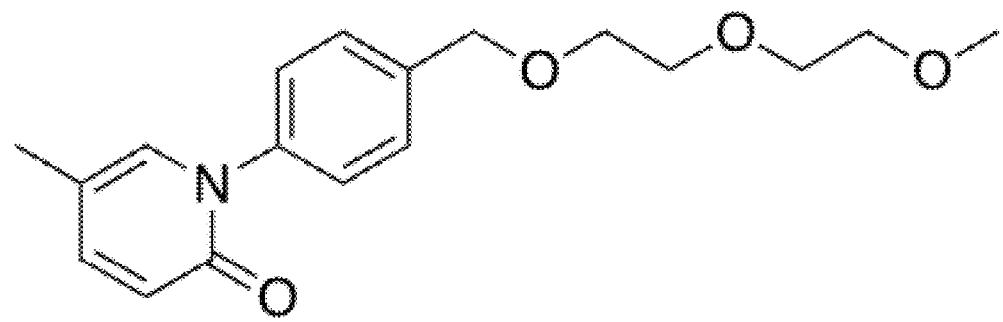
Figure 16D:
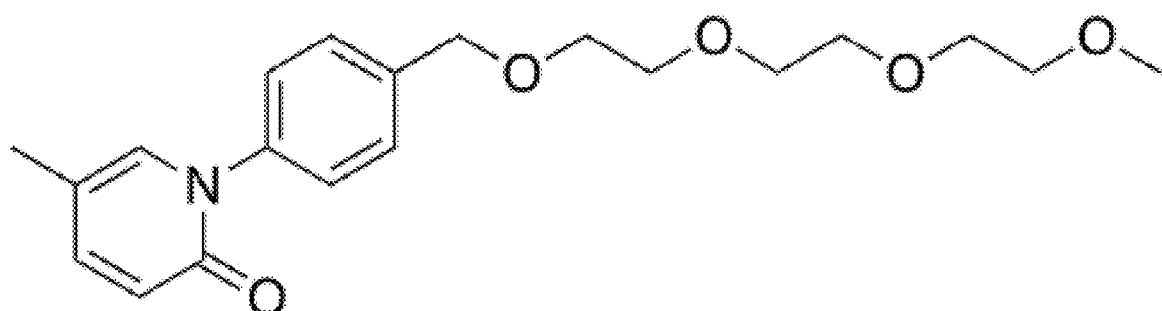
Figure 16E:
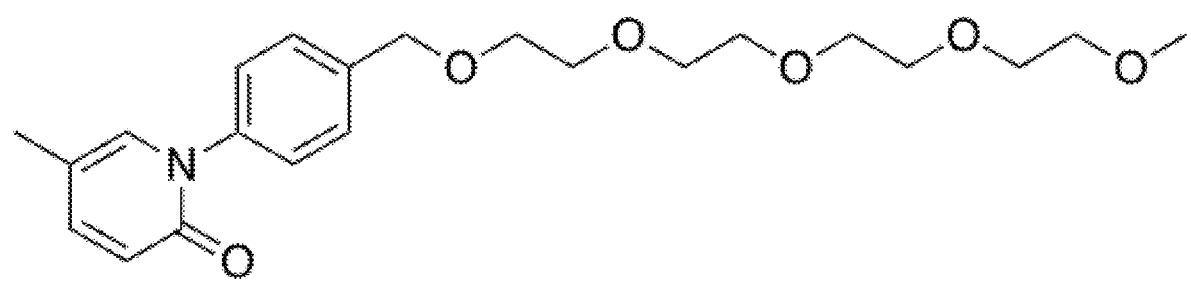
Figure 16F:
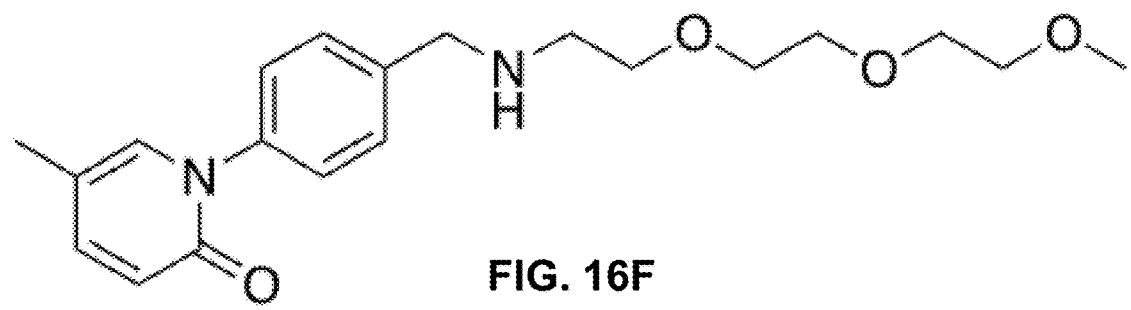
Figure 16G:
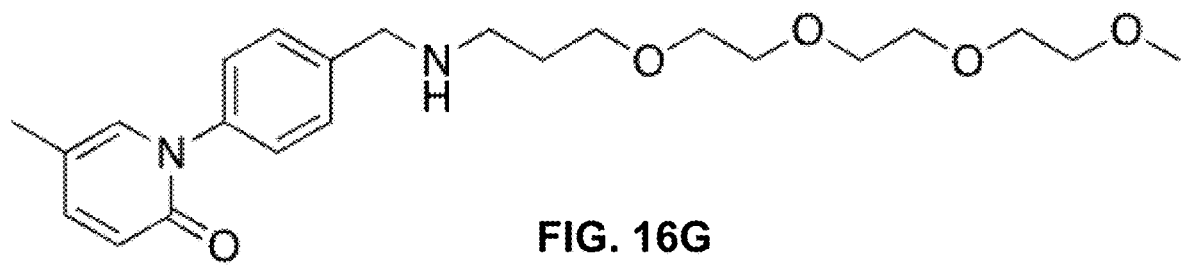
Figure 16H:
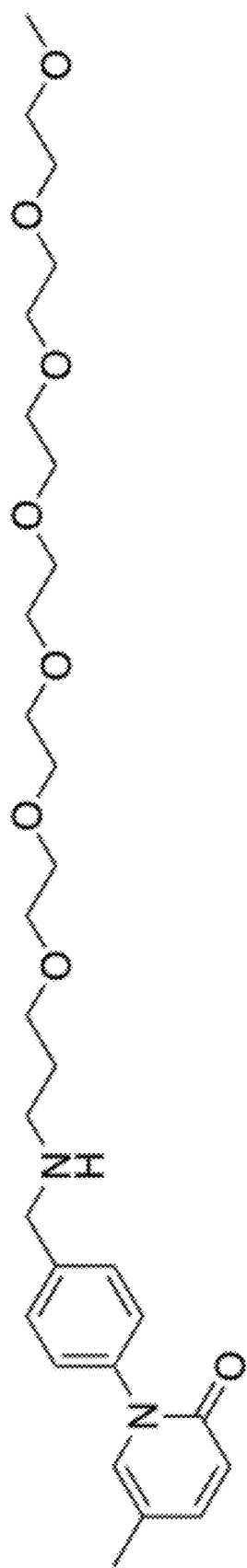
Figure 16I:
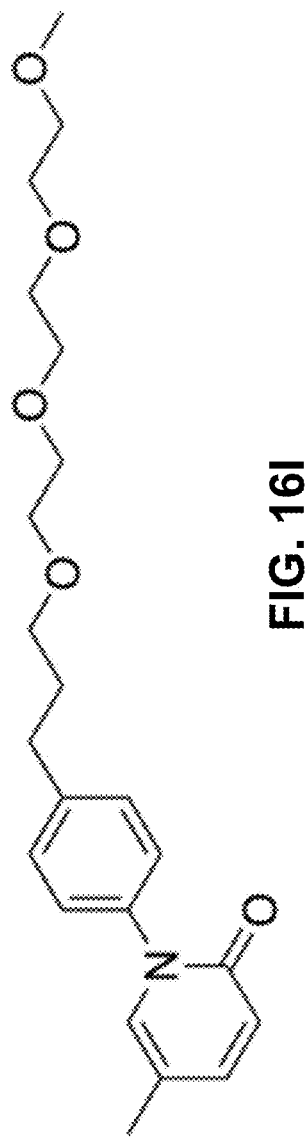
Figure 16J:
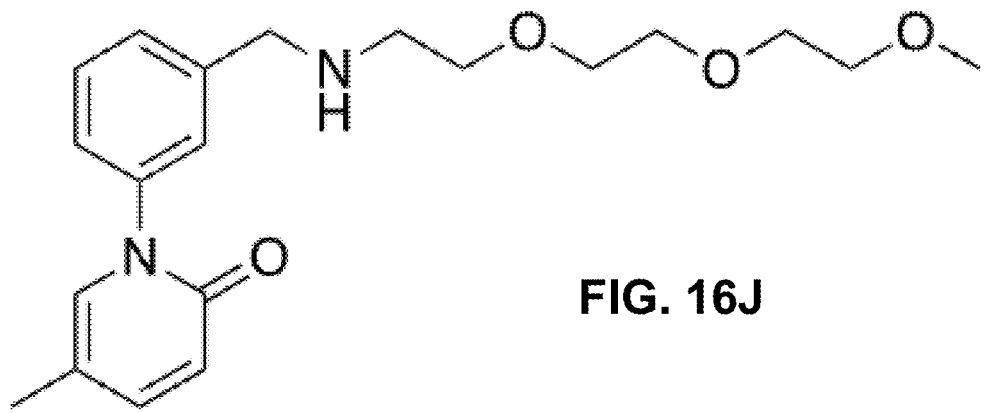
Figure 16K:
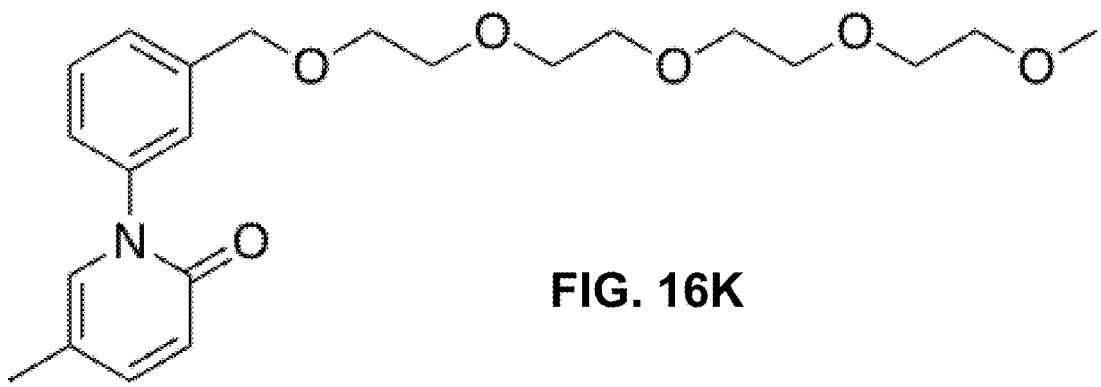
Figure 16L:
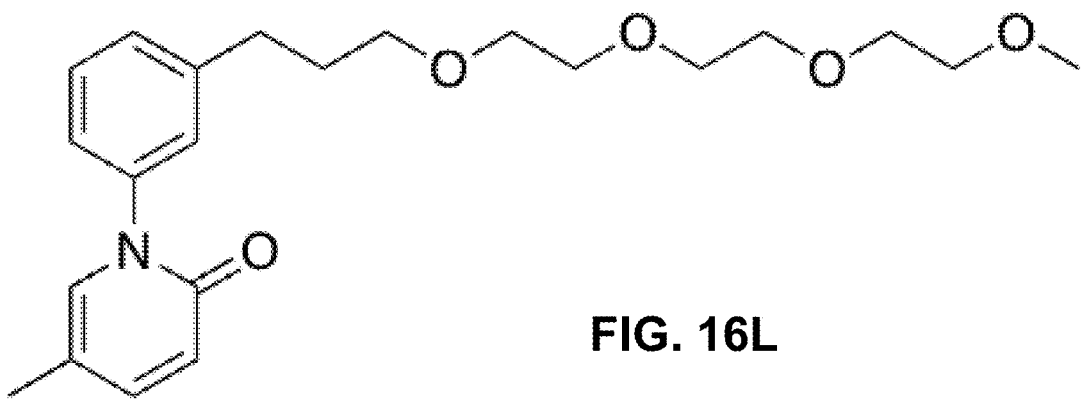
Figure 16M:
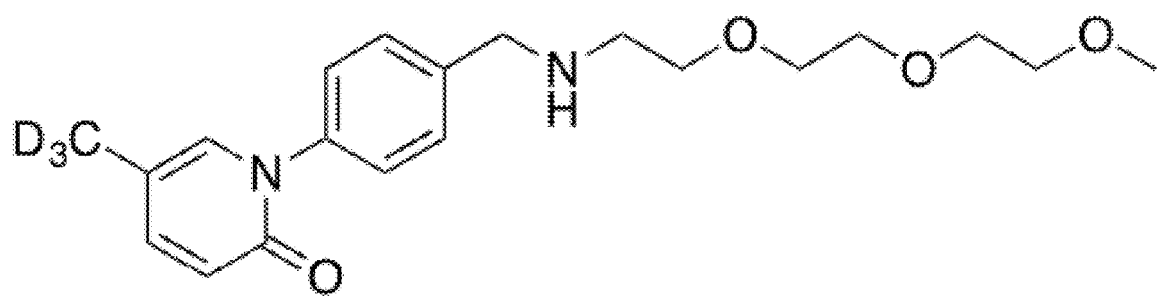
Figure 16N:
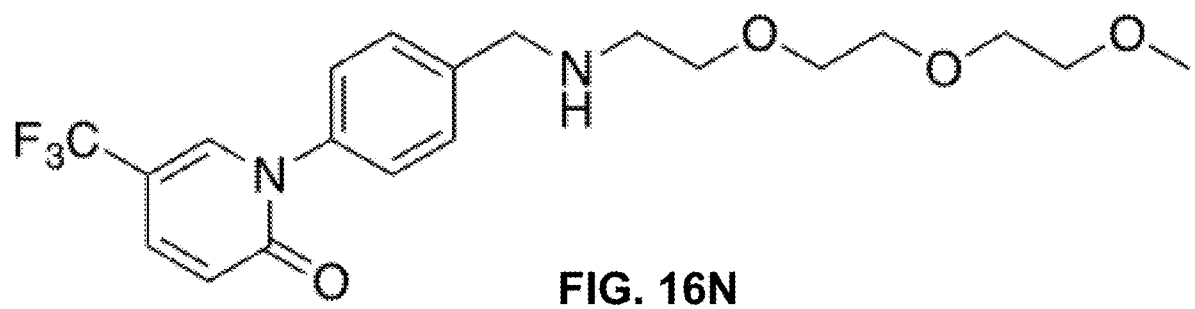
Figure 16O:
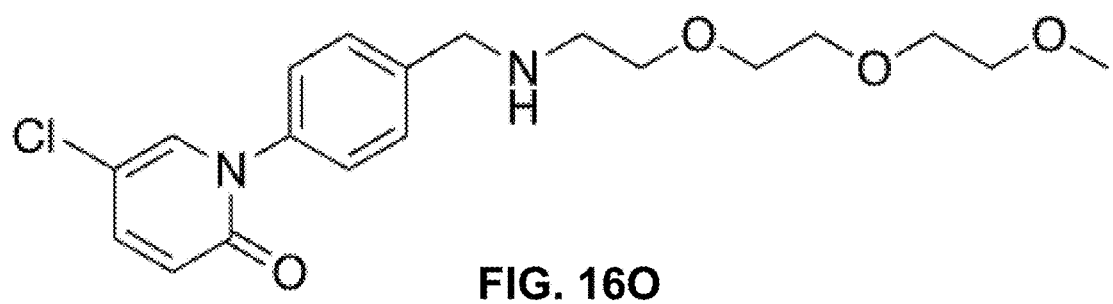
Figure 16P:
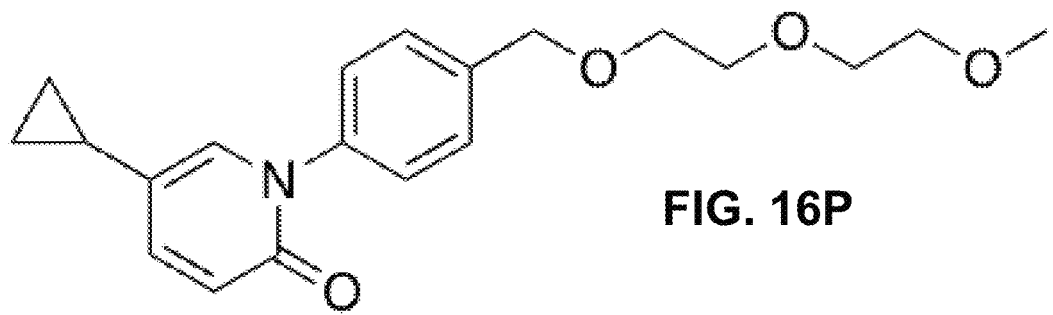
Figure 16Q:
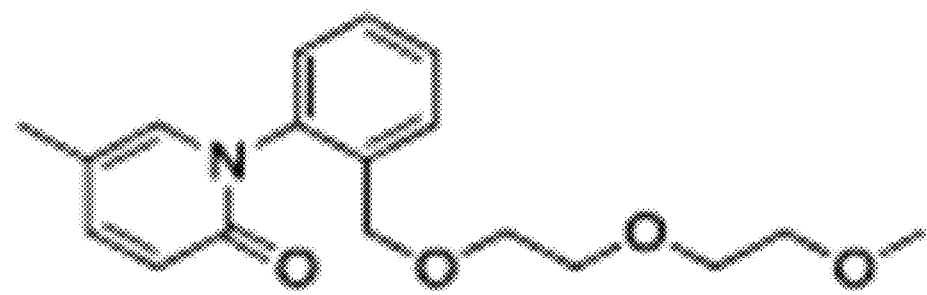
Figure 16R:
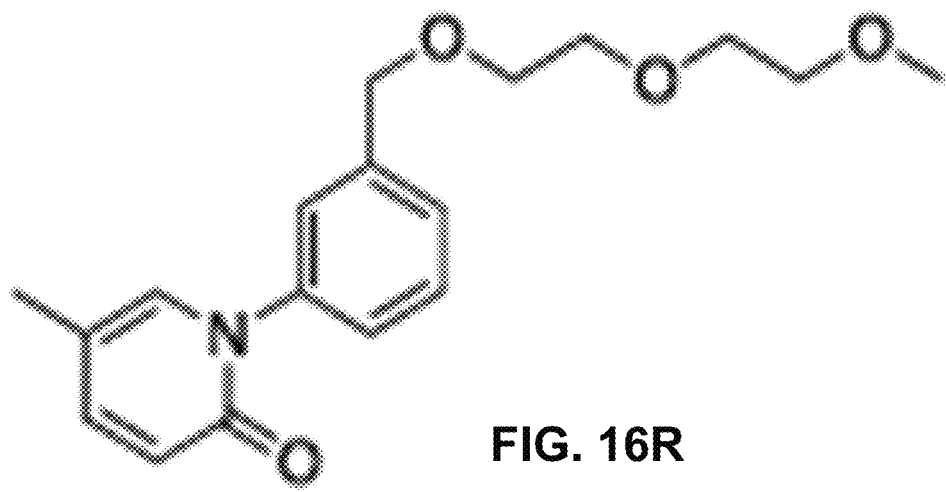
Figure 16S:
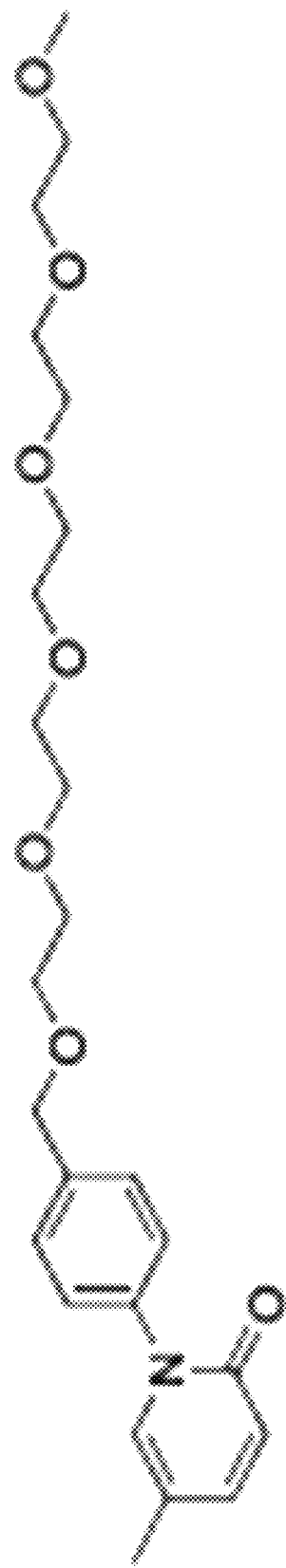
Figure 16T:
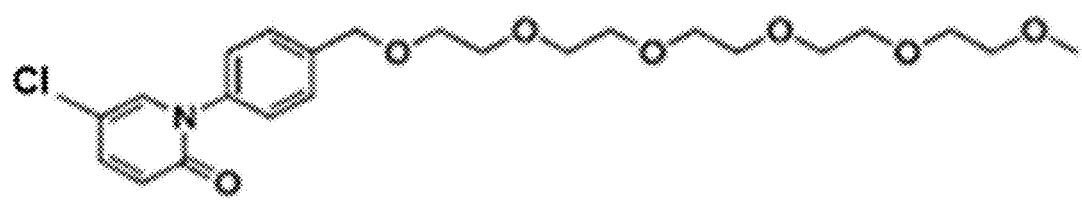
Figure 16U:
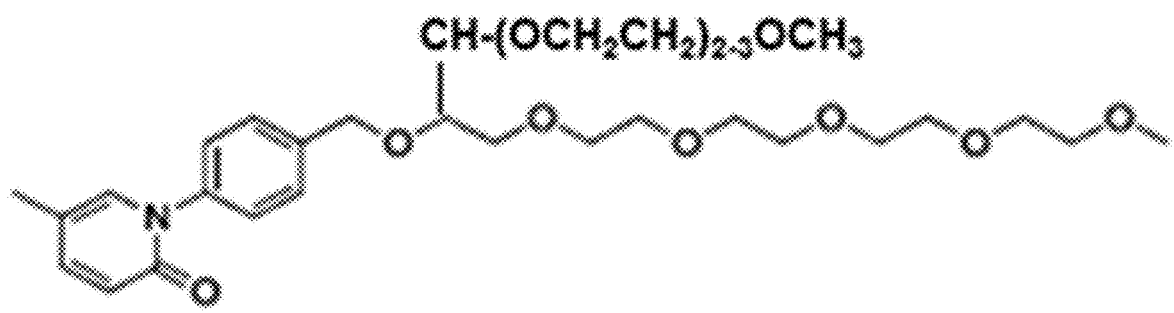
Figure 16V:
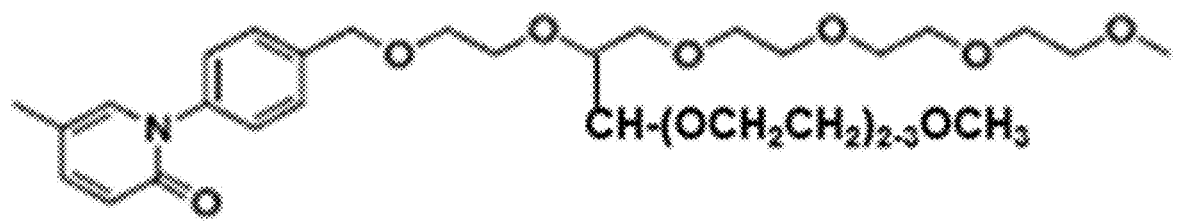
Figure 16W:
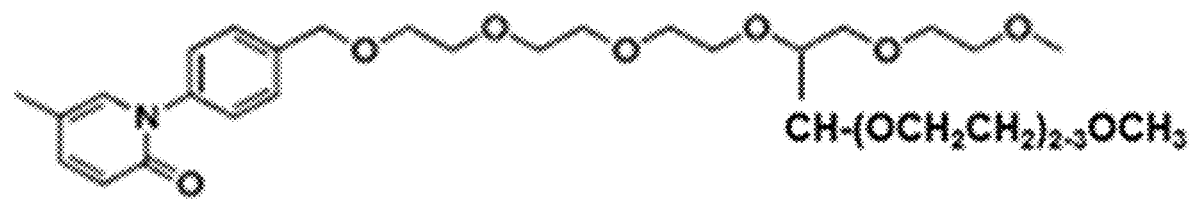

The pegylated pirfenidone derivatives were synthesized by various substitutions into the generic structure as shown in FIG. 16A and FIG. 16B. The chemical structures of some of the pegylated derivatives of pirfenidone that were designed and synthesized are shown in FIG. 16B-16W.

TABLE 1

KEGG analysis of genes with differential expression ≥2 folds or ≤2 folds in $CD19^+$ $Cd11b^+$ cells sorted from DTR injured hearts vs naïve hearts (Pathway followed by differentially expressed genes within that pathway)

Hematopoietic cell lineage

CD14 antigen
CD19 antigen
CD2 antigen
CD22 antigen; hypothetical protein LOC100047973
CD34 antigen
CD36 antigen
CD37 antigen
CD55 antigen
CD9 antigen
Fc receptor, IgE, low affinity II, alpha polypeptide
complement receptor 2
interleukin 1 beta
interleukin 1 receptor, type II
interleukin 5 receptor, alpha
membrane-spanning 4-domains, subfamily A, member 1
tumor necrosis factor
Cytokine-cytokine receptor interaction CD27 antigen
CD40 antigen
Fas (TNF receptor superfamily member 6)
chemochine (C-X-C motif) receptor 5
chemokine (C-C motif) ligand 4
chemokine (C-C motif) ligand 6
chemokine (C-C motif) receptor 1
chemokine (C-C motif) receptor 5
chemokine (C-C motif) receptor 6
chemokine (C-C motif) receptor 7

TABLE 1-continued

KEGG analysis of genes with differential expression ≥2 folds or ≤2 folds in CD19⁺ Cd11b⁺ cells sorted from DTR injured hearts vs naïve hearts (Pathway followed by differentially expressed genes within that pathway)

chemokine (C-X-C motif) ligand 2
colony stimulating factor 2 receptor, beta, low-affinity (granulocyte-macrophage)
interleukin 1 beta
interleukin 1 receptor, type II
interleukin 21 receptor
interleukin 5 receptor, alpha
interleukin 6 signal transducer
predicted gene 614; interleukin 2 receptor, gamma chain
tumor necrosis factor (ligand) superfamily, member 9
tumor necrosis factor receptor superfamily, member 10b
tumor necrosis factor receptor superfamily, member 12a
tumor necrosis factor receptor superfamily, member 13c
tumor necrosis factor
B cell receptor signaling pathway CD19 antigen
CD22 antigen; hypothetical protein LOC100047973
CD72 antigen
CD79A antigen (immunoglobulin-associated alpha)
CD79B antigen
RAS, guanyl releasing protein 3
caspase recruitment domain family, member 11
complement receptor 2
protein kinase C, beta
protein tyrosine phosphatase, non-receptor type 6
vav 2 oncogene
Cell adhesion molecules (CAMs)

CD2 antigen
CD22 antigen; hypothetical protein LOC100047973
CD34 antigen
CD40 antigen
histocompatibility 2, O region alpha locus
histocompatibility 2, O region beta locus
histocompatibility 2, Q region locus 1
histocompatibility 2, class II, locus Mb2
integrin alpha L
integrin beta 7
intercellular adhesion molecule 1
protein tyrosine phosphatase, receptor type, C
selectin, lymphocyte
similar to histocompatibility 2, T region locus 24
Antigen processing and presentation cathepsin B
cathepsin L
heat shock protein 1B; heat shock protein 1A; heat shock protein 1-like
heat shock protein 90 alpha (cytosolic), class B member 1
histocompatibility 2, O region alpha locus
histocompatibility 2, O region beta locus
histocompatibility 2, Q region locus 1
histocompatibility 2, class II, locus Mb2
legumain
similar to histocompatibility 2, T region locus 24; histocompatibility 2, T region locus 24
MAPK signaling pathway CD14 antigen
Fas (TNF receptor superfamily member 6)
RAS guanyl releasing protein 1
RAS, guanyl releasing protein 2
RAS, guanyl releasing protein 3
arrestin, beta 2
calcium channel, voltage-dependent, R type, alpha 1E subunit
calcium channel, voltage-dependent, alpha 2/delta subunit 4
dual specificity phosphatase 6
dual specificity phosphatase 7; similar to dual specificity phosphatase 7
growth arrest and DNA-damage-inducible 45 gamma
heat shock protein 1B; heat shock protein 1A; heat shock protein 1-like
interleukin 1 beta TABLE 1-continued KEGG analysis of genes with differential expression ≥2 folds or ≤2 folds in CD19⁺ Cd11b⁺ cells sorted from DTR injured hearts vs naïve hearts (Pathway followed by differentially expressed genes within that pathway)

interleukin 1 receptor, type II
mitogen-activated protein kinase kinase 3
mitogen-activated protein kinase kinase kinase kinase 2
protein kinase C, beta
ribosomal protein S6 kinase polypeptide 3
tumor necrosis factor Table 2 KEGG analysis of genes with differential expression ≥2 folds or ≤2 folds in CD19⁺ Cd11b⁻ cells sorted from DTR injured hearts vs naïve hearts. (Pathway followed by differentially expressed genes within that pathway)

Cytokine-cytokine receptor interaction

CD40 antigen(Cd40)
chemokine (C-C motif) ligand 4(Ccl4)
chemokine (C-C motif) receptor 1(Ccr1)
chemokine (C-C motif) receptor 5(Ccr5)
chemokine (C-X-C motif) receptor 2(Cxcr2)
colony stimulating factor 2 receptor, beta, low-affinity (granulocyte-macrophage)(Csf2rb)
colony stimulating factor 3 receptor (granulocyte)(Csf3r)
interleukin 1 beta(Il1b)
interleukin 1 receptor, type II(Il1r2)
leukemia inhibitory factor receptor(Lifr)
tumor necrosis factor receptor superfamily, member 13b(Tnfrsf13b)
Hematopoietic cell lineage CD14 antigen(Cd14)
CD2 antigen(Cd2)
CD55 molecule, decay accelerating factor for complement(Cd55)
Fc receptor, IgE, low affinity II, alpha polypeptide(Fcer2a)
colony stimulating factor 3 receptor (granulocyte)(Csf3r)
complement receptor 2(Cr2)
interleukin 1 beta(Il1b)
interleukin 1 receptor, type II(Il1r2)
tumor necrosis factor(Tnf)
Toll-like receptor signaling pathway CD14 antigen(Cd14)
CD40 antigen(Cd40)
chemokine (C-C motif) ligand 4(Ccl4)
interleukin 1 beta(Il1b)
mitogen-activated protein kinase kinase 1(Map2k1)
secreted phosphoprotein 1(Spp1)
signal transducer and activator of transcription 1 (Stat1)
tumor necrosis factor(Tnf)
Chemokine signaling pathway chemokine (C-C motif) ligand 4(Ccl4)
chemokine (C-C motif) ligand 6(Ccl6)
chemokine (C-C motif) receptor 1(Ccr1)
chemokine (C-C motif) receptor 5(Ccr5)
chemokine (C-X-C motif) ligand 2(Cxcl2)
chemokine (C-X-C motif) receptor 2(Cxcr2)
mitogen-activated protein kinase kinase 1(Map2k1)
phospholipase C, beta 2(Plcb2)
signal transducer and activator of transcription 1 (Stat1)
son of sevenless homolog 2 (Drosophila)(Sos2)
TNF signaling pathway B cell leukemia/lymphoma 3(Bcl3)
CCAAT/enhancer binding protein (C/EBP), beta(Cebpb)
activating transcription factor 6 beta(Atf6b)
chemokine (C-X-C motif) ligand 2(Cxcl2)
interferon gamma inducible protein 47(Ifi47)
interleukin 1 beta(Il1b)
mitogen-activated protein kinase kinase 1(Map2k1)
mitogen-activated protein kinase kinase kinase 5(Map3k5)
tumor necrosis factor(Tnf)

Example 15: PEG-Pirfenidone has an Extended Half-Life and Improved Bioavailability Compared with Pirfenidone Pirfenidone and Pegyonde-6 were administered at equimolar concentrations to rats IV or per os (PO) and serum concentrations measured at different time points to measure pharmacokinetic parameters. The drugs were solubilized in 5% Alcohol+20% PEG 300 in saline. The data reported below shows that PEG-Pirfenidone has longer half-life than Pirfenidone after both IV and PO administration and that PEG-Pirfenidone has better bioavailability than Pirfenidone.

TABLE 3

Plasma concentrations (ng/ml) of Pirfenidone after IV (40 mg/kg) administration to SD Rat

| | Rat # | | | | |
|---|---|---|---|---|---|
| Time (h) | 1 | 2 | 3 | Mean | SD |
| 0 | BLOQ | BLOQ | BLOQ | NA | NA |
| 0.083 | 32900 | 34700 | 33600 | 33733 | 907 |
| 0.25 | 21400 | 29300 | 25600 | 25433 | 3953 |
| 0.5 | 15800 | 19800 | 16100 | 17233 | 2228 |
| 1 | 6130 | 9860 | 4840 | 6943 | 2607 |
| 2 | 394 | 712 | 225 | 444 | 247.3 |
| 4 | 4.27 | 6.12 | 3.57 | 4.7 | 1.3 |
| 8 | 1.22 | BLOQ | BLOQ | 1.22 | NA |
| 24 | BLOQ | BLOQ | BLOQ | NA | NA |

TABLE 4

Plasma concentrations (ng/ml) of Pirfenidone after PO 40 mg/kg) administration to SD Rat

| | Rat# | | | | |
|---|---|---|---|---|---|
| Time (h) | 7 | 8 | 9 | Mean | SD |
| 0 | BLOQ | BLOQ | BLOQ | NA | NA |
| 0.25 | 9130 | 8330 | 9540 | 9000 | 615 |
| 0.5 | 8450 | 6700 | 8820 | 7990 | 1132 |
| 1 | 5110 | 3540 | 3570 | 4073 | 898 |
| 2 | 1190 | 2000 | 2140 | 1777 | 513 |
| 4 | 7.72 | 830 | 126 | 321 | 445 |
| 8 | BLOQ | 23.6 | 107 | 65.3 | NA |
| 24 | BLOQ | BLOQ | BLOQ | NA | NA |

BLOQ: Below lower limit of quantification (1 ng/mL)

TABLE 6

Plasma concentrations (ng/ml) of PEG-Pirfenidone after IV (96 mg/kg) administration to SD Rat

| | Rat # | | | | |
|---|---|---|---|---|---|
| Time (h) | 4 | 5 | 6 | Mean | SD |
| 0 | BLOQ | BLOQ | BLOQ | NA | NA |
| 0.083 | 44227 | 56484 | 96487 | 65733 | 27330 |
| 0.25 | 27605 | 35059 | 61343 | 41336 | 17723 |
| 0.5 | 13073 | 18584 | 19790 | 17149 | 3581 |
| 1 | 5974 | 6543 | 5755 | 6090 | 407 |
| 2 | 1786 | 2091 | 721 | 1533 | 720 |
| 4 | 216 | 156 | 178 | 183 | 30.3 |
| 8 | 12.9 | 11.5 | 36.3 | 20.3 | 13.9 |
| 24 | BLOQ | 2.97 | BLOQ | 2.97 | NA |

BLOQ: Below lower limit of quantification (1 ng/mL)

TABLE 7

Plasma concentrations (ng/ml) of PEG- Pirfenidone after PO 96 mg/kg) administration to SD Rat

| | Rat# | | | | |
|---|---|---|---|---|---|
| Time (h) | 10 | 11 | 12 | Mean | SD |
| 0 | BLOQ | BLOQ | BLOQ | NA | NA |
| 0.25 | 8298 | 40817 | 21638 | 23584 | 16346 |
| 0.5 | 3977 | 35217 | 18477 | 19224 | 15633 |
| 1 | 1157 | 7033 | 3053 | 3748 | 3083 |
| 2 | 219 | 885 | 217 | 440 | 385 |
| 4 | 28.4 | 129 | 48.8 | 69 | 53 |
| 8 | 3.09 | 33.4 | 6.16 | 14 | 17 |
| 24 | BLOQ | BLOQ | BLOQ | NA | NA |

BLOQ: Below lower limit of quantification (1 ng/mL)

TABLE 5

Plasma pharmacokinetic parameters Pirfenidone after IV (40 mg/kg) or PO (40 mg/kg) administration to SD Rat

| Dosing Route | Rat | $T_{1/2}$_range* (h) | $T_{1/2}$ (h) | $T_{max}$ (h) | $C_{max}$ (ng/mL) | $AUC_{0-t}$ (ng·h/mL) | $AUC_{0-\infty}$ (ng·h/mL) | $AUMC_{0-t}$ (h*h*n g/mL) | $AUMC_{0-\infty}$ (h*h*n g/mL) | $MRT_{INF}$ (h) | CL(/F) (mL/h/kg) | Vss (/F) (mL/kg) | F % |
|---|---|---|---|---|---|---|---|---|---|---|---|---|---|
| IV | 1 | 0.083-8 | 0.500 | 0.083 | 32900 | 21394 | 21395 | 10270 | 10277.2 | 0.480 | 1870 | 898 | |
| | 2 | 1-4 | 0.283 | 0.083 | 34700 | 27907 | 27910 | 15155 | 15166.3 | 0.543 | 1433 | 779 | |
| | 3 | 0.083-4 | 0.288 | 0.083 | 33600 | 21142 | 21144 | 9021 | 9027.6 | 0.427 | 1892 | 808 | |
| | Mean | | 0.357 | 0.083 | 33733 | 23481 | 23483 | 11482 | 11490 | 0.484 | 1732 | 828 | |
| | SD | | 0.124 | 0 | 907 | 3835 | 3836 | 3242 | 3244 | 0.1 | 259 | 62.2 | |
| PO | 7 | 1-4 | 0.313 | 0.250 | 9130 | 11076 | 11080 | 9588 | 9604 | 0.867 | | | |
| | 8 | 0.5-8 | 0.959 | 0.250 | 8330 | 12787 | 12820 | 20769 | 21076 | 1.644 | | | |
| | 9 | 0.5-8 | 1.173 | 0.250 | 9540 | 12172 | 12353 | 14572 | 16326 | 1.322 | | | |
| | Mean | | 0.815 | 0.250 | 9000 | 12012 | 12084 | 14976 | 15669 | 1.28 | | | |
| | SD | | 0.448 | 0.000 | 615 | 867 | 901 | 5602 | 5764 | 0.390 | | | 22.60% |

TABLE 8

Plasma pharmacokinetic parameters PEG-Pirfenidone after IV (96 mg/kg) or PO (96 mg/kg) administration to SD Rat

| Dosing Route | Rat | $T_{1/2}$_range* (h) | $T_{1/2}$ (h) | $T_{max}$ (h) | $C_{max}$ (ng/mL) | $AUC_{0-t}$ (ng·h/mL) | $AUC_{0-\infty}$ (ng·h/mL) | $AUMC_{0-t}$ (h*h*n g/mL) | $AUMC_{0-\infty}$ (h*h*n g/mL) | $MRT_{INF}$ (h) | CL(/F) (mL/h/kg) | Vss (/F) (mL/kg) | F % |
|---|---|---|---|---|---|---|---|---|---|---|---|---|---|
| IV | 4 | 1-8 | 0.804 | 0.083 | 44227 | 26338 | 26353 | 16980 | 17118 | 0.650 | 3643 | 2366 | |
| | 5 | 0.083-4 | 1.77 | 0.083 | 56484 | 32960 | 32968 | 20439 | 20640 | 0.626 | 2912 | 1823 | |
| | 6 | 2-8 | 1.43 | 0.083 | 96487 | 43292 | 43367 | 17108 | 17863 | 0.412 | 2214 | 912 | |
| | Mean | | 1.33 | 0.083 | 65733 | 34197 | 34229 | 18176 | 18540 | 0.563 | 2923 | 1700 | |
| | SD | | 0.489 | 0 | 27330 | 8544 | 8577 | 1961 | 1856 | 0.1 | 715 | 734.9 | |
| PO | 10 | 2-8 | 1.01 | 0.250 | 8298 | 4853 | 4858 | 3178 | 3221 | 0.663 | | | |
| | 11 | 2-8 | 1.34 | 0.250 | 40817 | 30468 | 30533 | 19172 | 19815 | 0.649 | | | |
| | 12 | 2-8 | 1.19 | 0.250 | 21638 | 15112 | 15123 | 8441 | 8544 | 0.565 | | | |
| | Mean | | 1.180 | 0.250 | 23584 | 16811 | 16838 | 10264 | 10527 | 0.626 | | | |
| | SD | | 0.167 | 0.000 | 16346 | 12892 | 12923 | 8151 | 8473 | 0.053 | | | 49.16% |

REFERENCES

1. Mann D L. The emerging role of innate immunity in the heart and vascular system: for whom the cell tolls. Circ Res. 2011; 108(9):1133-45.
2. Rymer J A, Newby. L. K. Failure to launch: Targeting inflammation in acute coronary syndromes. JACC: Basic to Translational Science. 2017; 2(484-97.
3. Carter N J. Pirfenidone: in idiopathic pulmonary fibrosis. Drugs. 2011; 71(13):1721-32.
4. Wang Y, Wu Y, Chen J, Zhao S, and Li H. Pirfenidone attenuates cardiac fibrosis in a mouse model of TAC-induced left ventricular remodeling by suppressing NLRP3 inflammasome formation. Cardiology. 2013; 126(1):1-11.
5. Yamagami K, Oka T, Wang Q, Ishizu T, Lee J K, Miwa K, Akazawa H, Naito A T, Sakata Y, and Komuro I. Pirfenidone exhibits cardioprotective effects by regulating myocardial fibrosis and vascular permeability in pressure-overloaded hearts. Am J Physiol Heart Circ Physiol. 2015; 309(3): H512-22.
6. Yamazaki T, Yamashita N, Izumi Y, Nakamura Y, Shiota M, Hanatani A, Shimada K, Muro T, Iwao H, and Yoshiyama M. The antifibrotic agent pirfenidone inhibits angiotensin II-induced cardiac hypertrophy in mice. Hypertens Res. 2012; 35(1):34-40.
7. Mirkovic S, Seymour A M, Fenning A, Strachan A, Margolin S B, Taylor S M, and Brown L. Attenuation of cardiac fibrosis by pirfenidone and amiloride in DOCA-salt hypertensive rats. Br J Pharmacol. 2002; 135(4):961-8.
8. Van Erp C, Irwin N G, and Hoey A J. Long-term administration of pirfenidone improves cardiac function in mdx mice. Muscle Nerve. 2006; 34(3):327-34.
9. Miric G, Dallemagne C, Endre Z, Margolin S, Taylor S M, and Brown L. Reversal of cardiac and renal fibrosis by pirfenidone and spironolactone in streptozotocin-diabetic rats. Br J Pharmacol. 2001; 133(5): 687-94.
10. Lee K W, Everett T Ht, Rahmutula D, Guerra J M, Wilson E, Ding C, and Olgin J E. Pirfenidone prevents the development of a vulnerable substrate for atrial fibrillation in a canine model of heart failure. Circulation. 2006; 114(16):1703-12.
11. Nguyen D T, Ding C, Wilson E, Marcus G M, and Olgin J E. Pirfenidone mitigates left ventricular fibrosis and dysfunction after myocardial infarction and reduces arrhythmias. Heart Rhythm. 2010; 7(10):1438-45.
12. Li C, Han R, Kang L, Wang J, Gao Y, Li Y, He J, and Tian J. Pirfenidone controls the feedback loop of the AT1R/p38 MAPK/renin-angiotensin system axis by regulating liver X receptor-alpha in myocardial infarction-induced cardiac fibrosis. Sci Rep. 2017; 7(40523.
13. Lavine K J, Epelman S, Uchida K, Weber K J, Nichols C G, Schilling J D, Ornitz D M, Randolph G J, and Mann D L. Distinct macrophage lineages contribute to disparate patterns of cardiac recovery and remodeling in the neonatal and adult heart. Proc Natl Acad Sci USA. 2014; 111(16029-34.
14. Epelman S, Lavine K J, Beaudin A E, Sojka D K, Carrero J A, Calderon B, Brija T, Gautier E L, Ivanov S, Satpathy A T, et al. Embryonic and adult-derived resident cardiac macrophages are maintained through distinct mechanisms at steady state and during Inflammation. Immunity. 2014; 40(1):91-104.
15. Lavine K J, Kovacs A, Weinheimer C, and Mann D L. Repetitive myocardial ischemia promotes coronary growth in the adult mammalian heart. J Am Heart Assoc. 2013; 2(5):e000343.
16. Kantor A B, Stall A M, Adams S, and Herzenberg L A. Differential development of progenitor activity for three B-cell lineages. Proc Natl Acad Sci USA. 1992; 89(8): 3320-4.
17. Rahman Z S. Impaired clearance of apoptotic cells in germinal centers: implications for loss of B cell tolerance and induction of autoimmunity. Immunol Res. 2011; 51(2-3):125-33.
18. Zhang W, Lavine K J, Epelman S, Evans S A, Weinheimer C J, Barger P M, and Mann D L. Necrotic myocardial cells release damage-associated molecular patterns that provoke fibroblast activation in vitro and trigger myocardial inflammation and fibrosis in vivo. J Am Heart Assoc. 2015; 4(6):e001993.
19. Xu H, Liew L N, Kuo I C, Huang C H, Goh D L, and Chua K Y. The modulatory effects of lipopolysaccharide-stimulated B cells on differential T-cell polarization. Immunology. 2008; 125(2):218-28.
20. Bonner F, Borg N, Burghoff S, and Schrader J. Resident cardiac immune cells and expression of the ectonucleotidase enzymes CD39 and CD73 after ischemic injury. PLoS One. 2012; 7(4):e34730.
21. Ramos G C, van den Berg A, Nunes-Silva V, Weirather J, Peters L, Burkard M, Friedrich M, Pinnecker J, Abesser M, Heinze K G, et al. Myocardial aging as a T-cell-mediated phenomenon. Proc Natl Acad Sci USA. 2017; 114(12):E2420-E9.
22. Yan X, Anzai A, Katsumata Y, Matsuhashi T, Ito K, Endo J, Yamamoto T, Takeshima A, Shinmura K, Shen W, et al. Temporal dynamics of cardiac immune cell accumulation following acute myocardial infarction. J Mol Cell Cardiol. 2013; 62(24-35.

23. Zouggari Y, Ait-Oufella H, Bonnin P, Simon T, Sage A P, Guerin C, Vilar J, Caligiuri G, Tsiantoulas D, Laurans L, et al. B lymphocytes trigger monocyte mobilization and impair heart function after acute myocardial infarction. *Nat Med.* 2013; 19(10):1273-80.
24. Horckmans M, Bianchini M, Santovito D, Megens R T A, Springael J Y, Negri I, Vacca M, Di Eusanio M, Moschetta A, Weber C, et al. Pericardial Adipose Tissue Regulates Granulopoiesis, Fibrosis and Cardiac Function After Myocardial Infarction. *Circulation.* 2017.
25. Cordero-Reyes A M, Youker K A, Trevino A R, Celis R, Hamilton D J, Flores-Arredondo J H, Orrego C M, Bhimaraj A, Estep J D, and Torre-Amione G. Full Expression of Cardiomyopathy Is Partly Dependent on B-Cells: A Pathway That Involves Cytokine Activation, Immunoglobulin Deposition, and Activation of Apoptosis. *J Am Heart Assoc.* 2016; 5(1).
26. Zhang M, Michael L H, Grosjean S A, Kelly R A, Carroll M C, and Entman M L. The role of natural IgM in myocardial ischemia-reperfusion injury. *J Mol Cell Cardiol.* 2006; 41(1):62-7.
27. Shen P, and Fillatreau S. Antibody-independent functions of B cells: a focus on cytokines. *Nat Rev Immunol.* 2015; 15(7):441-51.
28. Rubtsova K, Rubtsov A V, Cancro M P, and Marrack P. Age-Associated B Cells: A T-bet-Dependent Effector with Roles in Protective and Pathogenic Immunity. *J Immunol.* 195(5):1933-7.
29. Hua Z, and Hou B. TLR signaling in B-cell development and activation. *Cell Mol Immunol.* 2013; 10(2):103-6.
30. Yamamoto M, Sato S, Hemmi H, Sanjo H, Uematsu S, Kaisho T, Hoshino K, Takeuchi O, Kobayashi M, Fujita T, et al. Essential role for TIRAP in activation of the signalling cascade shared by TLR2 and TLR4. *Nature.* 2002; 420(6913):324-9.
31. Bizargity P, Liu K, Wang L, Hancock W W, and Visner G A. Inhibitory effects of pirfenidone on dendritic cells and lung allograft rejection. *Transplantation.* 2012; 94(2): 114-22.
32. Mann D L. Innate Immunity and the Failing Heart: The Cytokine Hypothesis Revisited. *Circ Res.* 2015; 116(7): 1254-68.
33. Zouggari Y, Ait-Oufella H, Bonnin P, Simon T, Sage A P, Guerin C, Vilar J, Caligiuri G, Tsiantoulas D, Laurans L, et al. B lymphocytes trigger monocyte mobilization and impair heart function after acute myocardial infarction. *Nat Med.* 2013; 19(10):1273-80.
34. Nossuli T O, Lakshminarayanan V, Baumgarten G, Taffet G E, Ballantyne C M, Michael L H, and Entman M L. A chronic mouse model of myocardial ischemia-reperfusion: essential in cytokine studies. *Am J Physiol Heart Circ Physiol.* 2000; 278(4):H1049-H55.
35. Burchfield J S, Dong J W, Sakata Y, Gao F, Tzeng H P, Topkara V K, Entman M L, Sivasubramanian N, and Mann D L. The Cytoprotective Effects of Tumor Necrosis Factor are Conveyed Through Tumor Necrosis Factor Receptor Associated Factor 2 in the Heart. *Circ Heart Fail.* 2010; 3(157-64.
36. Tzeng H P, Evans S, Gao F, Chambers K, Topkara V K, Sivasubramanian N, Barger P M, and Mann D L. Dysferlin Mediates the Cytoprotective Effects of TRAF2 Following Myocardial Ischemia Reperfusion Injury. *J Am Heart Assoc.* 2014; 3(e000662.
37. Schaefer C J, Ruhrmund D W, Pan L, Seiwert S D, and Kossen K. Antifibrotic activities of pirfenidone in animal models. *Eur Respir Rev.* 2011; 20(120):85-97.
38. Lavine K J, Sintek M, Novak E, Ewald G, Geltman E, Joseph S, Pfeifer J, and Mann D L. Coronary collaterals predict improved survival and allograft function in patients with coronary allograft vasculopathy. *Circ Heart Fail.* 2013; 6(4):773-84.
39. Kanno S, Lerner D L, Schuessler R B, Betsuyaku T, Yamada K A, Saffitz J E, and Kovacs A. Echocardiographic evaluation of ventricular remodeling in a mouse model of myocardial infarction. *J Am Soc Echocardiogr.* 2002; 15(6):601-9.
40. Misharin A V, Saber R, and Perlman H. Eosinophil contamination of thioglycollate-elicited peritoneal macrophage cultures skews the functional readouts of in vitro assays. *J Leukoc Biol.* 2012; 92(2):325-31.
41. Trapnell C, Pachter L, and Salzberg S L. TopHat: discovering splice junctions with RNA-Seq. *Bioinformatics.* 2009; 25(9):1105-11.
42. Anders S, Pyl P T, and Huber W. HTSeq—a Python framework to work with high-throughput sequencing data. *Bioinformatics.* 31(2):166-9.
43. Zhou X, Lindsay H, and Robinson M D. Robustly detecting differential expression in RNA sequencing data using observation weights. *Nucleic Acids Res.* 42(11):e91.
44. Huang da W, Sherman B T, and Lempicki R A. Systematic and integrative analysis of large gene lists using DAVID bioinformatics resources. *Nat Protoc.* 2009; 4(1): 44-57.

What is claimed is:
1. A compound of formula (I):

wherein:
R$^1$, R$^2$, R$^3$, R$^4$, and R$^5$ are each independently selected from the group consisting of hydrogen, deuterium, and L-X-B, provided that at least one of R$^2$, R$^4$, and R$^5$ is L-X-B;
wherein L is a C$_{1-12}$ alkyl linker; X is O-PEG NH(CH$_2$)$_m$O-PEG, or S(CH$_2$)$_m$O-PEG; m is an integer from 1-10; wherein PEG is selected from the group consisting of mPEG (methoxy polyethylene glycol), linear PEG, branched PEG, multi-arm PEG, and PEG-lipid; B is selected from the group consisting of hydrogen, deuterium, a substituted or unsubstituted C$_1$ to C$_6$ alkyl, a substituted or unsubstituted C$_1$ to C$_6$ alkenyl, a substituted or unsubstituted C$_1$ to C$_6$ alkynyl, a substituted or unsubstituted aryl, a substituted or unsubstituted heteroaryl, and deuterated versions thereof; and
A is selected from the group consisting of hydrogen, deuterium, halogen, CF$_3$, CD$_3$, CN, OH, OCH$_3$, OR", SR", NR"R", NR"COR", NR"CONR"R", NR"CO$_2$R", COR", CO$_2$R", NOR", NO$_2$, CONR"R", OC(O) NR"R", SO$_2$R", SO$_2$NR"R", NR"SO$_2$R", NR"SO$_2$NR"R", C(O)C(O)R", and C(O)CH$_2$C(O)R", a substituted or unsubstituted C$_1$ to C$_6$ alkyl, a substituted or unsubstituted C$_1$ to C$_6$ alkenyl, a substituted or unsubstituted $C_1$ to $C_6$ alkynyl, a substituted or unsubstituted aryl, and a substituted or unsubstituted heteroaryl; and each R" is independently selected from the group consisting of hydrogen, substituted $C_1$-$C_4$ aliphatic moiety, and an aliphatic moiety containing nitrogen, oxygen, or sulfur, or, alternatively, two R" moieties bound to the same nitrogen atom are optionally taken together with the nitrogen atom to form a 3-7 membered saturated or unsaturated ring having 1-2 additional heteroatoms independently selected from the group consisting of nitrogen, oxygen, and sulfur.

2. The compound of claim 1, wherein the PEG or mPEG has a molecular weight ranging from about 100 to about 50,000 Daltons, about 200 to about 50,000 Daltons, about 300 to about 50,000 Daltons, about 400 to about 50,000 Daltons, about 500 to about 50,000 Daltons, about 600 to about 50,000 Daltons, about 700 to about 50,000 Daltons, about 800 to about 50,000 Daltons, about 900 to about 50,000 Daltons, from about 1,000 to about 50,000 Daltons, from about 1,500 to about 50,000, from about 2,000 to about 50,000, from about 2,500 to about 50,000, from about 3,000 to about 50,000, from about 3,500 to about 50,000, from about 4,000 to about 50,000, from about 4,500 to about 50,000, from about 5,000 to about 50,000, from about 5,500 to about 50,000, from about 6,000 to about 50,000, from about 6,500 to about 50,000, from about 7,000 to about 50,000, from about 7,500 to about 50,000, from about 8,000 to about 50,000, from about 8,500 to about 50,000, from about 9,000 to about 50,000, from about 9,500 to about 50,000, from about 10,000 to about 50,000, from about 11,000 to about 50,000, from about 12,000 to about 50,000, from about 13,000 to about 50,000, from about 14,000 to about 50,000 Daltons, from about 15,000 to about 50,000 Daltons, from about 16,000 to about 50,000 Daltons, from about 17,000 to about 50,000 Daltons, from about 18,000 to about 50,000 Daltons, from about 19,000 to about 50,000 Daltons, from about 20,000 to about 50,000 Daltons, from about 30,000 to about 50,000 Daltons, or from about 40,000 to about 50,000 Daltons.

3. The compound of claim 1, wherein $R^1$ is selected from the group consisting of hydrogen and deuterium.

4. The compound of claim 3, wherein $R^1$ is H.

5. The compound of claim 1, wherein $R^2$ L-X-B.

6. The compound of claim 5, wherein L is a $C_{1-2}$ alkyl linker; X is O-PEG, wherein PEG is selected from the group consisting of linear PEG, branched PEG, multi-arm PEG, and PEG-lipid; and B is $CH_3$.

7. The compound of claim 1, wherein $R^3$ is selected from the group consisting of hydrogen and L-X-B, wherein L is a $C_{1-3}$ alkyl linker; X is O-PEG or $NH(CH_2)_mO$-PEG, wherein PEG is selected the group consisting of mPEG (methoxy polyethylene glycol), linear PEG, branched PEG, multi-arm PEG, and PEG-lipid; m is an integer from 2-3; and B is $CH_3$.

8. The compound of claim 1, wherein $R^4$ is L-X-B.

9. The compound of claim 8, wherein L is a $C_{1-3}$ alkyl linker; X is O-PEG or $NH(CH_2)_mO$-PEG, wherein PEG is selected from the group consisting of mPEG (methoxy polyethylene glycol), linear PEG, branched PEG, multi-arm PEG, and PEG-lipid; m is an integer from 2-3; and B is $CH_3$.

10. The compound of claim 1, wherein $R^5$ is L-X-B, wherein L is $CH_3$; X is O-PEG, wherein PEG is selected from the group consisting of mPEG (methoxy polyethylene glycol), linear PEG, branched PEG, multi-arm PEG, and PEG-lipid; and B is $CH_3$.

11. The compound of claim 1, wherein A is selected from the group consisting of hydrogen, halogen, $CF_3$, $CD_3$, and a substituted or unsubstituted $C_1$ to $C_6$ alkyl.

12. The compound of claim 11, wherein A is selected from the group consisting of $CH_3$, $CF_3$, $CD_3$, and $CH_2$-cyclopropyl.

13. A compound selected from the group consisting of

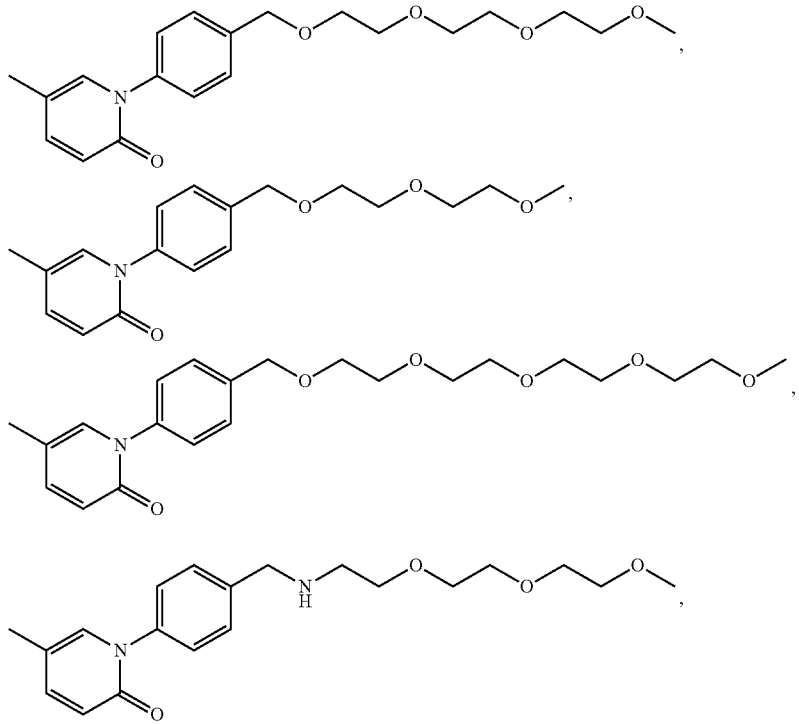

-continued

14. A compound of formula (II):

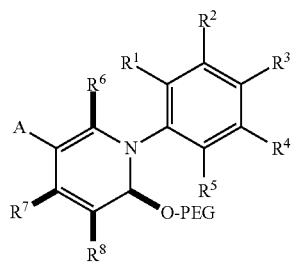

wherein:

$R^1$, $R^2$, $R^3$, $R^4$, $R^5$, $R^6$, $R^7$, and $R^8$ are each independently selected from the group consisting of hydrogen, deuterium and L-X-B;

wherein L is a $C_{1-12}$ alkyl linker; X is O-PEG, $NH(CH_2)_m$O-PEG, or $S(CH_2)_m$O-PEG; m is an integer from 1-10; wherein PEG is selected from the group of mPEG (methoxy polyethylene glycol), linear PEG, branched PEG, multi-arm PEG, and PEG-lipid; B is selected from the group consisting of hydrogen, deuterium, a substituted or unsubstituted $C_1$ to $C_6$ alkyl, a substituted or unsubstituted $C_1$ to $C_6$ alkenyl, a substituted or unsubstituted $C_1$ to $C_6$ alkynyl, a substituted or unsubstituted aryl, a substituted or unsubstituted heteroaryl, and deuterated versions thereof;

O-PEG is selected from the group consisting of mPEG (methoxy polyethylene glycol), linear PEG, branched PEG, multi-arm PEG, and PEG-lipid, wherein the PEG end-cap is selected from the group consisting of hydrogen, deuterium a substituted or unsubstituted $C_1$ to $C_6$ alkyl, a substituted or unsubstituted $C_1$ to $C_6$ alkenyl, a substituted or unsubstituted $C_1$ to $C_6$ alkynyl, a substituted or unsubstituted aryl, a substituted or unsubstituted heteroaryl, or and deuterated versions thereof;

A is selected from the group consisting of hydrogen, deuterium, halogen, $CF_3$, $CD_3$, CN, OH, $OCH_3$, OR", SR", NR"R", NR"COR", NR"CONR"R", NR"$CO_2$R", COR", $CO_2$R", NOR", $NO_2$, CONR"R", OC(O)NR"R", $SO_2$R", $SO_2$NR"R", NR"$SO_2$R", NR"$SO_2$NR"R", C(O)C(O)R", and C(O)$CH_2$C(O)R", a substituted or unsubstituted $C_1$ to $C_6$ alkyl, a substituted or unsubstituted $C_1$ to $C_6$ alkenyl, a substituted or unsubstituted $C_1$ to $C_6$ alkynyl, a substituted or unsubstituted aryl, and a substituted or unsubstituted heteroaryl;

R" may be independently selected from the group consisting of hydrogen, substituted $C_1$-$C_4$ aliphatic moiety, aliphatic moiety containing nitrogen, oxygen, or sulfur, or alternately, two R" moieties bound to the same nitrogen atom are optionally taken together with the nitrogen atom to form a 3-7 membered saturated or unsaturated ring having 1-2 additional heteroatoms independently selected from the group consisting of nitrogen, oxygen, or sulfur.

15. The compound of claim 14, wherein the PEG or mPEG has a molecular weight ranging from about 100 to about 50,000 Daltons, about 200 to about 50,000 Daltons, about 300 to about 50,000 Daltons, about 400 to about 50,000 Daltons, about 500 to about 50,000 Daltons, about 600 to about 50,000 Daltons, about 700 to about 50,000 Daltons, about 800 to about 50,000 Daltons, about 900 to about 50,000 Daltons, from about 1,000 to about 50,000 Daltons, from about 1,500 to about 50,000, from about 2,000 to about 50,000, from about 2,500 to about 50,000, from about 3,000 to about 50,000, from about 3,500 to about 50,000, from about 4,000 to about 50,000, from about 4,500 to about 50,000, from about 5,000 to about 50,000, from about 5,500 to about 50,000, from about 6,000 to about 50,000, from about 6,500 to about 50,000, from about 7,000 to about 50,000, from about 7,500 to about 50,000, from about 8,000 to about 50,000, from about 8,500 to about 50,000, from about 9,000 to about 50,000, from about 9,500 to about 50,000, from about 10,000 to about 50,000, from about 11,000 to about 50,000, from about 12,000 to about 50,000, from about 13,000 to about 50,000, from about 14,000 to about 50,000 Daltons, from about 15,000 to about 50,000 Daltons, from about 16,000 to about 50,000 Daltons, from about 17,000 to about 50,000 Daltons, from about 18,000 to about 50,000 Daltons, from about 19,000 to about 50,000 Daltons, from about 20,000 to about 50,000 Daltons, from about 30,000 to about 50,000 Daltons, or from about 40,000 to about 50,000 Daltons.

16. A method of modulating the activity of non-malignant B cells and decreasing the recruitment of non-malignant B cells to an organ of a subject in need thereof, comprising administering to the subject a composition comprising the compound of claim 1.

17. The method of claim 16, wherein the subject has severe organ damage, wherein the organ is selected from the group consisting of heart, liver, kidney, gut, and brain.

18. The method of claim 16, wherein the subject has chronic heart failure, wherein organ damage is present, wherein the organ is selected from the group consisting of heart, kidney, liver, gut, and brain.

* * * * *